US008618169B2

(12) United States Patent
Attali et al.

(10) Patent No.: US 8,618,169 B2
(45) Date of Patent: *Dec. 31, 2013

(54) DERIVATIVES OF N-PHENYLANTHRANILIC ACID AND 2-BENZIMIDAZOLONE AS POTASSIUM CHANNEL AND/OR NEURON ACTIVITY MODULATORS

(75) Inventors: Bernard Attali, Rechovot (IL); Asher Peretz, Givataim (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/424,553

(22) Filed: Mar. 20, 2012

(65) Prior Publication Data
US 2012/0178785 A1 Jul. 12, 2012

Related U.S. Application Data

(60) Continuation of application No. 12/591,090, filed on Nov. 6, 2009, now Pat. No. 8,278,357, which is a division of application No. 11/110,669, filed on Apr. 21, 2005, now Pat. No. 7,632,866, which is a continuation-in-part of application No. PCT/IL03/00855, filed on Oct. 21, 2003.

(60) Provisional application No. 60/419,525, filed on Oct. 21, 2002, provisional application No. 60/654,448, filed on Feb. 22, 2005.

(51) Int. Cl.
*A61K 31/16* (2006.01)
*C07D 233/00* (2006.01)
*C07D 239/00* (2006.01)

(52) U.S. Cl.
USPC .......................... 514/613; 564/123; 564/161

(58) Field of Classification Search
USPC .................................. 514/613; 564/123, 161
See application file for complete search history.

(56) References Cited

U.S. PATENT DOCUMENTS

| 3,652,762 | A | 3/1972 | Sallmann et al. |
| 4,016,166 | A | 4/1977 | Noda et al. |
| 4,283,532 | A | 8/1981 | Nohara |
| 4,734,434 | A | 3/1988 | Procaccini et al. |
| 4,857,645 | A | 8/1989 | Makoto et al. |
| 5,017,604 | A | 5/1991 | Belliotti et al. |
| 5,384,330 | A | 1/1995 | Dieter et al. |
| 5,565,483 | A | 10/1996 | Hewawasam et al. |
| 6,117,900 | A | 9/2000 | Rundfeldt et al. |
| 6,291,442 | B1 * | 9/2001 | Yellen ............... 514/155 |
| 6,291,523 | B1 | 9/2001 | Fujimoto et al. |
| 6,326,385 | B1 | 12/2001 | Wickenden et al. |
| 6,348,486 | B1 | 2/2002 | Argentieri et al. |
| 6,355,666 | B1 | 3/2002 | Lai et al. |
| 6,355,680 | B1 | 3/2002 | Cohen |
| 6,472,165 | B1 | 10/2002 | Rundfeldt et al. |
| 6,589,986 | B2 | 7/2003 | Bowlby et al. |
| 6,593,349 | B2 | 7/2003 | McNaughton-Smith et al. |
| 7,378,442 | B1 | 5/2008 | Majeed et al. |
| 7,632,866 | B2 * | 12/2009 | Attali et al. ............ 514/613 |
| 2003/0055095 | A1 | 3/2003 | Baragi et al. |
| 2005/0250833 | A1 | 11/2005 | Attali et al. |
| 2008/0004245 | A1 | 1/2008 | Wallace et al. |
| 2010/0056591 | A1 | 3/2010 | Attali et al. |
| 2010/0137296 | A1 | 6/2010 | Attali et al. |

FOREIGN PATENT DOCUMENTS

| EP | 0131790 | 1/1985 |
| EP | 0307599 | 3/1989 |
| EP | 0335164 | 10/1989 |
| EP | 0336147 | 10/1989 |
| EP | 0452179 | 10/1991 |
| EP | 0554543 | 2/1996 |
| FR | 2411825 | 7/1979 |
| FR | 2462420 | 2/1981 |
| JP | 50-032189 | 3/1975 |
| JP | 50-095285 | 7/1975 |
| JP | 63-275549 | 11/1988 |
| JP | 63-275593 | 11/1988 |
| JP | 01-096158 | 4/1989 |
| JP | 05-132431 | 5/1993 |
| JP | 2002-509536 | 3/2002 |
| WO | WO 98/20864 | 5/1998 |
| WO | WO 99/01421 | 1/1999 |
| WO | WO 00/34248 | 6/2000 |
| WO | WO00-61541 | * 10/2000 |
| WO | WO 00/61541 | 10/2000 |
| WO | WO 01/05392 | 1/2001 |
| WO | WO 01/09612 | 2/2001 |
| WO | WO 01/19406 | 3/2001 |
| WO | WO 01/47562 | 7/2001 |
| WO | WO 01/78721 | 10/2001 |
| WO | WO 01/93680 | 12/2001 |

(Continued)

OTHER PUBLICATIONS

Communication Pursuant to Article 94(3) EPC Dated Mar. 13, 2012 From the European Patent Office Re. Application No. 03753909.5.
U.S. Appl. No. 60/419,525, Oct. 16, 2002, Attali et al.
Advisory Action Before the Filing of an Appeal Brief Dated Jan. 9, 2012 From the US Patent and Trademark Office Re.: U.S. Appl. No. 12/591,090.
Communication Pursuant to Article 94(3) EPC Dated Jan. 3, 2011 From the European Patent Office Re. Application No. 08808058.5.
Communication Pursuant to Article 94(3) EPC Dated Oct. 5, 2011 From the European Patent Office Re. Application No. 08808058.5.
Communication Pursuant to Article 94(3) EPC Dated Jun. 8, 2011 From the European Patent Office Re. Application No. 08808058.5.
International Preliminary Report on Patentability Dated Apr. 1, 2010 From the International Bureau of WIPO Re.: Application No. PCT/IL2008/001255.

(Continued)

*Primary Examiner* — Susannah Chung

(57) ABSTRACT

Compounds, compositions and methods are provided which are useful in the treatment of conditions such as central or peripheral nervous system disorders through the modulation of potassium ion flux through voltage-dependent potassium channels and/or depressing cortical and/or peripheral neuron activity are disclosed. Novel derivatives of N-phenylanthranilic acid are also disclosed.

7 Claims, 31 Drawing Sheets
(1 of 31 Drawing Sheet(s) Filed in Color)

(56) References Cited

FOREIGN PATENT DOCUMENTS

| | | | |
|---|---|---|---|
| WO | WO02-00167 | * | 1/2002 |
| WO | WO 02/00167 | | 1/2002 |
| WO | WO 02/36121 | | 5/2002 |
| WO | WO 02/065977 | | 8/2002 |
| WO | WO 02/074388 | | 9/2002 |
| WO | WO 03/103602 | | 12/2003 |
| WO | WO 04/000300 | | 12/2003 |
| WO | WO 2004/026808 | | 4/2004 |
| WO | WO 2004/035037 | | 4/2004 |
| WO | WO 2004/052840 | | 6/2004 |
| WO | WO 2005/009975 | | 2/2005 |
| WO | WO 2006/042387 | | 4/2006 |
| WO | WO 2006/117316 | | 11/2006 |
| WO | WO 2008/012602 | | 1/2008 |
| WO | WO 2008/029199 | | 3/2008 |
| WO | WO 2009/007827 | | 1/2009 |
| WO | WO 2009/037705 | | 3/2009 |
| WO | WO 2009/037707 | | 3/2009 |

OTHER PUBLICATIONS

International Preliminary Report on Patentability Dated Apr. 1, 2010 From the International Bureau of WIPO Re.: Application No. PCT/IL2008/001257.

International Search Report Dated Jun. 2, 2009 From the International Searching Authority Re.: Application No. PCT/IL2008/001255.

International Search Report Dated Apr. 5, 2004 From the International Searching Authority Re.: Application No. PCT/IL03/00855.

International Search Report Dated Mar. 6, 2009 From the International Searching Authority Re.: Application No. PCT/IL2008/001257.

Notice of Allowance Dated Feb. 13, 2012 From the US Patent and Trademark Office Re.: U.S. Appl. No. 12/591,090.

Office Action Dated Aug. 3, 2010 From the Israeli Patent Office Re.: Application No. 168217 and Its Translation Into English.

Office Action Dated May 27, 2010 From the Israeli Patent Office Re.: Application No. 168217 and Its Translation Into English.

Official Action Dated Sep. 1, 2010 From the US Patent and Trademark Office Re.: U.S. Appl. No. 12/591,090.

Official Action Dated Oct. 6, 2011 From the US Patent and Trademark Office Re. U.S. Appl. No. 12/452,353.

Official Action Dated Sep. 6, 2011 From the US Patent and Trademark Office Re.: U.S. Appl. No. 12/591,090.

Official Action Dated Dec. 8, 2008 From the US Patent and Trademark Office Re.: U.S. Appl. No. 11/110,669.

Official Action Dated Feb. 11, 2011 From the US Patent and Trademark Office Re. U.S. Appl. No. 12/452,353.

Official Action Dated Jul. 20, 2010 From the US Patent and Trademark Office Re.: U.S. Appl. No. 12/591,090.

Official Action Dated Mar. 22, 2011 From the US Patent and Trademark Office Re.: U.S. Appl. No. 12/591,090.

Official Action Dated Oct. 22, 2007 From the US Patent and Trademark Office Re.: U.S. Appl. No. 11/110,669.

Official Action Dated Apr. 23, 2010 From the US Patent and Trademark Office Re.: U.S. Appl. No. 12/591,090.

Official Action Dated Feb. 28, 2008 From the US Patent and Trademark Office Re.: U.S. Appl. No. 11/110,669.

Official Action Dated Oct. 29, 2010 From the US Patent and Trademark Office Re. U.S. Appl. No. 12/452,353.

Translation of Notice of Reason for Rejection Dated Jun. 8, 2010 From the Japanese Patent Office Re. Application No. 2004-544675.

Written Opinion Dated Jun. 2, 2009 From the International Searching Authority Re.: Application No. PCT/IL2008/001255.

Written Opinion Dated Mar. 6, 2009 From the International Searching Authority Re.: Application No. PCT/IL2008/001257.

Anonymous "Synthesis of Compounds", Supporting Text S1, XP007908469, p. 1-13, Dec. 26, 2007. Compounds 8, 11, 12, 13, 14, 15, 19, 20.

Baranauskas et al. "Kv3.4 Subunits Enhance the Repolarizing Efficiency of Kv3.1 Channels in Fast-Spiking Neurons", Nature Neuroscience, 6(3): 258-266, 2003.

Beilstein Database Beilstein, Beilstein Institute for Organic Chemistry, XP002516450, Database Accession No. Beilstein Registry No. 3410361, Apr. 2008. Abstract. & Levi et al., Journal of the Chemical Society, p. 1490, 1493, 1933.

Biervert et al. "A Potassium Channel Mutation in Neonatal Human Epilepsy", Science, 279: 403-406, Jan. 16, 1998.

Bonina et al. "Oligoethylene Ester Derivatives of Ketoprofen, Naxoroxen and Diclofenac as Oral Prodrugs: A Pharmacological Evaluation", Die Pharmazie, XP001539451, 57(8): 552-555, Aug. 1, 2002. Abstract, Compounds 3A-E, Table 4.

Butler et al. "Mslo, A Complex Mouse Gene Encoding "Maxi" Calcium-Activated Potassium Channels", Science, 261(5118): 221-225, 1993.

Congiu et al. "New Potential Anticancer Agents Based on the Anthranilic Acid Scaffold. Synthesis and Evaluation of Biological Activity", Journal of Medicinal Chemistry, XP007908449, 48(26): 8245-8252, Jan. 1, 2005. Fig.2, Tables 1-3.

Du et al. "Development Expression and Functional Characterization of the Potassium-Channel Subunit Kv3.1b in Parvalbumin-Containig Interneurons of the Hippocampus", The Journal of Neuroscience, 16(2): 506-518, 1996.

Fregnan et al. "Local Anti-Inflammatory Properties of Etoclofene. A New Fenamate Derivative", Pharmacology, XP009116638, 11(4): 213-219, Jan. 1, 1974. Abstract.

Heinemann et al. "Functional Characterization of Kv Channel ?-Subunits From Rat Brain", Journal of Physiology, 493(3): 625-633, 1996.

Jahnel et al. "Dual Expression of Mouse and Rat VRL-1 in the Dorsal Root Ganglion Derived Cell Line F-11 and Biochemical Analysis of VRL-1 After Heterologous Expression", European Journal of Biochemistry, 270: 4264-4271, 2003.

Joiner et al. "Formation of Intermediate-Conductance Calcium-Activated Potassium Channels by Interaction of Slack and Slo Subunits", Nature Neuroscience, 1: 462-469, 1998.

Jurman et al "Visual Identification of Individual Transfected Cells for Electrophsyiology Uding Antibody-Coated Beads", Biotechniques, 17(5): 876-881, 1994. Abstract.

Kalgutkar et al. "Amide Derivatives of Meclofenamic Acid as Selective Cyclooxygenase-2 Inhibitors", Bioorganic & Medicinal Chemistry Letters, XP002319950, 12: 521-524, Jan. 1, 2002. Table 1, Compounds 1-3.

Kananura et al. "The New Voltage Gated Potassium Channel KCNQ5 and Neonatal Convulsions", Genetics of Nervous System Diseases, 11(9): 2063-2067, 2000.

Kubisch et al. "KCNQ4, A Novel Potassium Channel Expressed in Sensory Outer Hair Cells, Is Mutated in Dominant Deafness", Cell, 96: 437-446, 1999.

Legrand et al. "Heterocyclic Sulfur Compounds. 1,2-Dihydro-3,1,2? 5-Benzothiazaphosphinine-2,4-Dihydrothiazoles (or Oxazoles)", Phosphorus and Sulfur and the Related Elements, 26(1): 111-117, 1986. Chemical Abstract, STN on the Web, IT Field [Online], Accession No. 106:32994, 1986.

Leppert et al. "Benign Familial Neonatal Convulsions Linked to Genetic Markers on Chromosome 20", Nature, 337(6208): 647-648, 1989. Abstract.

Liu et al. "Oxidative Stress and Potassium Channel Function", Clinical and Experimental Pharmacology and Physiology, 29(4): 305-311, 2002. Abstract.

Main et al. "Modulation of KCNQ2/3 Potassium Channels by the Novels Anticonvulsant Retigabine", Molecular Pharmacology, 58: 253-262, 2000.

Mayo Clinic Staff "Parkinson's Disease", Mayo Clinic Staff, Mayo Foundation for Medical Education and Research (MFMER), Retrieved From the Internet, 12 P., Feb. 15, 2011.

Meera et al. "Large Conductance Voltage- and Calcium-Dependent K+ Channel, A Distinct Member of Voltage-Dependent Ion Channels With Seven N-Terminal Transmembrane Segments (S0-S6), An Extracellular N Terminus, and an Intracellular (S9-S10) C Terminus", Proc. Natl. Acad. Sci. USA, 94: 14066-14071, 1997.

(56) References Cited

OTHER PUBLICATIONS

Passmore et al. "KCNQ/M Currents in Sensory Neurons: Significance for Pain Therapy", The Journal of Neuroscience, 23(18): 7227-7236, 2003.
Patini et al. "Bioisosterism: A Rational Approach in Drug Design", Chemical Reviews, 96: 3147-3176, 1996.
Pedarzani et al. "Control of Electrical Activity in Central Neurons by Modulating the Gating of Small Conductance Ca2+-Activated K+ Channels", The Journal of Biological Chemistry, 276(13): 9762-9769, 2001. Abstract.
Peretz et al. "A Tale of Switched Functions: From Cyclooxygenase Inhibition to M-Channel Modulation in New Diphenylamine Derivatives", PLoS ONE (Public Library of Science), XP009116544, 2(12/e1332): 1-13, Dec. 26, 2007. Table 1.
Peretz et al. "Meclofenamic Acid and Diclofenac, Novel Templates of KCNQ2/Q3 Potassium Channel Openers, Depress Cortical Neuron Activity and Exhibit Anticonvulsant Properties", Molecular Pharmacology, 67(4): 1-14, 2005.
Sanguinetti et al. "Coassembly of k Sub V LQT1 and MinK (IsK) Proteins to Form Cardiac I Sub Ks Potassium Channel", Nature, 384(6604): 80-83, 1996.
Schreiber et al. "Slo3, A Novel PH-Sensitive K+ Channel From Mammalian Spermatocytes", The Journal of Biological Chemistry, 273(6): 3509-3516, 1998.
Shah et al. "Molecular Correlates of the M-Current in Cultured Rat Hippocampal Neurons", The Journal of Physiology, 544: 29-37, 2002.
Shi et al. "? Subunits Promote K+ Channel Surface Expression Through Effects Early in Biosynthesis", Neuron, 16: 843-852, 1996.
Syme et al. "Pharmacological Activation of Cloned Intermediate- and Small-Conductance Ca+-Activated K+ Channels", American Journal of Physiology and Cell Physiology, 278: C570-0581, 2000.
Tatulian et al. "Activation of Expressed KCNQ Potassium Currents and Native Neuronal M-Type Potassium Currents by the Anti-Convulsant Drug Retigabine", The Journal of Neuroscience, 21(15): 5535-5545, 2001.
Trishin et al. "Reaction of Pentafluorophenyl(Diphenyl)Phosphine With Nitrilimines", Russian Journal of General Chemistry, XP002516449, 71(3): 471-475, 2001.
Vercouillie et al. "Synthesis and in Vitro Evaluation of Novel Derivatives of Diphenylsulfide as Serotonin Transporter Ligands", Bioorganic & Medicinal Chemistry Letters, XP025106339, 16(5): 1297-1300, Mar. 1, 2006. p. 1297, Abstract, p. 1298, Scheme 1, Compounds 5a-9a, 5b-9b.
Wang et al. "KCNQ2 and KCNQ3 Potassium Channel Subunits: Molecular Correlates of the M-Channel", Science, 282: 1890-1893, 1998.
Wei et al. "Eight Potassium Channel Families Revealed by the *C. elegans* Genome Project", Neuropharmacology, 35(7): 805-829, 1996.
Wickenden et al. "Characterization of KCNQ5/Q3 Potassium Channels Expressed in Mammalian Cells", British Journal of Pharmacology, 132: 381-384, 2001.
Wilson et al. "Hypoxia-Selective antitumor Agents. 1. Relationships Between Structure, Redox Properties and Hypoxia-Selective Cytotoxicity for 4-Substituted Derivatives of Nitracrine", Journal of Medicinal Chemistry, XP001016258, 32: 23-30, Jan. 1, 1989. p. 24, 'Scheme I', Compounds III, V.
Yang et al. "Functional Expression of Two KvLQT1-Related Potassium Channels Responsible for an Inherited Idiopathic Epilepsy", The Journal of Biological Chemistry, 273(31): 19419-19423, 1998.
Yue et al. "KCNQ/M Channels Control Spike Afterdepolarization and Burst Generation in Hippocampal Neurons", The Journal of Neuroscience, 24(19): 4614-4624, 2004.
Office Action Dated Dec. 31, 2012 From the Israel Patent Office Re. Application No. 204617 and Its Translation Into English.
Office Action Dated Jul. 16, 2012 From the State Intellectual Property Office of the People's Republic of China Re. Application No. 200880117585.8 and its Translation into English.
Search Report Dated Jul. 5, 2012 From the State Intellectual Property Office of the People's Republic of China Re. Application No. 200880117585.8 and its Translation into English.
Fleming et al. "Synthesis of Non-Steroidal Antiinflammatory Drug Analogues for Selective Studies on the COX-II Enzyme", Journal of Labelled Compounds and Radiopharmaceuticals, 38(1): 13-18, Jan. 1996.
Riu-Wen et al. "Synthesis and Anti-Inflammatory Activity of Benzenesulfonylfuroxan-Coupled Diclofenac", Acta Pharmaceutica Sinica 36(11): 821-826, 2001. (with an abstract in English).
Communication Pursuant to Article 94(3) EPC Dated Dec. 18, 2012 From the European Patent Office Re. Application No. 08808058.5.
Examination Report Dated May 30, 2007 From the Government of India, Patent Office Re.: Application No. 965/CHENP/2005.
Official Action Dated Mar. 21, 2013 From the US Patent and Trademark Office Re. U.S. Appl. No. 12/452,353.
Official Action Dated Sep. 4, 2013 From the US Patent and Trademark Office Re. U.S. Appl. No. 12/452,353.

\* cited by examiner

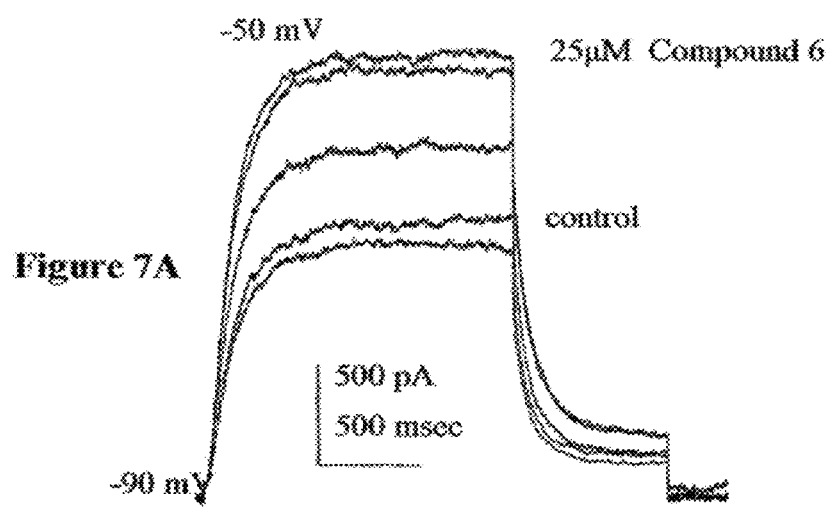
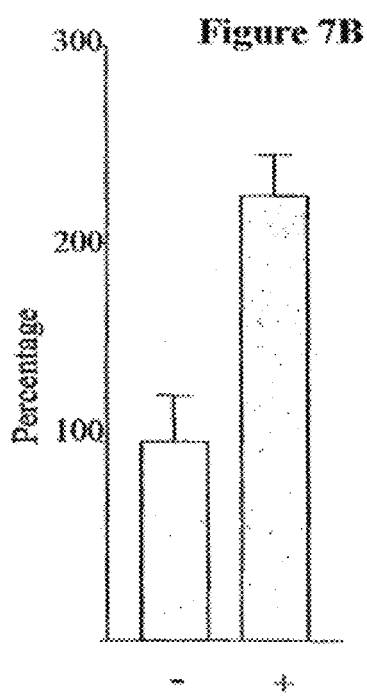
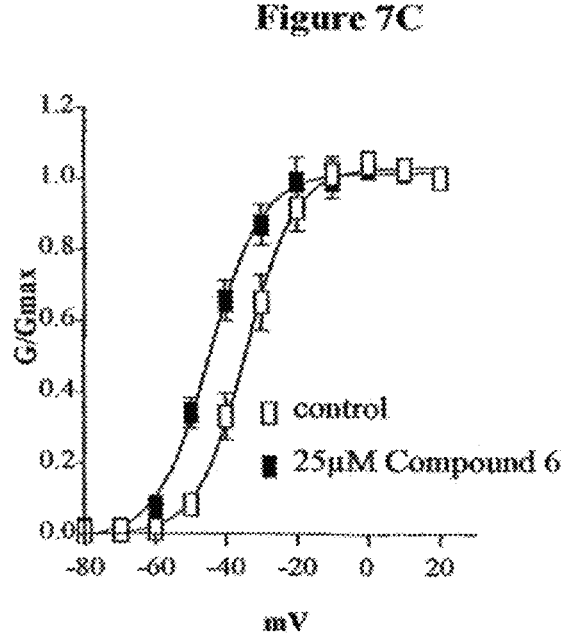

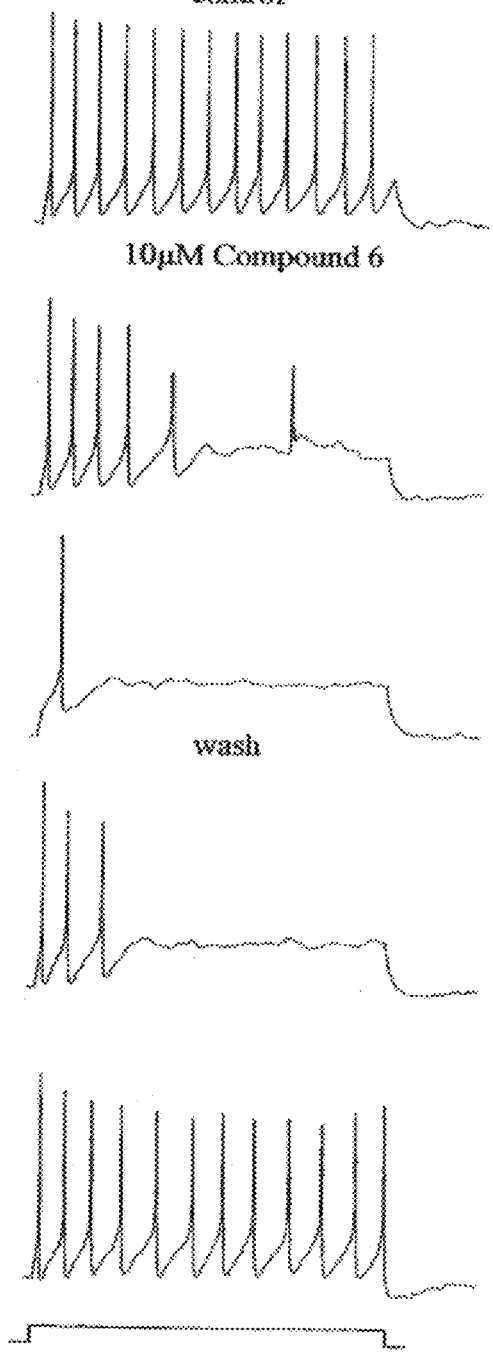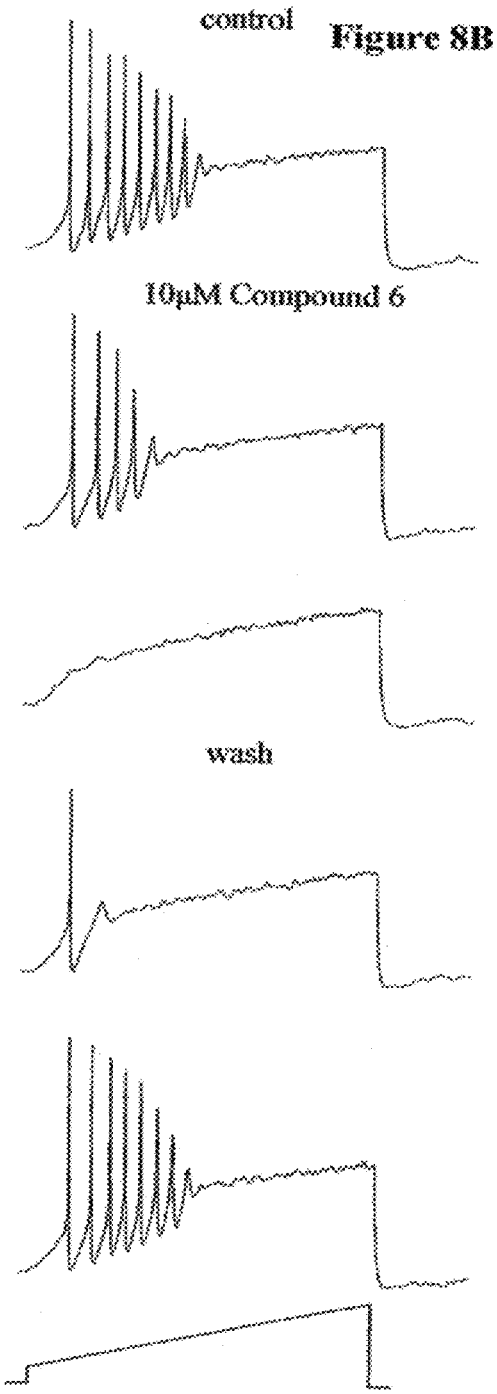

20μM Compound 6

10μM Compound 6

5μM Compound 6

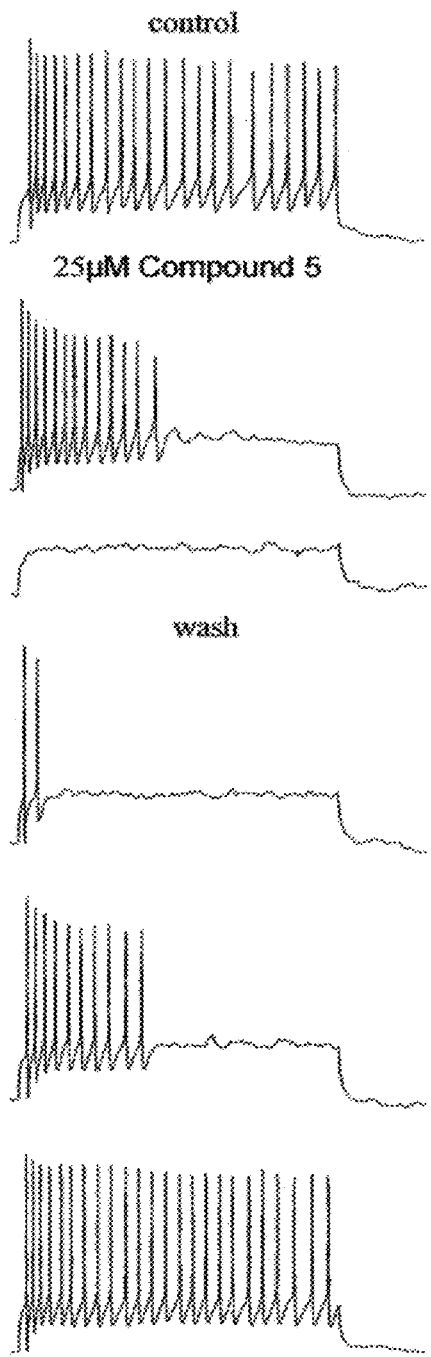
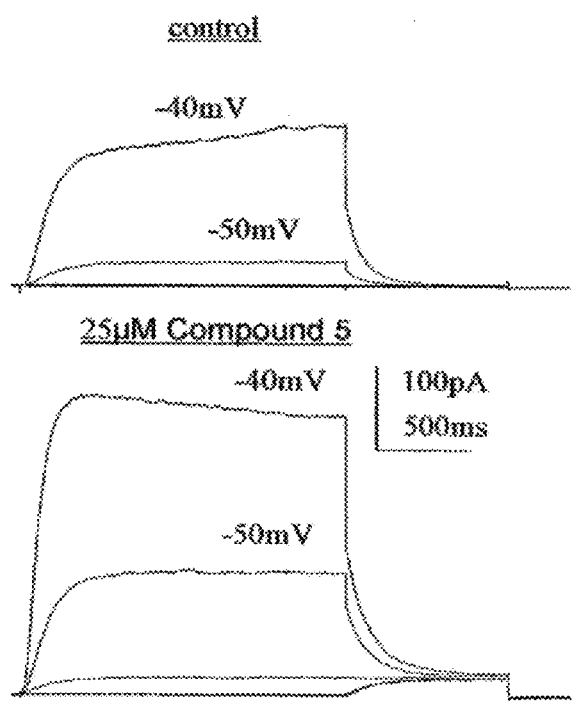
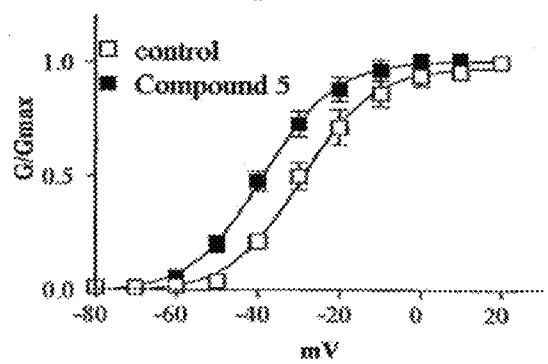
Figure 10A
Figure 10B
Figure 10C

20μM Compound 4

20μM Compound 9

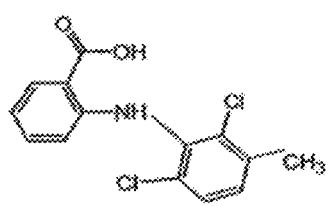
Compound 1
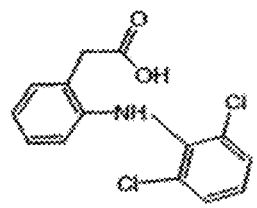
Compound 2
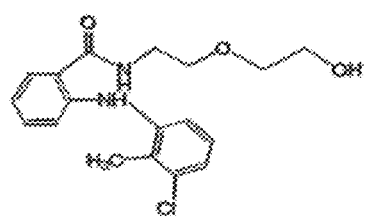
Compound 3
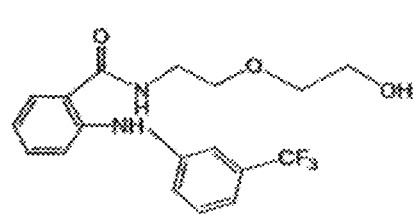
Compound 4
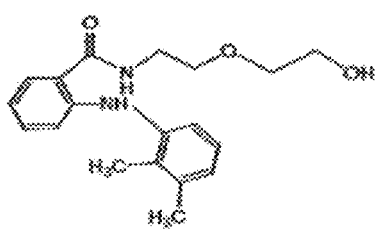
Compound 5
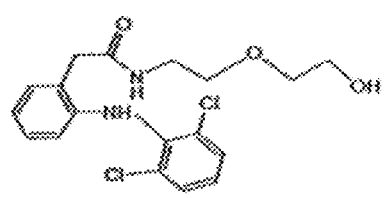
Compound 6
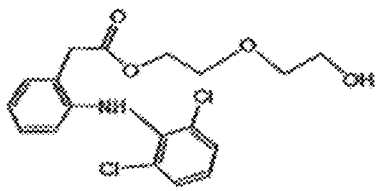
Compound 7
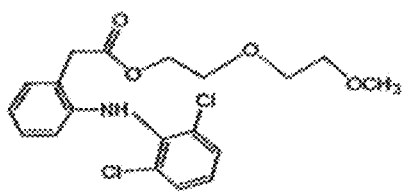
Compound 8
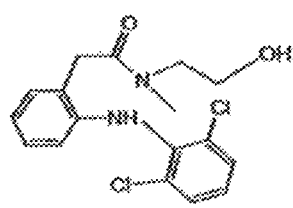
Compound 9
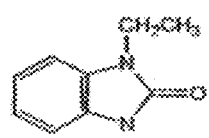
Compound 10
FIG. 17

Retigabine

Figure 19
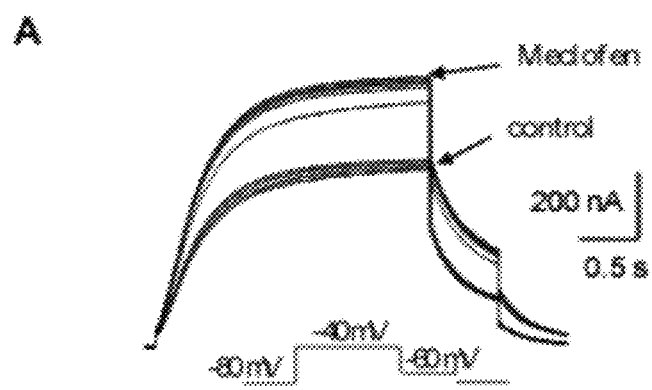
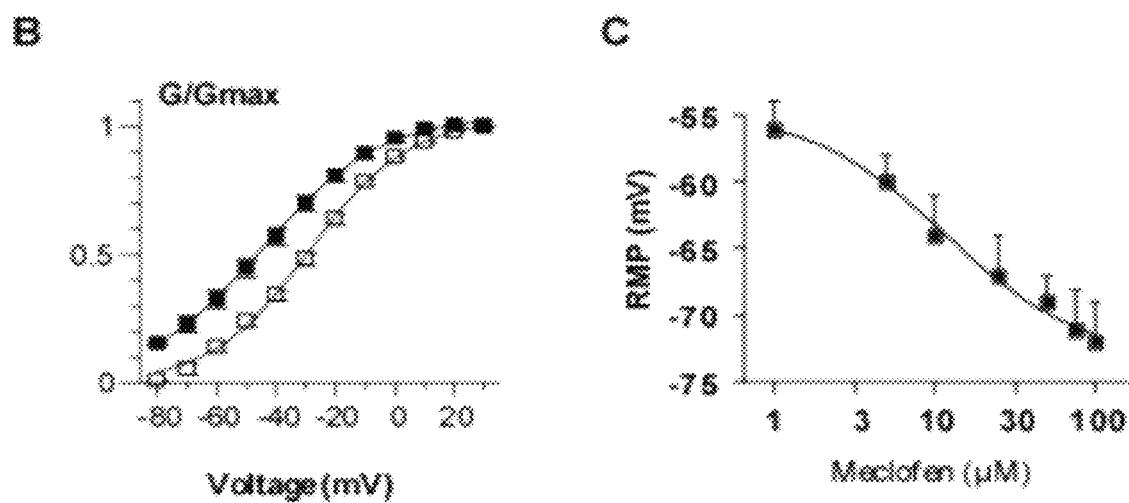

Channel opener site structure

X= O or NH

DERIVATIVES OF N-PHENYLANTHRANILIC ACID AND 2-BENZIMIDAZOLONE AS POTASSIUM CHANNEL AND/OR NEURON ACTIVITY MODULATORS

RELATED APPLICATIONS

This application is a continuation of U.S. patent application Ser. No. 12/591,090 filed on Nov. 6, 2009, which is a divisional of U.S. patent application Ser. No. 11/110,669 filed on Apr. 21, 2005, now U.S. Pat. No. 7,632,866, which is a continuation-in-part (CIP) of PCT Patent Application No. PCT/IL03/00855 filed on Oct. 21, 2003, which claims the benefit of priority of U.S. Provisional Patent Application No. 60/419,525, filed on Oct. 21, 2002. U.S. patent application Ser. No. 11/110,669 also claims the benefit of priority of U.S. Provisional Patent Application No. 60/654,448, filed on Feb. 22, 2005. The contents of all of the above applications are incorporated by reference as if fully set forth herein.

FIELD AND BACKGROUND OF THE INVENTION

The present invention relates to the field of pharmacology, and particularly to derivatives of N-phenylanthranilic acid and/or 2-benzimidazolone for the treatment of pathologies, especially pathologies related to potassium ion flux through voltage-dependent potassium channels and/or cortical and peripheral neuron activity.

Ion channels are cellular proteins that regulate the flow of ions, including calcium, potassium, sodium and chloride, into and out of cells. These channels are present in all animal cells and affect such processes as nerve transmission, muscle contraction, sensation processing and cellular secretion. Among the ion channels, potassium channels are the most ubiquitous and diverse, being found in a variety of animal cells such as nervous, muscular, glandular, immune, reproductive and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands and ATP-sensitivity.

Potassium channels have now been associated with a number of physiological processes, including regulation of heartbeat, dilation of arteries, release of insulin, excitability of nerve cells, and regulation of renal electrolyte transport. Potassium channels are made by alpha subunits that fall into at least 8 families, based on predicted structural and functional similarities [Wei et al., Neuropharmacology 35(7): 805-829 (1997)]. Three of these families (Kv, eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels have seven transmembrane domains [Meera et al., Proc. Natl. Acad. Sci. U.S.A. 94(25): 14066-71 (1997)] and are gated by both voltage and calcium or pH [Schreiber et al., J. Biol. Chem. 273: 3509-16 (1998)]. Another family, the inward rectifier potassium channels (Kir), belongs to a structural family containing two transmembrane domains, and an eighth functionally diverse family (TP, or "two-pore") contains two tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel [Heinemann et al., J. Physiol. 493: 625-633 (1996); Shi et al., Neuron 16(4): 843-852 (1996)]). In another example, the KQT family beta subunit, minK, primarily changes activation kinetics [Sanguinetti et al., Nature 384: 80-83 (1996)].

Slo or BK potassium channels are large conductance potassium channels found in a wide variety of tissues, both in the central nervous system and periphery. They play a key role in the regulation of processes such as neuronal integration, muscular contraction and hormone secretion. They may also be involved in processes such as lymphocyte differentiation and cell proliferation, spermatocyte differentiation and sperm motility. Three alpha subunits of the Slo family have been cloned, i.e., Slo1, Slo2, and Slo3 [Butler et al., Science 261: 221-224 (1993); Schreiber et al., J. Biol. Chem., 273: 3509-16 (1998); and Joiner et al., Nature Neurosci. 1: 462-469 (1998)]. These Slo family members have been shown to be voltage and/or calcium gated, and/or regulated by intracellular pH.

Certain members of the Kv family of potassium channels were recently renamed [see, Biervert, et al., Science 279: 403-406 (1998)]. KvLQT1 was re-named KCNQ1, and the KvLQT1-related channels (KvLR1 and KvLR2) were renamed KCNQ2 and KCNQ3, respectively. More recently, additional members of the KCNQ subfamily were identified. For example, KCNQ4 was identified as a channel expressed in sensory outer hair cells [Kubisch, et al., Cell 96(3): 437-446 (1999)]). KCNQ5 [Kananura et al., Neuroreport 11(9): 2063 (2000)], KCNQ2/3 [Main et al., Mol. Pharmacol. 58: 253-62 (2000)], KCNQ3/5 [Wickenden et al., Br. J. Pharma 132: 381 (2001)] and KCNQ6 have also recently been described.

KCNQ2 and KCNQ3 have been shown to be nervous system-specific potassium channels associated with benign familial neonatal convulsions ("BFNC"), a class of idiopathic generalized epilepsy [see, Leppert, et al., Nature 337: 647-648 (1989)]. These channels have been linked to M-current channels [see, Wang, et al., Science 282: 1890-1893 (1998)]. The discovery and characterization of these channels and currents provides useful insights into how these voltage dependent (Kv) potassium channels function in different environments, and how they respond to various activation mechanisms. Thus, for example, it was recently found that KCNQ2 and KCNQ3 α subunits are expressed in sensory dorsal root ganglion (DRG) neurons which are involved in nociceptive signaling pathways (Passmore et al., 23(18): 7227-36, 2003). Such information has now led to the identification of modulators of KCNQ2 and KCNQ3 potassium channels or the M-current, and the use of such modulators as therapeutic agents.

A potassium channel opener that has gained much attention is retigabine (N-(2-amino-4-(4-fluorobenzylamino)-phenyl)carbamic acid ethyl ester). Retigabine was first described in European Patent No. 554,543. Compounds related to retigabine have also been proposed for use as potassium channel modulators, see for example U.S. patent application Ser. No. 10/022,579.

Retigabine is highly selective for potassium channels consisting of the subunits KCNQ2 and KCNQ3. In addition, retigabine activates the homomultimerous channel, which contains only the subunit KCNQ2. Only marginal voltage-dependent currents are measurable in cells, which express only the homomeric channel from the KCNQ3 subunit (see, U.S. Pat. No. 6,472,165).

U.S. patent application Ser. No. 10/075,521 teaches 2,4-disubstituted pyrimidine-5-carboxamide derivatives as KCNQ potassium channel modulators.

U.S. patent application Ser. No. 10/160,582 teaches cinnamide derivatives as KCNQ potassium channel modulators.

U.S. Pat. No. 5,565,483 and U.S. patent application Ser. Nos. 10/312,123, 10/075,703 and 10/075,522 teach 3-substituted oxindole derivatives as KCNQ potassium channel modulators.

U.S. Pat. No. 5,384,330 teaches 1,2,4-triamino-benzene derivatives as KCNQ potassium channel modulators.

U.S. Pat. No. 6,593,349 teaches bisarylamines derivatives as KCNQ potassium channel modulators. The two aryl groups of the compounds taught in U.S. Pat. No. 6,593,349 are a pyridine derivative and a five-membered heterocyclic compound.

A significant disadvantage of the KCNQ potassium channel modulators known in the art is that these are generally difficult to prepare, requiring complex multi-step syntheses and that in some cases these modulators are non-specific or even toxic.

There is, hence, a widely recognized need for, and it would be highly advantageous to have new and effective potassium channel modulators devoid of the above limitations.

SUMMARY OF THE INVENTION

The present invention provides compounds that are generally effective potassium channel modulators, especially voltage-dependent potassium channels such as KCNQ2 channel, KCNQ3 channels and KCNQ2/3 channels. Also, the present invention provides compounds that are generally effective at depressing cortical and peripheral neuron activity. The compounds of the present invention are generally derivatives of N-phenylanthranilic acid or 2-benzimidazolone.

According to one aspect of the present invention there is provided a method of modulating (preferably opening) a voltage-dependent potassium channel, the method comprising administering to the subject in need thereof a therapeutically effective amount of a compound selected from the group consisting of N-phenylanthranilic acid, a N-phenylanthranilic acid derivative, 2-benzimidazolone, a 2-benzimidazolone derivative, and a pharmaceutically acceptable salt, a prodrug or a metabolite thereof.

Preferably, the compound has a general Formula I or II (vide infra). Further preferably, the voltage-dependent potassium channels modulated are KCNQ2 channels, KCNQ3 channels and/or KCNQ2/3 channels.

According to another aspect of the present invention there is provided a method of depressing cortical and/or peripheral neuron activity, the method comprising administering to the subject in need thereof a therapeutically effective amount of a compound selected from the group consisting of N-phenylanthranilic acid, a N-phenylanthranilic acid derivative, 2-benzimidazolone and a 2-benzimidazolone derivative, or a pharmaceutically acceptable salt thereof.

Preferably, the compound has a general Formula I or II (vide infra).

According to still another aspect of the present invention there is provided a method of treating neuropathic pain, the method comprising administering to the subject in need thereof a therapeutically effective amount of a compound selected from the group consisting of N-phenylanthranilic acid, a N-phenylanthranilic acid derivative, 2-benzimidazolone and a 2-benzimidazolone derivative, or a pharmaceutically acceptable salt thereof.

Preferably, the compound has a general Formula I or II (vide infra).

According to yet another aspect of the present invention there is provided a pharmaceutical composition for the treatment or prevention of a condition or disorder, e.g., in the central or peripheral nervous system, in which modulating a voltage-dependent potassium channel and/or depressing a cortical and/or peripheral neuron activity is beneficial, the pharmaceutical composition comprising, as an active ingredient, a compound selected from the group consisting of N-phenylanthranilic acid, a N-phenylanthranilic acid derivative, 2-benzimidazolone and a 2-benzimidazolone derivative, or a pharmaceutically acceptable salt thereof.

Preferably, the compound has the general Formula I or II (vide infra). Further preferably, the voltage-dependent potassium channels modulated are KCNQ2 channels, KCNQ3 channels and/or KCNQ2/3 channels.

According to the present invention, general Formulae I and II are:

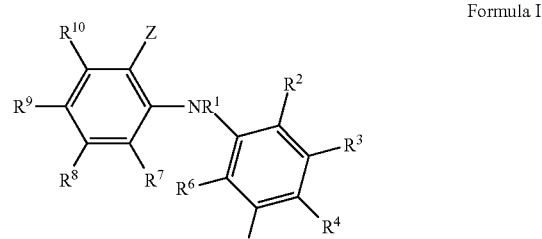

Formula I

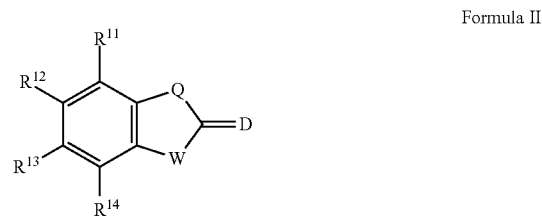

Formula II wherein:
Z is an A-G(=K)—X—Y group,
and wherein
A is alkyl or absent;
G is selected from the group consisting of C, S and PRa;
K is selected from the group consisting of O and S;
X is selected from the group consisting of NRb, O, S or absent; and
Y is selected from the group consisting of hydrogen, alkyl, hydroxyalkyl, cycloalkyl, aryl and a polyalkylene glycol residue,
each of Q and W is independently selected from the group consisting of NRc, O, S and CRdRe;
D is selected from the group consisting of O and S;
$R^1$ is selected from the group consisting of hydrogen, alkyl, cycloalkyl or aryl;

Each of $R^2$, $R^3$, $R^4$, $R^5$, $R^6$, $R^7$, $R^8$, $R^9$, $R^{10}$, $R^{11}$, $R^{12}$, $R^{13}$, $R^{14}$, Rd and Re is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$ or, alternatively, at least two of $R^2$, $R^3$, $R^4$, $R^5$ and $R^6$, of $R^7$, $R^8$, $R^9$ and $R^{10}$ and/or of $R^{11}$, $R^{12}$, $R^{13}$ and $R^{14}$ form a five- or six-membered aromatic, heteroaromatic, alicyclic or heteroalicyclic ring;

$R^{15}$ and $R^{16}$ are each independently selected from the group consisting of hydrogen, alkyl, cycloalkyl, aryl, carbonyl and sulfonyl, or, alternatively $R^{15}$ and $R^{16}$ form a five- or six-member heteroalicyclic ring;

and each of Ra, Rb and Rc is independently selected from the group consisting of alkyl, cycloalkyl and aryl.

According to one embodiment of the present invention, a compound of the present invention has the general Formula I. When a compound of the present invention is of the general Formula I, then Y is preferably selected from the group consisting of hydroxyalkyl and a polyalkylene glycol residue. Preferably, the polyalkylene glycol residue has a general formula III:

$$[(CH_2)m\text{-}O]n\text{-}R^{17} \qquad \text{Formula III}$$

wherein each of m and n is independently an integer of 1-10; and $R^{17}$ is hydrogen, alkyl, cycloalkyl or aryl. According to a feature of the present invention, each of $R^2$, $R^3$, $R^4$, $R^5$ and $R^6$ is independently selected from the group consisting of hydrogen, alkyl, halo and trihaloalkyl and each of $R^7$, $R^8$, $R^9$ and $R^{10}$ is hydrogen.

According to another embodiment of the present invention, a compound of the present invention has the general Formula II. When a compound of the present invention has the general Formula II, then preferably Q and W are each substituted or unsubstituted nitrogen (NRc, wherein Rc is not hydrogen); and D is oxygen (O), and even more preferably Q is a substituted nitrogen.

According to a preferred embodiment of the present invention, compounds are selected from the group consisting of compounds 1, 2, 3, 4, 5, 6, 7, 8, 9 and 10:

1
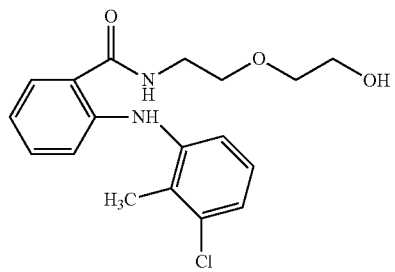

2
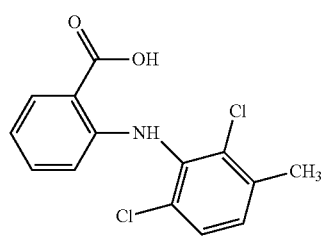

3
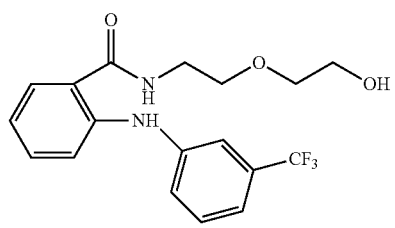

4
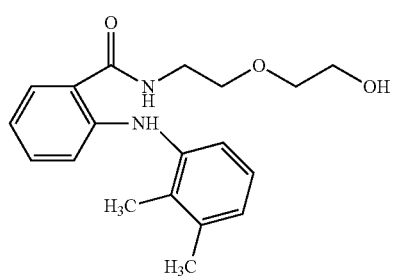

5
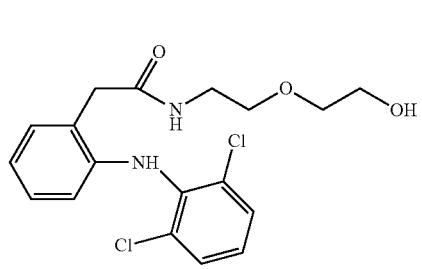

6
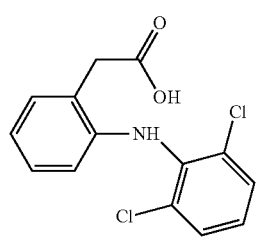

7
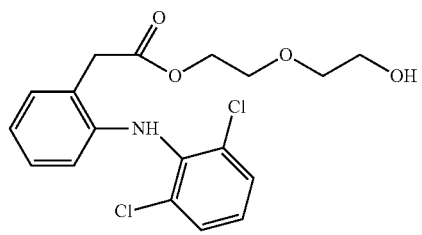

8
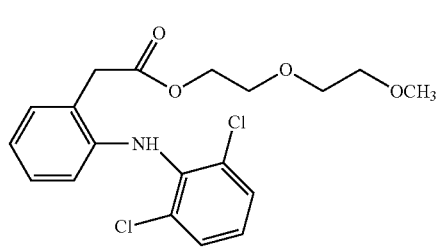

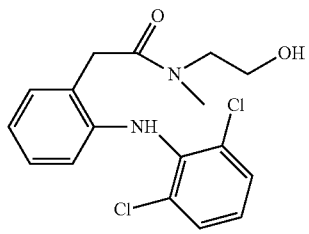

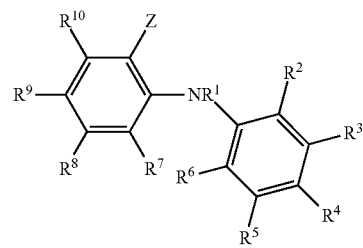

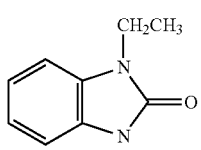

and pharmaceutically acceptable salts, prodrugs and metabolites thereof.

According to a feature of the present invention modulating of the voltage-dependent potassium channel and/or depressing the cortical neuron activity is for a treatment of a condition or disorder selected from the group of disorders consisting of epilepsy, ischemic stroke, migraine, ataxia, myokymia, neurogenic pain, neuropathic pain Alzheimer's disease, Parkinson's disease, age-related memory loss, learning deficiencies, bipolar disorder, trigeminal neuralgia, spasticity, mood disorder, psychotic disorder, brain tumor, hearing and vision loss, anxiety and a motor neuron disease.

According to a feature of the present invention, administering of the a compound of the present invention is effected intranasally, subcutaneously, intravenously, intramuscularly, parenterally, orally, topically, intradermally, bronchially, buccally, sublingually, supositorially and mucosally.

According to a feature of the present invention, a compound of the present invention forms a part of a pharmaceutical composition, which further includes a pharmaceutically acceptable carrier.

According to a feature of the present invention, a pharmaceutical composition of the present invention further comprises an agent selected from the group consisting of an anti-bacterial agent, an antioxidant, a buffering agent, a bulking agent, an anti-inflammatory agent, an anti-viral agent, a chemotherapeutic agent and an anti-histamine.

According to a feature of the present invention, a pharmaceutically composition is packaged in a packaging material and identified in print, in or on the packaging material, for use in the treatment or prevention of a condition or disorder associated with altered activity of a voltage-dependent potassium channel. Preferably such a condition or disorder is selected from the group consisting of epilepsy, ischemic stroke, migraine, ataxia, myokymia, neurogenic pain, neuropathic pain Alzheimer's disease, Parkinson's disease, age-related memory loss, learning deficiencies, bipolar disorder, trigeminal neuralgia, spasticity, mood disorder, psychotic disorder, brain tumor, hearing and vision loss, anxiety and a motor neuron disease.

According to still another aspect of the present invention there is provided a novel compound having a general Formula IV:

a pharmaceutically acceptable salt, prodrug or metabolite thereof,
wherein:
Z is an A-G(=K)—X—Y group,
and wherein:
A is alkyl or absent;
G is selected from the group consisting of O, S and substituted or unsubstituted phosphor (PRa);
K is selected from the group consisting of oxygen (O) and sulfur (S);
X is selected from the group consisting of substituted or unsubstituted nitrogen (NRb), sulfur or absent; and
Y is selected from the group consisting of hydroxyalkyl and a polyalkylene glycol residue;
$R^1$ is selected from the group consisting of hydrogen, alkyl, cycloalkyl or aryl;
each of $R^2$, $R^3$, $R^4$, $R^5$, $R^6$, $R^7$, $R^8$, $R^9$ and $R^{10}$ is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$, or, alternatively, at least two of $R^2$, $R^3$, $R^4$, $R^5$ and/or $R^6$, of $R^7$, $R^8$, $R^9$ and $R^{10}$ form a five- or six-membered aromatic, heteroaromatic, alicyclic or heteroalicyclic ring;
$R^{15}$ and $R^{16}$ are each independently selected from the group consisting of hydrogen, alkyl, cycloalkyl, aryl, carbonyl and sulfonyl, or, alternatively $R^{15}$ and $R^{16}$ form a five- or six-member heteroalicyclic ring; and
each of Ra and Rb is independently selected from the group consisting of hydrogen, alkyl, cycloalkyl and aryl.

According to a feature of the present invention, when Y is a polyalkylene residue, the polyalkylene glycol residue does not comprise a —$ONO_2$ group or an anti-oxidant residue.

According to another feature of the present invention, when Y is hydroxyalkyl and X is NRb, then Rb is selected from the group consisting of alkyl, cycloalkyl and aryl and the hydroxyalkyl is not hydroxypropyl.

According to a feature of the present invention, the polyalkylene glycol residue of a novel compound of the present invention has a general formula V:

$$[(CH_2)m-O]n-R^{17}$$ Formula V wherein each of m and n is independently an integer of 1-10 and $R^{17}$ is hydrogen, alkyl, cycloalkyl or aryl.

According to an additional feature, for a novel compound of the present invention, G is carbon, K is oxygen, each of $R^2$, $R^3$, $R^4$, $R^5$ and $R^6$ is independently selected from the group consisting of hydrogen, alkyl, halo and trihaloalkyl; and each of $R^7$, $R^8$, $R^9$ and $R^{10}$ is hydrogen.

According to a preferred embodiment of the present invention, a novel compound of the present invention is selected from the group consisting of compounds 3, 4, 5, 6, and 9:

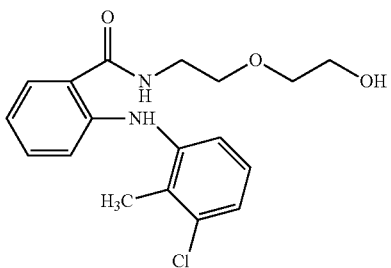

3

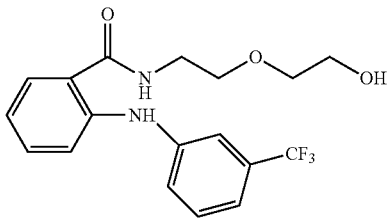

4

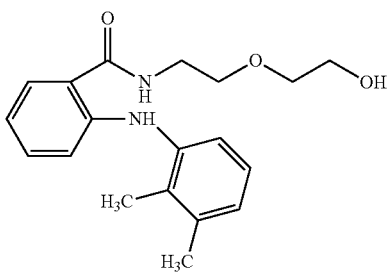

5

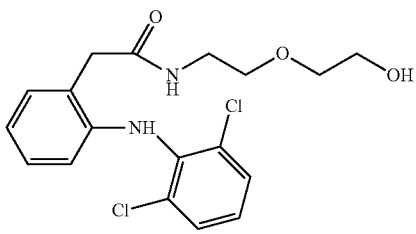

6

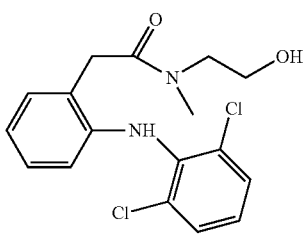

9 and pharmaceutically acceptable salts, prodrugs and metabolites thereof.

According to an additional aspect of the present invention there is provided a pharmaceutical composition comprising, as an active ingredient, a compound of the present invention having a general formula IV.

According to a feature of the present invention there is provided a pharmaceutical composition, comprising, as an active ingredient, any one of the compounds 3, 4, 5, 6, and/or 9.

According to yet another aspect of the present invention there is provided a method for the synthesis of a compound of formula IV. The method comprises obtaining a N-phenylanthranilic acid or a derivative thereof; and reacting the N-phenylanthranilic acid or the derivative thereof with a hydroxy-alkyl or a polyalkylene glycol terminating with a reactive group, which is capable of forming an ester bond with the N-phenylanthranilic acid or the derivative thereof.

The ester bond is preferably selected from the group consisting of a carboxylic amide bond, a carboxylic thioester bond, a S-carboxy thioester bond and a S-carboxy amide bond, whereas the reactive group is preferably selected from the group consisting of hydroxy, amine and thiohydroxy.

The N-phenylanthranilic acid or the derivative thereof preferably has a general Formula VI:

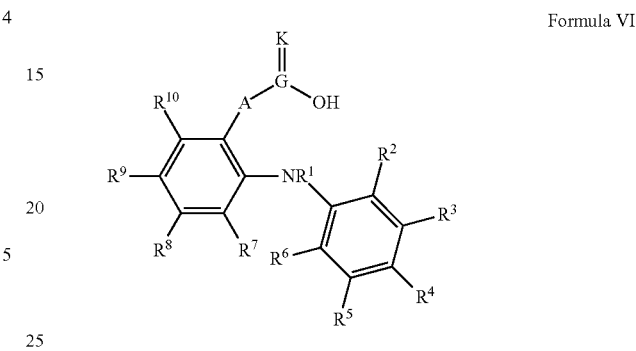

Formula VI wherein,

A, G, K, $R^1$, $R^2$, $R^3$, $R^4$, $R^5$, $R^6$, $R^7$, $R^8$, $R^9$ and $R^{10}$ are as described hereinabove.

Preferably, G is carbon; K is oxygen; each of $R^2$, $R^3$, $R^4$, $R^5$ and $R^6$ is independently selected from the group consisting of hydrogen, alkyl, halo and trihaloalkyl; and each of $R^7$, $R^8$, $R^9$ and $R^{10}$ is hydrogen.

The polyalkylene glycol terminating with the reactive group preferably has a general formula VII:

$$V\text{—}[(CH_2)m\text{-}O]n\text{-}R^{17}$$  Formula VII wherein:

V is amine or thiohydroxy;

each of m and n is independently an integer of 1-10; and $R^{17}$ is hydrogen, alkyl, cycloalkyl or aryl.

The present invention successfully addresses the shortcomings of the presently known configurations by providing compounds that act to modulate potassium channels and/or depress cortical activity, are generally available and/or are relatively easy to synthesize. Some of the compounds provided are already known in the art of pharmacology whereby some of the compounds are novel compounds that were designed so as to exhibit superior performance.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the embodiments of the present invention only, and are presented in the cause of providing what is believed to be the most useful and readily understood description of the principles and conceptual aspects of the invention. In this regard, no attempt is made to show details of the invention in more detail than is necessary for a fundamental understanding of the invention, the results taken with the drawings making apparent to those skilled in the art how the invention may be embodied in practice.

In the drawings:

Figure 2:
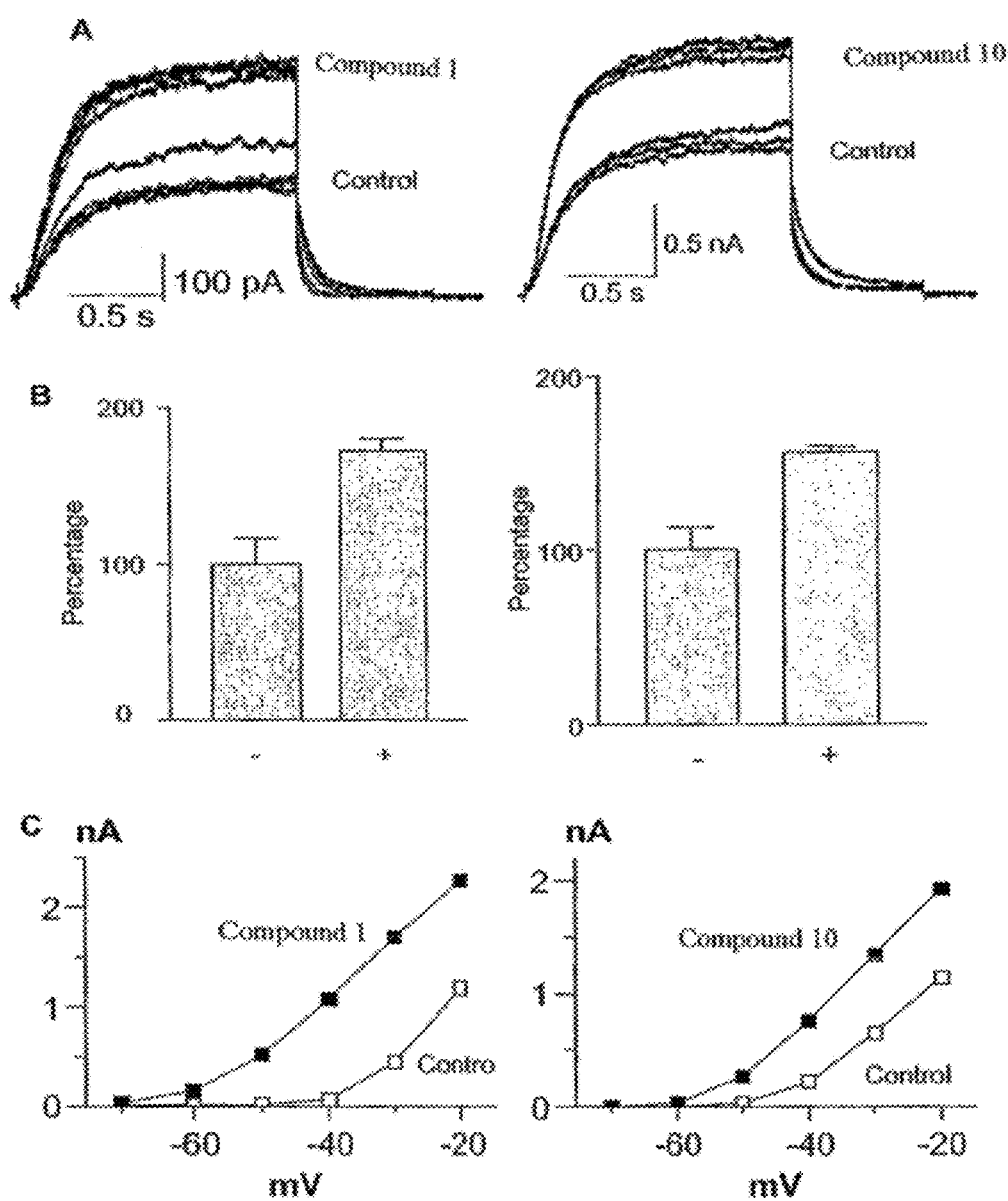
Figure 4:
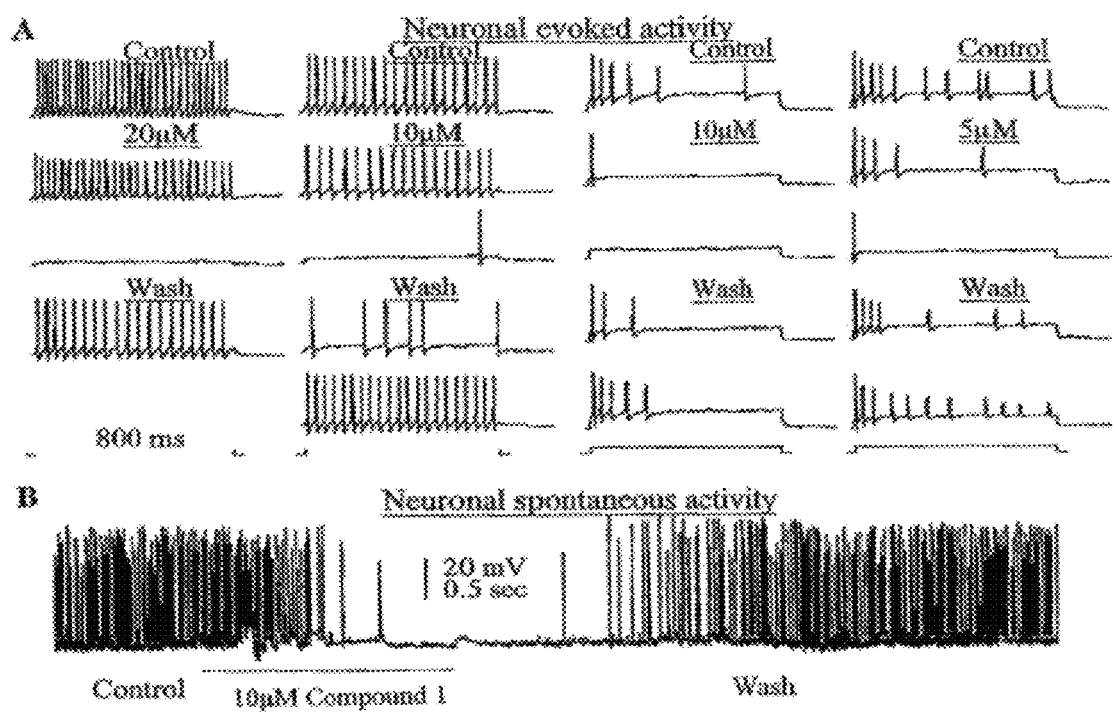
Figure 5:
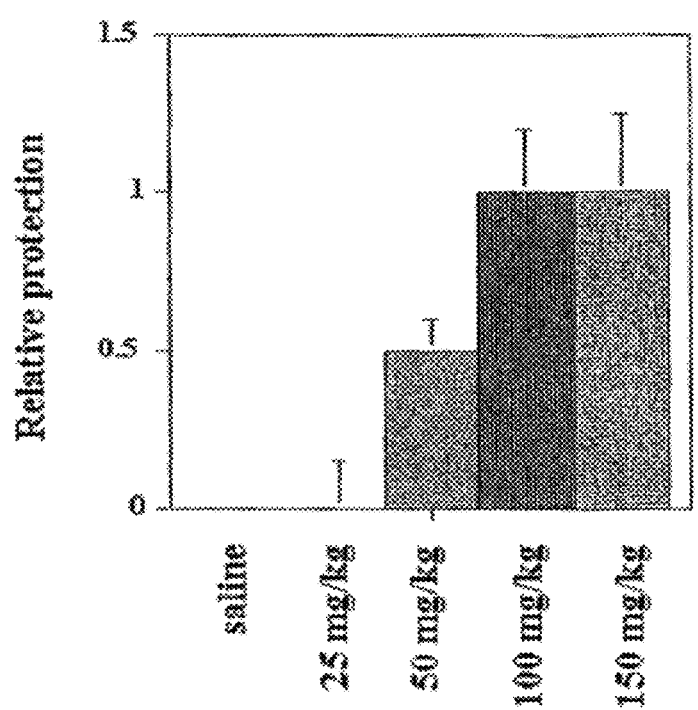
Figure 6A:
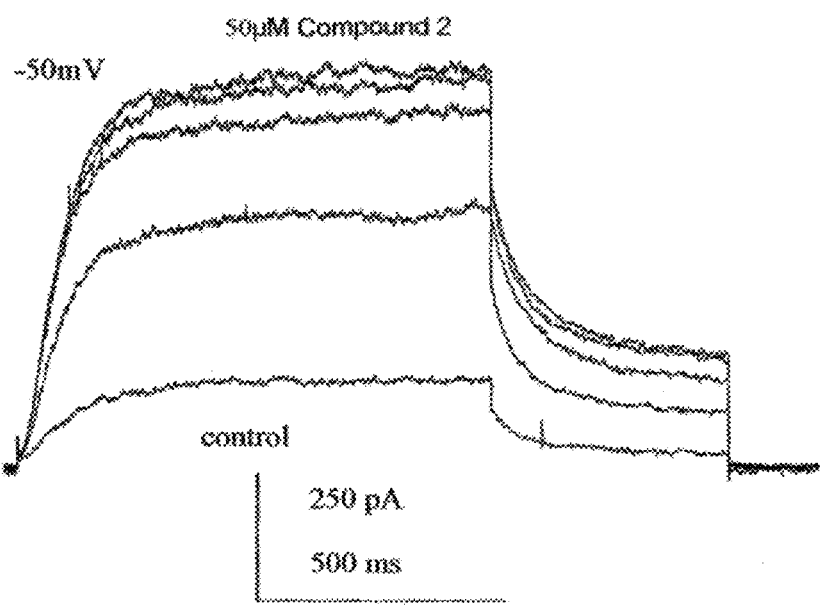
Figure 6B:
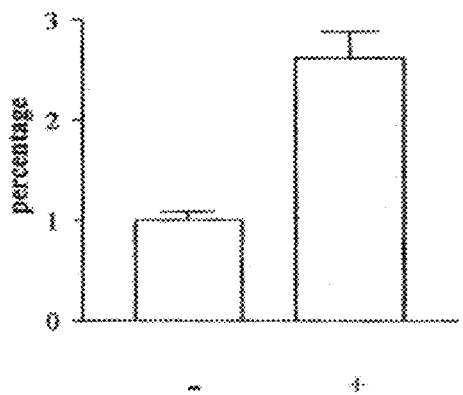
Figure 6C:
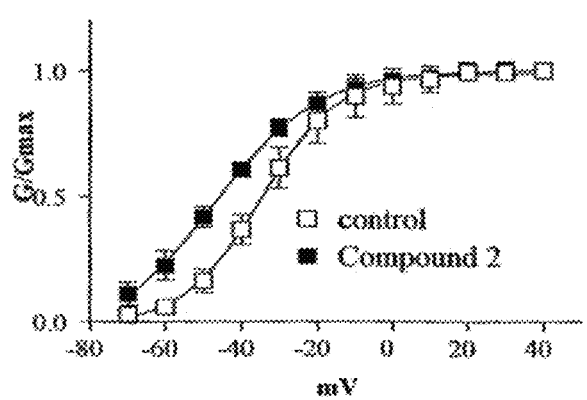
Figure 9A:
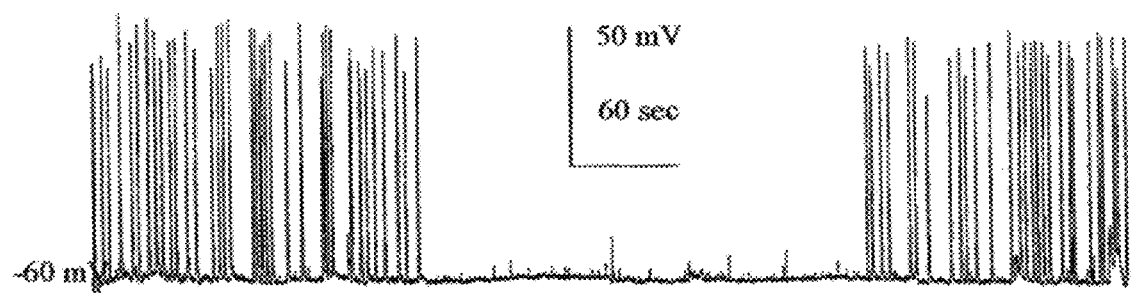
Figure 9B:
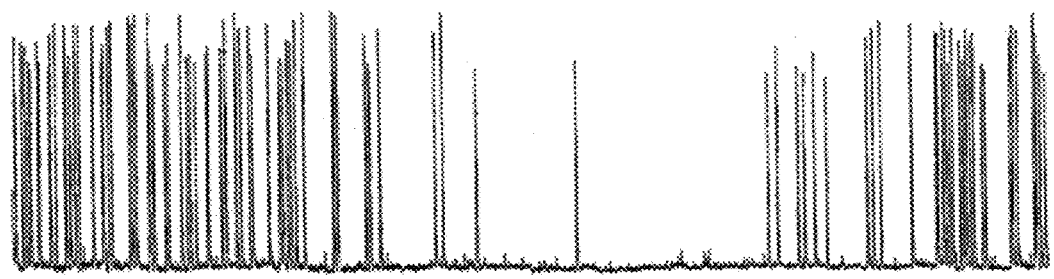
Figure 9C:
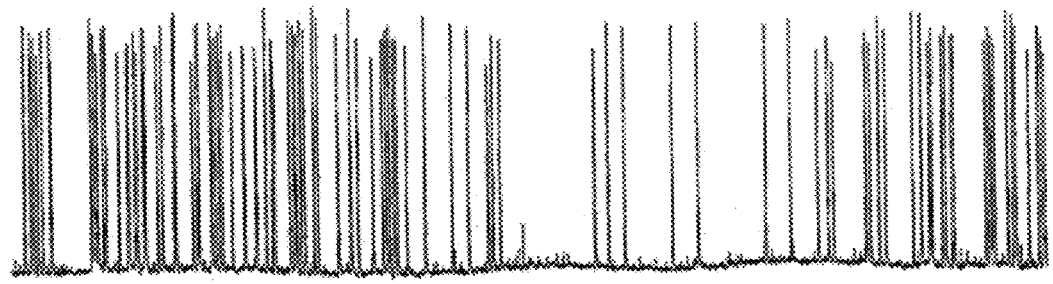
Figure 11A:
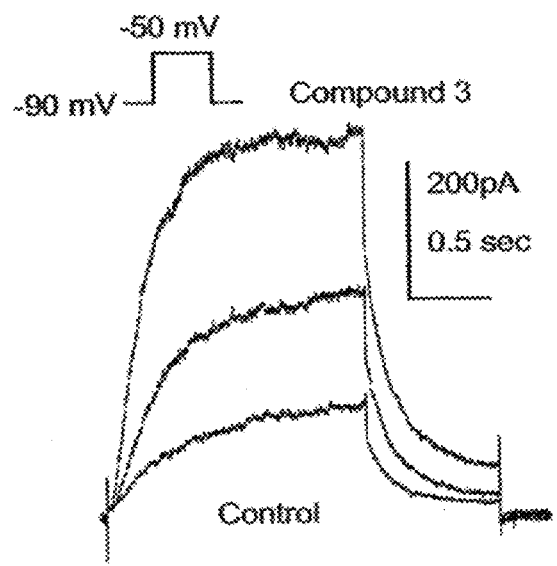
Figure 11B:
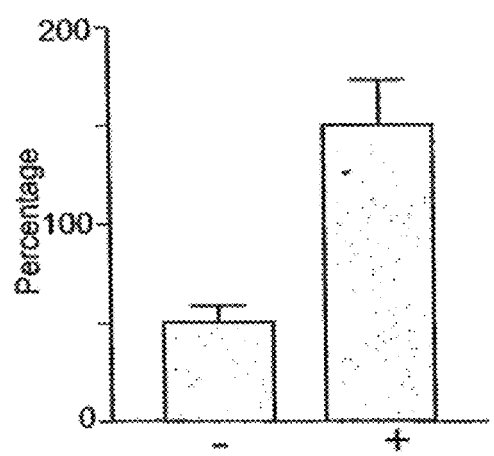
Figure 12A:
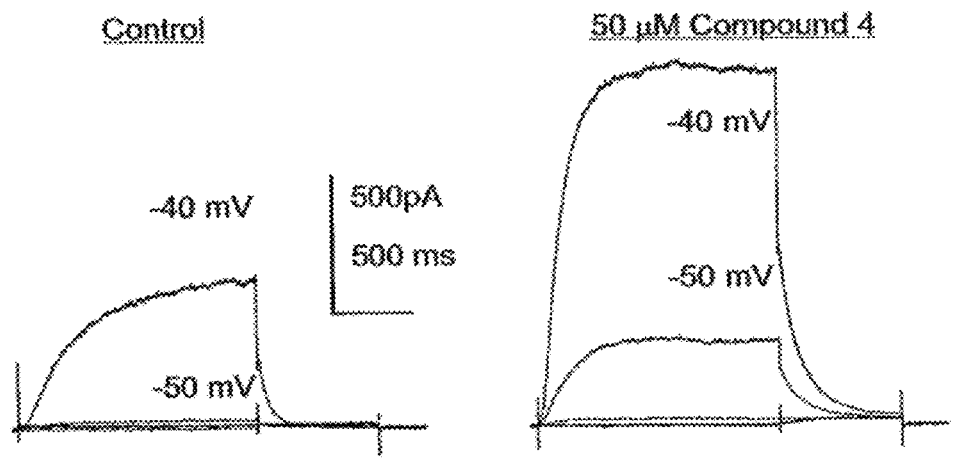
Figure 12B:
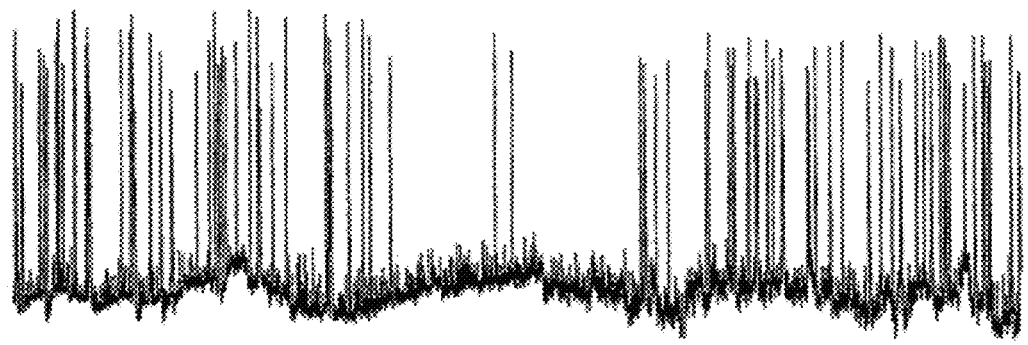
Figure 12C:
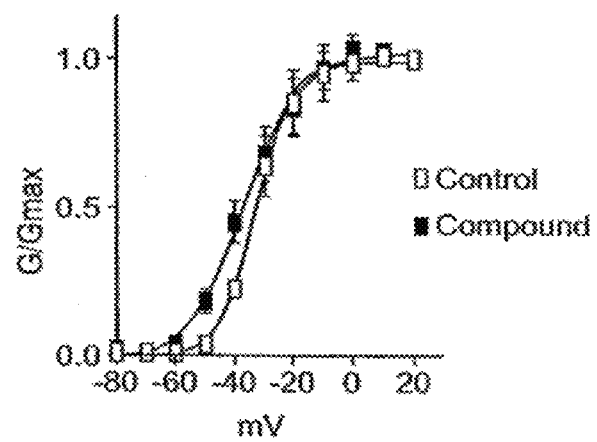
Figure 13:
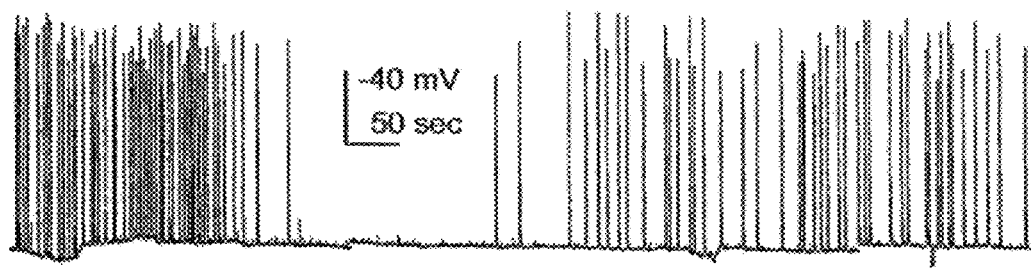
Figure 15A:
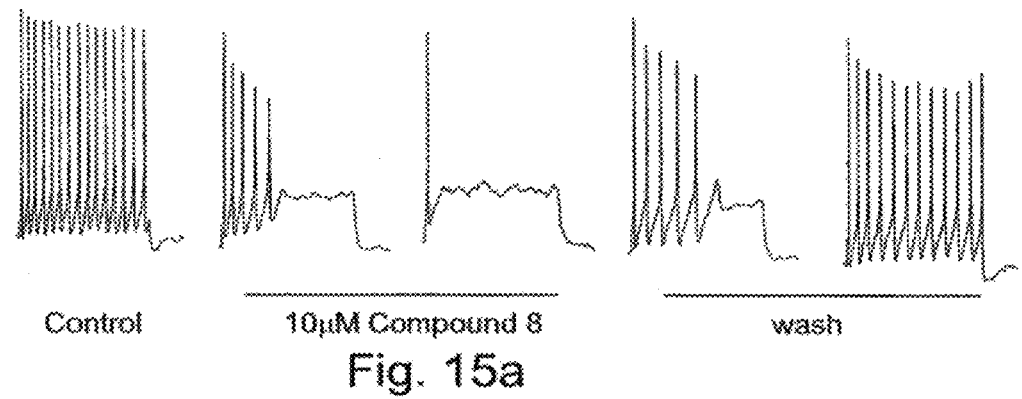
Figure 15B:
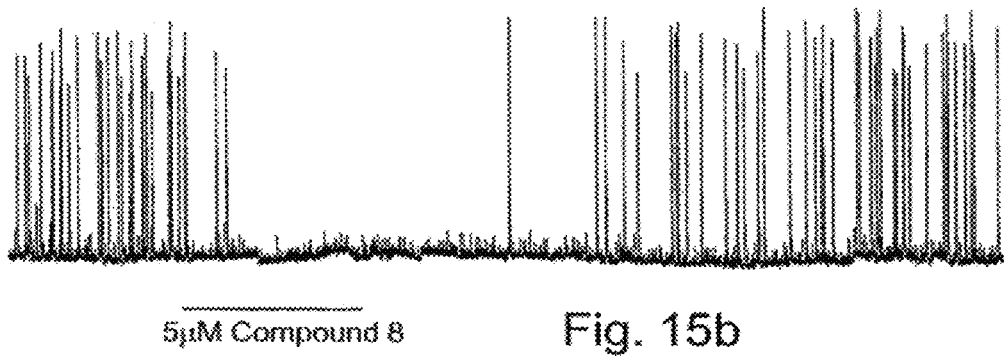
Figure 18:
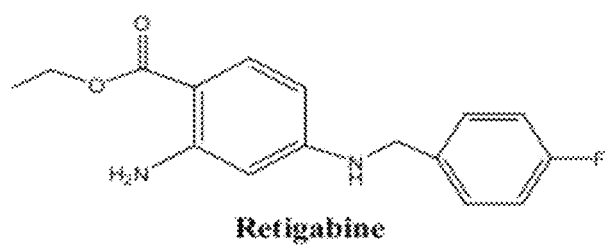
Figure 20:
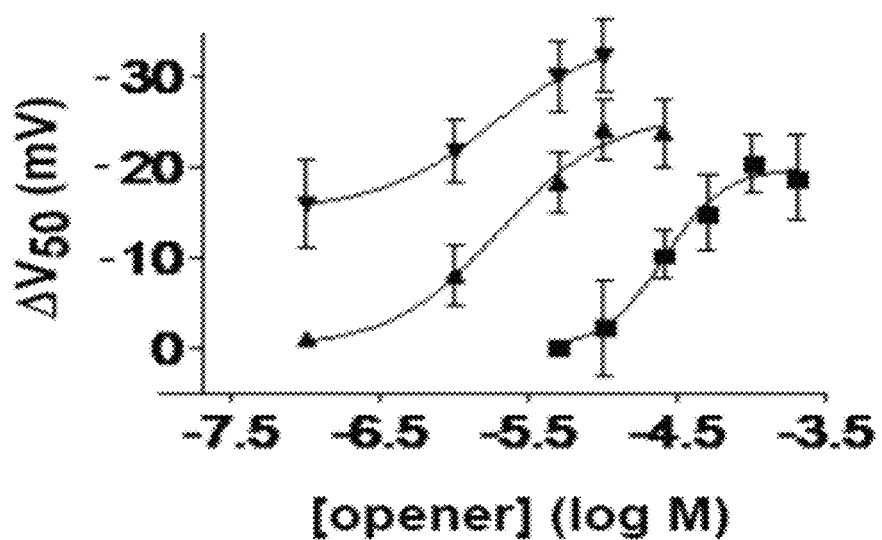
Figure 21:
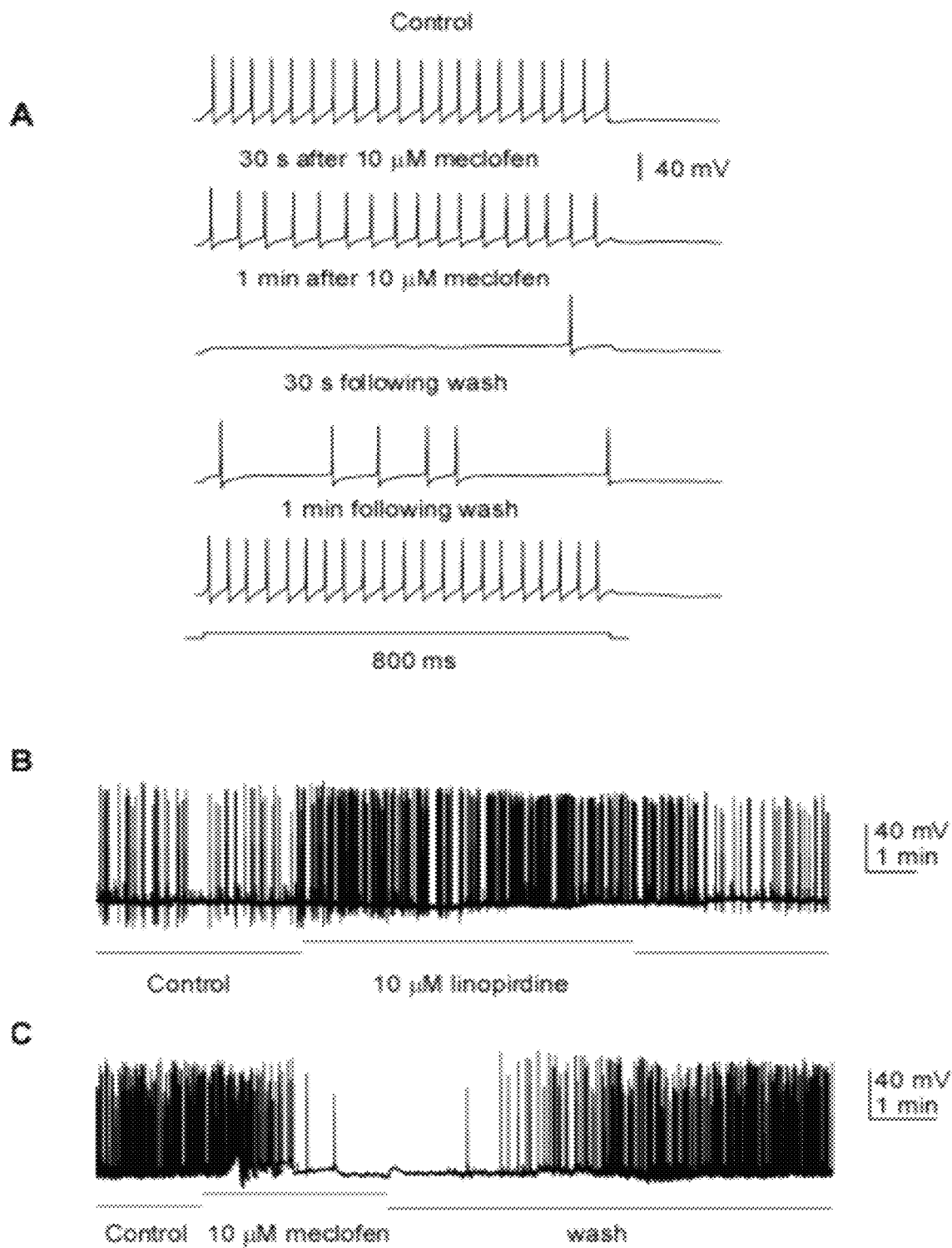
Figure 22:
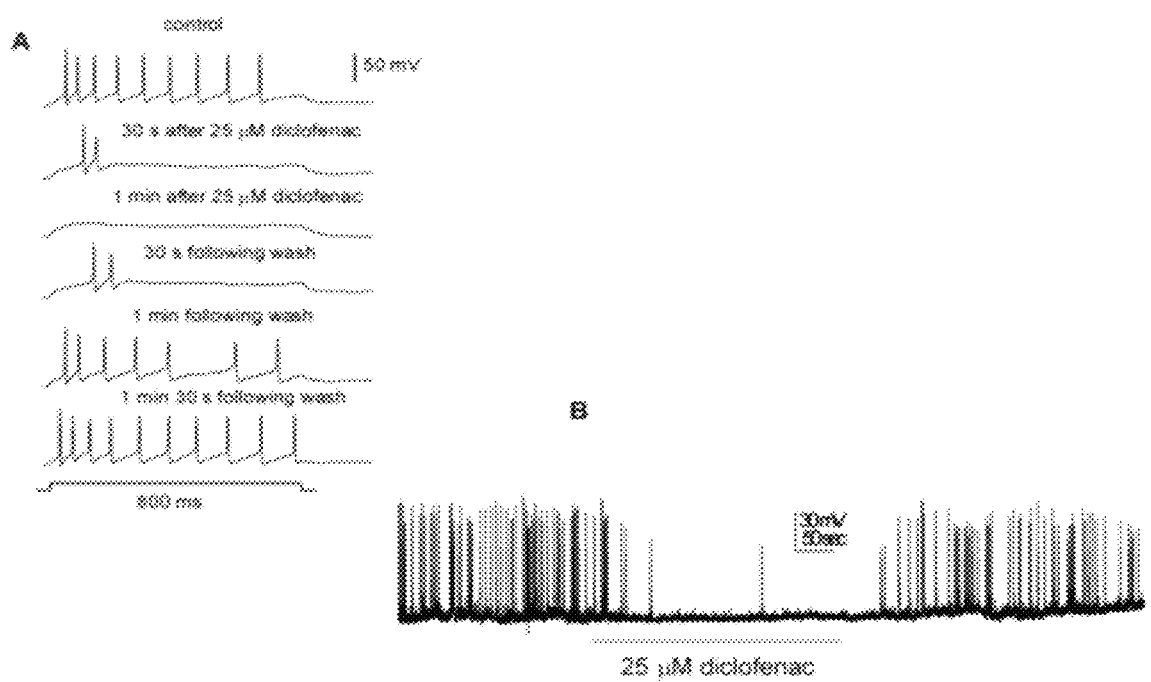
Figure 24:
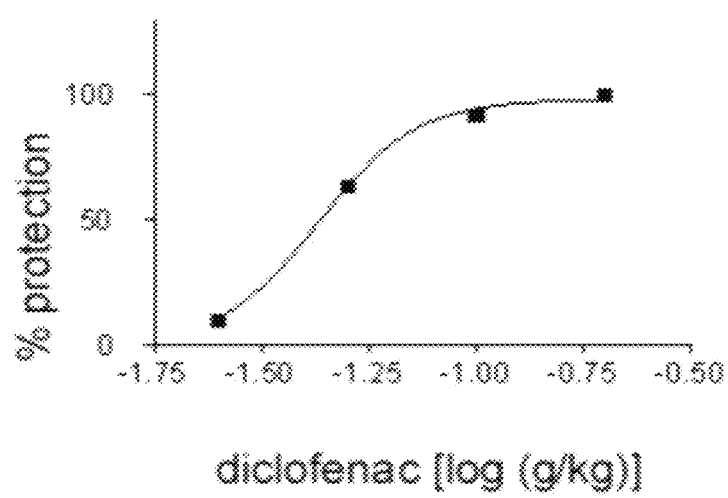
Figure 25:
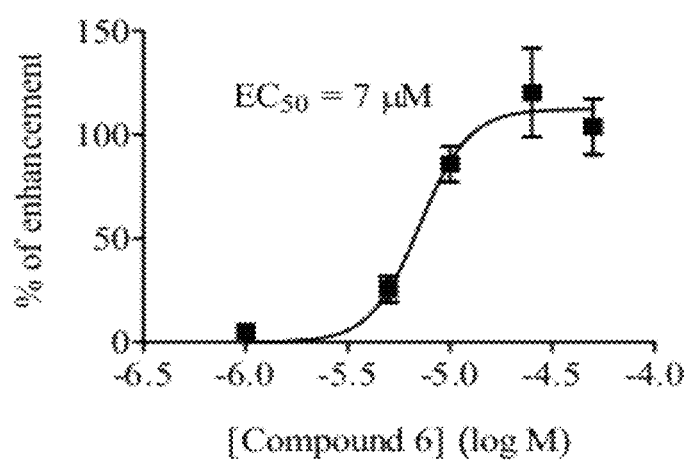
Figure 26:
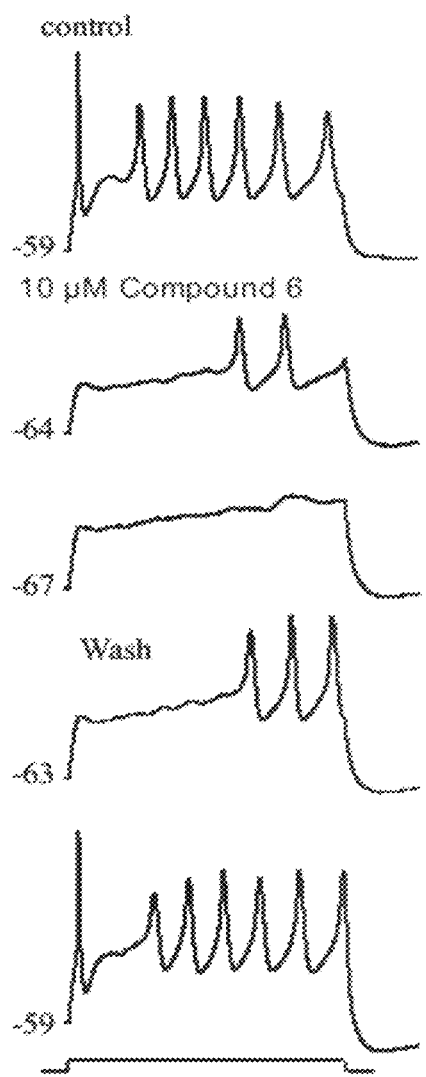
Figure 27:
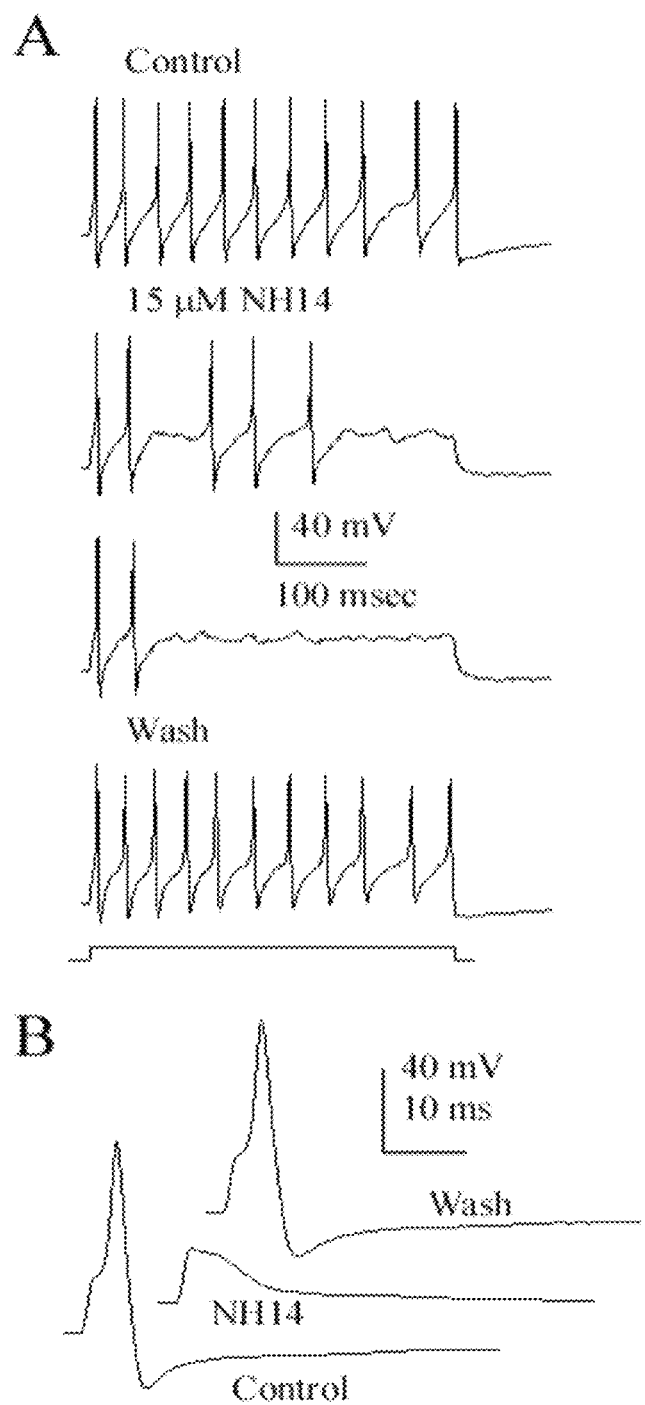
Figure 28:
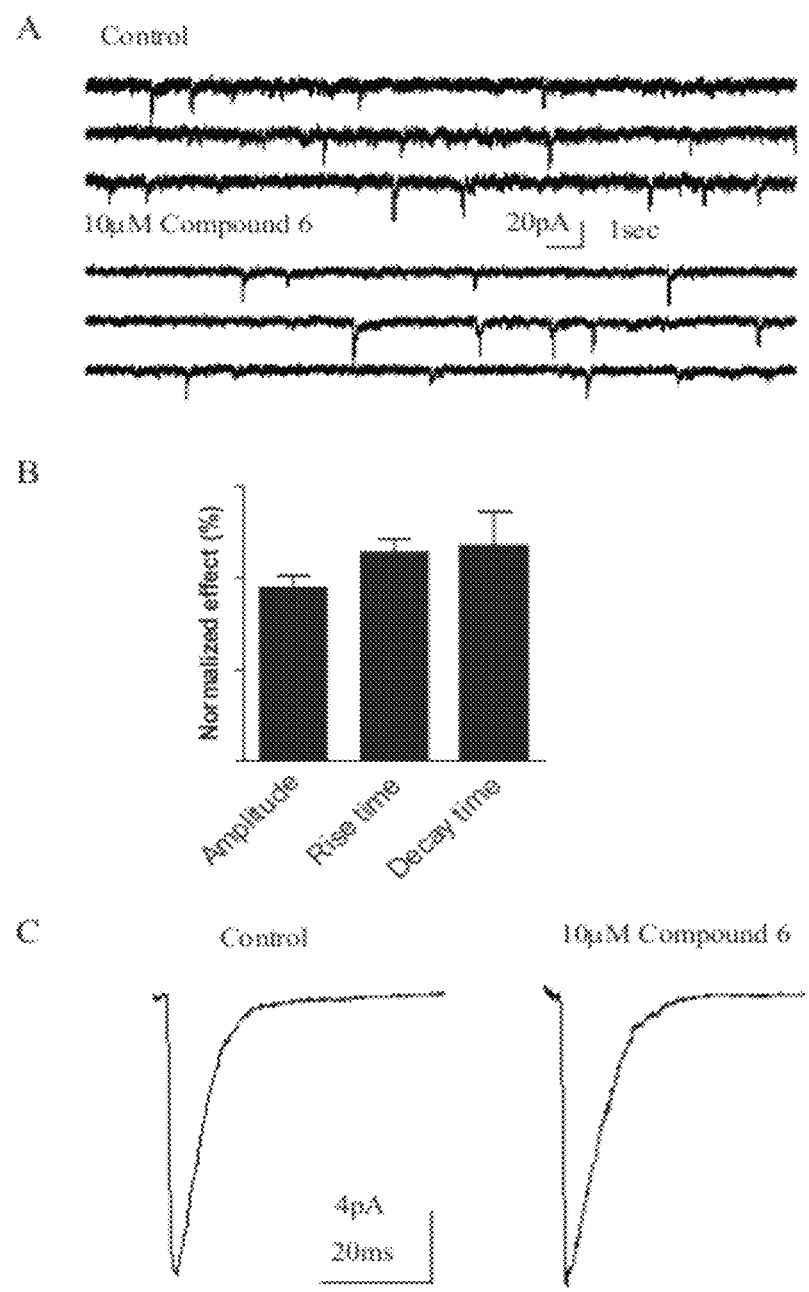
Figure 29:
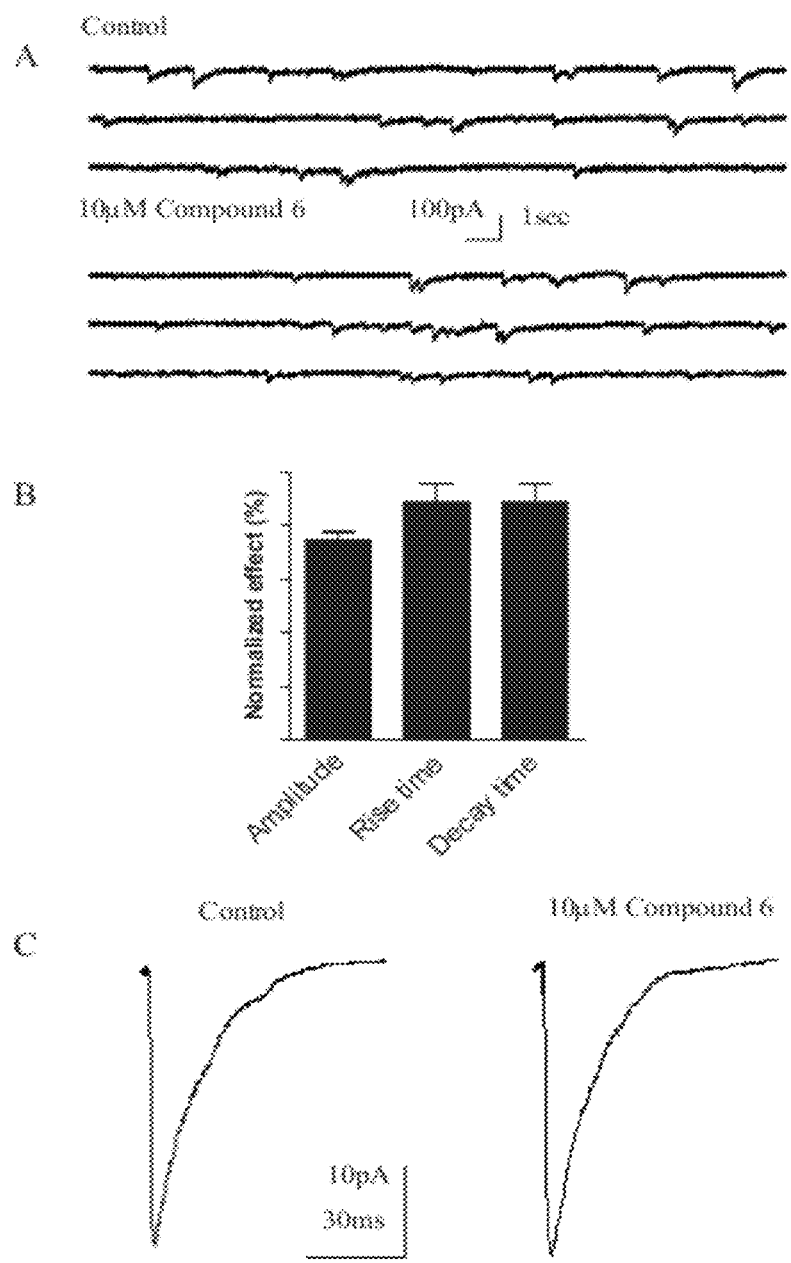
Figure 31:
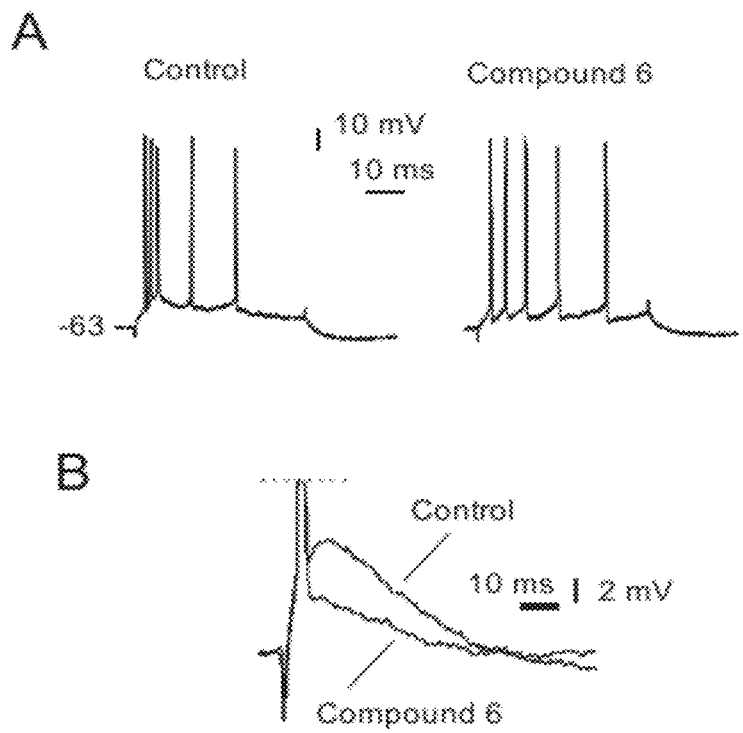
Figure 32:
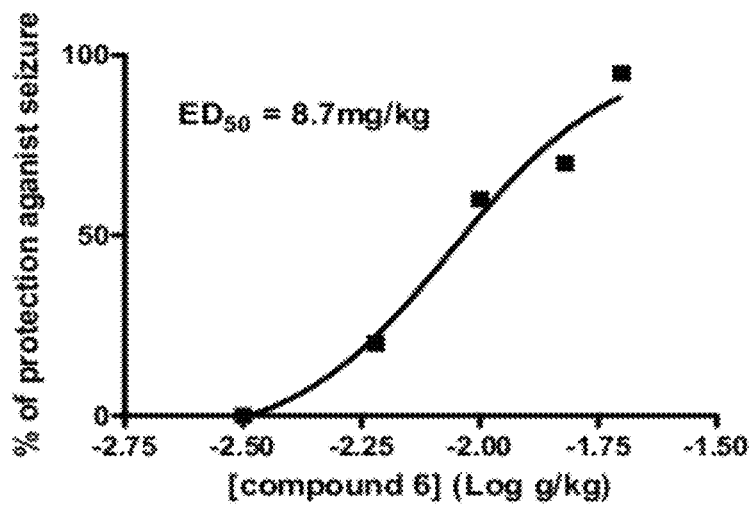
Figure 33:
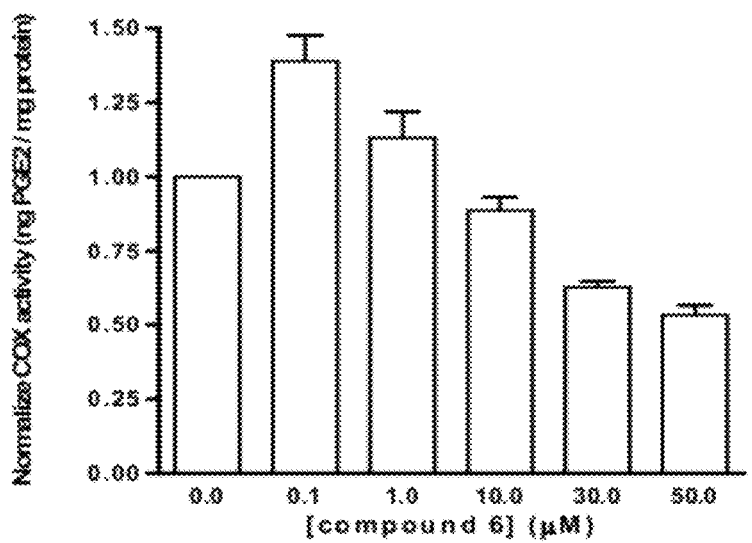
Figure 34:
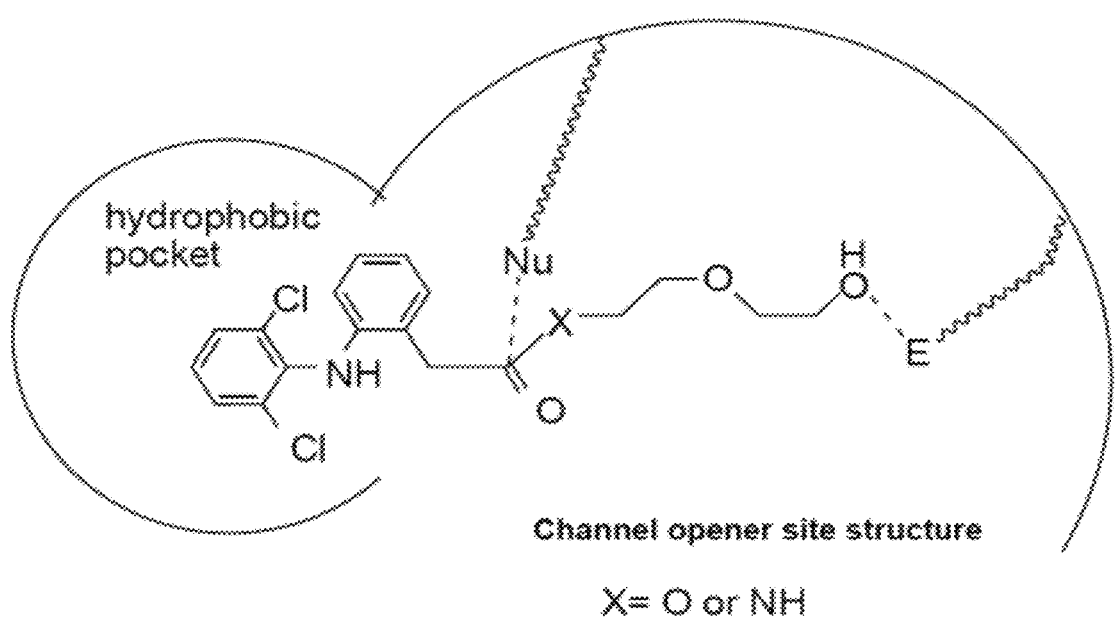

FIGS. 1A-1D present results demonstrating the leftward shift of the activation curve induced by meclofenamic acid (Compound 1) and 1-EBIO (Compound 10) in CHO cells;

FIGS. 2A-2C present results demonstrating the increase of KCNQ2/3 current induced by meclofenamic acid (Compound 1) and 1-EBIO (Compound 10) in CHO cells;

FIGS. 3A-3E present results demonstrating the effect of meclofenamic acid (Compound 1) and 1-EBIO (Compound 10) on the deactivation process of KCNQ2/3 channels in CHO cells;

FIGS. 4A-4B present results demonstrating the depression of neuronal activity by meclofenamic acid (Compound 1);

FIG. 5 presents results demonstrating the neuroprotective effect of meclofenamic acid (Compound 1) from electroshock-induced seizures in adult mice;

FIGS. 6A-6C present results demonstrating the enhancement of the KCNQ2/3 current by diclofenac (Compound 2);

FIGS. 7A-7C present results demonstrating the effects of Compound 6 on KCNQ2/3 currents;

FIGS. 8A-8B present results demonstrating the inhibition of evoked neuronal activity by compound 6;

FIGS. 9A-9C present results demonstrating the inhibitory effect of different concentrations of Compound 6 on spontaneous neuronal activity;

FIGS. 10A-10C present results demonstrating the effects of Compound 5 on neuronal activity and on KCNQ2/3 current;

FIGS. 11A-11B present results demonstrating the increase in KCNQ2/3 current induced by the presence of Compound 3;

FIGS. 12A-12C present results demonstrating the effects of Compound 4 on neuronal activity and on KCNQ2/3 current;

FIG. 13 present results demonstrating the effect of Compound 9 on spontaneous neuronal activity;

FIGS. 14A-14D present results demonstrating the effects of Compound 7 on KCNQ2/3 channels and neuronal activity;

FIGS. 15A-15B present results demonstrating the effect of Compound 8 on evoked and spontaneous neuronal activity;

FIGS. 16A-16D present results demonstrating the selectivity of meclofenamic acid (Compound 1) towards KCNQ2 and KCNQ3 homomeric channels, expressed in CHO cells;

FIG. 17 presents the chemical structures of Compounds 1-10;

FIG. 18 presents the chemical structure of Retigabine;

FIGS. 19A-C present results demonstrating the effects of meclofenamic acid (Compound 1) on KCNQ2/3 currents in Xenopus oocyte expression system;

FIG. 20 presents comparative plots demonstrating the dose-response curve of meclofenamic acid (Compound 1, squares), retigabine (upward triangles) and co-application thereof (downward triangles) opener activity for KCNQ2/Q3 channels;

FIGS. 21A-21C present additional results demonstrating the depression of neuronal activity by meclofenamic acid (Compound 1);

FIGS. 22A-22B present results demonstrating the depression of neuronal activity by diclofenac (Compound 2);

FIGS. 23A-23D present results demonstrating the enhancement of the M-current in rat cortical neurons by meclofenamic acid (Compound 1);

FIG. 24 presents results demonstrating the dose-dependent protecting effect of diclofenac on seizures induced in ICR adult mice by the MES test;

FIG. 25 presents results demonstrating the concentration-dependent effect of Compound 6 on KCNQ2/3 currents;

FIG. 26 presents results demonstrating the effect of Compound 6 on F11 cells neuronal activity;

FIGS. 27A-27B present results demonstrating the effect of Compound 6 on the neuronal activity of DRG cells;

FIGS. 28A-28C present results demonstrating the effect of Compound 6 on the mEPSCs of hippocampal neurons;

FIGS. 29A-29C present results demonstrating the effect of Compound 6 on the mIPSCs of hippocampal neurons;

FIGS. 30A-30E present results demonstrating the effect of Compound 6 on spontaneous neuron burst activity;

FIGS. 31A-31B present results demonstrating the effect of Compound 6 on neuronal activity and ADP (after depolarization) of rat hippocampal slices;

FIG. 32 presents results demonstrating the dose-dependent protecting effect of Compound 6 on seizures induced in ICR adult mice by the MES test;

FIG. 33 present results showing the effect of various concentrations of Compound 6 on COX activity; and FIG. 34 presents a schematic illustration of the various functionalities of preferred channel openers according to the present invention.

DESCRIPTION OF THE PREFERRED EMBODIMENTS

The present invention provides compounds that, inter alia, are generally useful in the modulation of potassium ion flux through voltage-dependent potassium channels, specifically the KCNQ2, KCNQ3 and/or KCNQ2/3 channels and/or useful in depressing cortical and/or peripheral neuron activity.

The principles and uses of the present invention may be better understood with reference to the Examples and accompanying descriptions. Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

According to one aspect of the present invention there is provided a method of modulating (preferably opening) a voltage-dependent potassium channel in a subject in need thereof, the method comprising administering to the subject a therapeutically effective amount of N-phenylanthranilic acid, a N-phenylanthranilic acid derivative, 2-benzimidazolone, a 2-benzimidazolone derivative, or a pharmaceutically acceptable salt, prodrug or metabolite thereof.

As used herein, the term "derivative" describes the result of chemically altering, modifying or changing a molecule or a portion thereof, such that it maintains its original functionality in at least one respect.

The voltage-dependent potassium channels modulated are preferably KCNQ2 channels, KCNQ3 channels and/or KCNQ2/3 channels.

According to another aspect of the present invention there is provided a method of depressing cortical neuron activity, the method comprising administering to the subject in need thereof a therapeutically effective amount of the compound N-phenylanthranilic acid, a N-phenylanthranilic acid derivative, 2-benzimidazolone, a 2-benzimidazolone derivative, or a pharmaceutically acceptable salt, prodrug or metabolite thereof.

According to another aspect of the present invention there is provided a method of treating neuropathic pain, the method comprising administering to the subject in need thereof a therapeutically effective amount of the compound N-phenylanthranilic acid, a N-phenylanthranilic acid derivative, 2-benzimidazolone, a 2-benzimidazolone derivative, or a pharmaceutically acceptable salt, prodrug or metabolite thereof.

According to yet another aspect of the present invention there is provided a pharmaceutical composition for the treatment or prevention of conditions or disorders in which modulating a voltage-dependent potassium channel and/or depressing a cortical and/or peripheral neuron activity is beneficial, the pharmaceutical composition comprising, as an active ingredient, the compound N-phenylanthranilic acid, a N-phenylanthranilic acid derivative, 2-benzimidazolone, a 2-benzimidazolone derivative, or a pharmaceutically acceptable salt, prodrug or metabolite thereof, and a pharmaceutically acceptable carrier.

Preferably, the compound utilized in any of the aspects described above has the general Formula I or II. Further preferably, the voltage-dependent potassium channels modulated are KCNQ2 channels, KCNQ3 channels and/or KCNQ2/3 channels.

According to the present invention general Formulae I and II are:

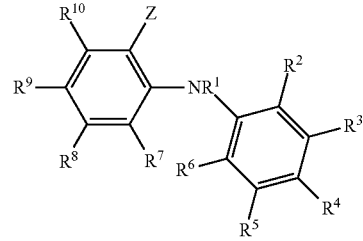

Formula I

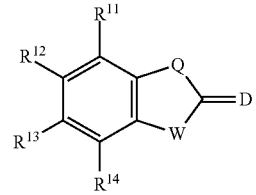

Formula II or a pharmaceutically acceptable salt, prodrug or metabolite thereof, wherein:

Z is an A-G(=K)—X—Y group, and wherein

A is alkyl or absent;

G is selected from the group consisting of carbon (C), sulfur (S) and substituted or unsubstituted phosphor (PRa);

K is selected from the group consisting of oxygen (O) and sulfur;

X is selected from the group consisting of substituted or unsubstituted nitrogen (NRb), oxygen, sulfur or absent; and Y is selected from the group consisting of hydrogen, alkyl, hydroxyalkyl, cycloalkyl, aryl and a polyalkylene glycol residue, each of Q and W is independently selected from the group consisting of substituted or unsubstituted nitrogen (NRc), oxygen, sulfur and carbon (CRdRe);

D is selected from the group consisting of oxygen and sulfur;

$R^1$ is selected from the group consisting of hydrogen, alkyl, cycloalkyl or aryl;

Each of $R^2$, $R^3$, $R^4$, $R^5$, $R^6$, $R^7$, $R^8$, $R^9$, $R^{10}$, $R^{11}$, $R^{12}$, $R^{13}$, $R^{14}$, Rd and Re is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$ or, alternatively, at least two of $R^2$, $R^3$, $R^4$, $R^5$ and $R^6$, of $R^7$, $R^8$, $R^9$ and $R^{10}$ and/or of $R^{11}$, $R^{12}$, $R^{13}$ and $R^{14}$ form a five- or six-membered aromatic, heteroaromatic, alicyclic or heteroalicyclic ring;

$R^{15}$ and $R^{16}$ are each independently selected from the group consisting of hydrogen, alkyl, cycloalkyl, aryl, carbonyl and sulfonyl, or, alternatively $R^{15}$ and $R^{16}$ form a five- or six-member heteroalicyclic ring; and each of Ra, Rb and Rc is independently hydrogen, alkyl, cycloalkyl or aryl.

According to one embodiment of the present invention, a compound of the present invention has the general Formula I. When a compound of the present invention is of the general Formula I, then Y is preferably selected from the group consisting of hydroxyalkyl and a polyalkylene glycol residue.

Preferably, the polyalkylene glycol residue has a general formula III:

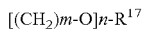  Formula III wherein each of m and n is independently an integer of 1-10 and $R^{17}$ is hydrogen, alkyl, cycloalkyl or aryl. According to a feature of the present invention, each of $R^2$, $R^3$, $R^4$, $R^5$ and $R^6$ is independently selected from the group consisting of hydrogen, alkyl, halo and trihaloalkyl and each of $R^7$, $R^8$, $R^9$ and $R^{10}$ is hydrogen.

According to another embodiment of the present invention, a compound of the present invention has the general Formula II. When a compound of the present invention has the general Formula II, then preferably Q and W are each substituted or unsubstituted nitrogen; and D is oxygen, and even more preferably Q is a substituted nitrogen.

According to a preferred embodiment of the present invention, compounds are selected from the group consisting of:

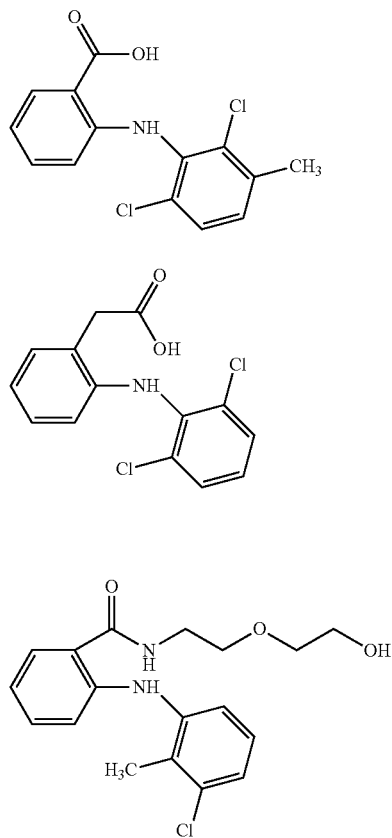

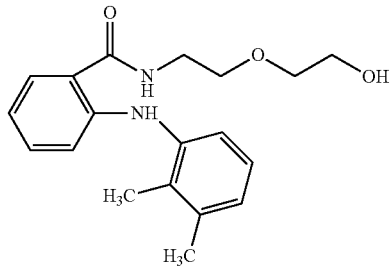

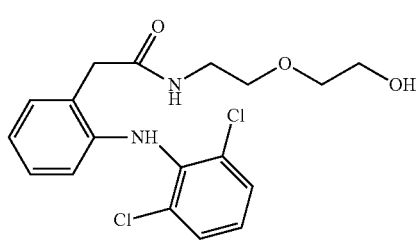

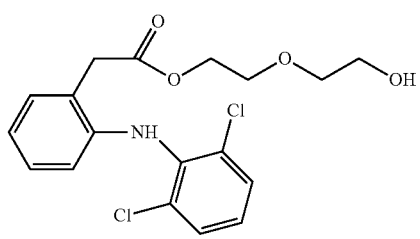

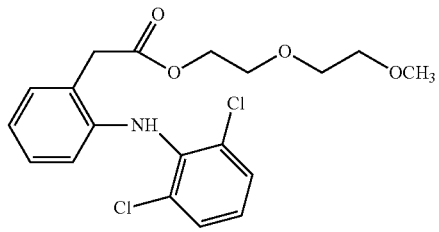

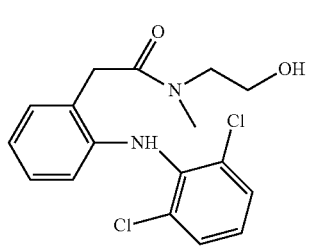

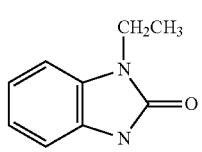

and pharmaceutically acceptable salts, prodrugs and metabolites thereof.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

By "treating" or is meant that a compound of the present invention is used as a therapeutic, prophylactic or ameliorative agent, whether with respect to a pathology, condition or disorder, a symptom thereof or an effect thereof.

There are many pathologies, conditions and disorders that are associated with defective potassium channel functioning. Just as other potassium channel modulating compounds, the compounds of the present invention are for use within the framework of a treatment for pathologies, conditions and disorders associated with defective potassium modulation, so as to treat, ameliorate, prevent, inhibit, or limit the effects of the conditions and pathologies in animals including humans.

More particularly, the invention provides compounds, compositions and methods that are useful in the treatment of central or peripheral nervous system disorders (e.g., ischemic stroke, migraine, ataxia, Parkinson's disease, bipolar disorders, trigeminal neuralgia, spasticity, mood disorders, brain tumors, psychotic disorders, myokymia, neurogenic pain, neuropathic pain, seizures, epilepsy, hearing and vision loss, Alzheimer's disease, Parkinson's disease, age-related memory loss, learning deficiencies, anxiety and motor neuron diseases), and as neuroprotective agents (e.g., to prevent stroke and the like). Compounds of the invention have use as agents for treating convulsive states, for example that following grand mal, petit mal, psychomotor epilepsy or focal seizure. The compounds of the invention are also useful in treating disease states such as gastroesophogeal reflux disorder and gastrointestinal hypomotility disorders. Other pathologies and conditions that compounds of the present invention are useful in treating are listed in, for example, U.S. Pat. Nos. 6,348,486; 6,117,900; 6,589,986 and 6,593,349 and U.S. patent application Ser. Nos. 10/022,579; 10/075,703; 10/075,522; 10/114,148; 10/160,582 and 10/312,123, all of which are hereby incorporated by reference.

As voltage dependent potassium channels are found in all animal species, the compounds of the present invention are pharmaceutically effective when administered to subjects who are members of all animal species, including monkeys, dogs, cats, mice, rats, farm animals, livestock, fish and most importantly humans.

As used herein, the terms "opening" and "activating" are used interchangeably and refer to the partial or full activation of a KCNQ channel by a compound, which leads to an increase in ion flux either into or out of a cell in which a KCNQ channel is found.

Techniques for formulation and administration of compounds as medicaments may be found in "Remington's Pharmaceutical Sciences," Mack Publishing Co., Easton, Pa., latest edition, which is incorporated herein by reference and are also discussed hereinfurther.

The compounds of the present invention are preferably configured to cross the blood brain barrier so as to allow many different types of dosage forms. Nevertheless, pharmaceutical compositions of the present invention may be provided to an individual in need of treatment (whether therapeutic, prophylactic or ameliorative) by a variety of preferred routes, such as subcutaneous, topical, oral, intraperitoneal, intradermal, intravenous, intranasal, bronchial, buccal, sublingual, suppository, intramuscular, oral, rectal, transmucosal, intestinal or parenteral delivery, including topical, intra-arterial, intramuscular, subcutaneous and intramedullary injections as well as intrathecal, direct intraventricular, intravenous, intraperitoneal, intranasal, or intraocular injections.

Alternatively, one may administer a composition of the present invention in a local rather than systemic manner, for example, via injection of the composition directly into an organ, often in a depot or slow release formulation, such as described below.

"A therapeutically (or pharmaceutically) effective amount" means an amount of active ingredient needed to achieve the desired outcome, which is generally to prevent, alleviate or ameliorate a condition or symptoms of the condition. Determination of a therapeutically effective amount is within the capability of those skilled in the art, especially in light of the detailed disclosure provided herein.

"Compound of the invention," as used herein refers to N-phenylanthranilic acids, 2-benzimidazolones, and derivatives thereof or any combination thereof, preferably such as those having Formula I or II. In any of the aspects of the present invention, the compound can be also utilized as a pharmaceutically acceptable salt, a prodrug, a and a solvate form, as these terms are defined herein.

A metabolite of the compound can further be utilized according to the present invention.

As used herein, the term "metabolite" describes the actual active moiety of the compound which is formed as a result of metabolitic processes that occur in vivo upon administration of the compound.

The term "solvate" refers to a complex of variable stoichiometry (e.g., di-, tri-, tetra-, penta-, hexa-, and so on), which is formed by a solute (the compound of present invention) and a solvent, whereby the solvent does not interfere with the biological activity of the solute. The term "hydrate" refers to a solvate, as defined hereinabove, where the solvent is water.

The compounds may be true solvates or may merely retain adventitious solvent, or be a mixture of solvate and adventitious solvent.

The phrase "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral (i.e., non-ionized) form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions in vivo to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

As used herein in the specification and in the claims section that follows, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it means that the group, in this case the alkyl group, may contain 1 carbon atom, 2 carbon atoms, 3 carbon atoms, etc., up to and including 20 carbon atoms. More preferably, it is a medium size alkyl having 1 to 10 carbon atoms. Most preferably, it is a lower alkyl having 1 to 4 carbon atoms. The alkyl group may be substituted or unsubstituted. When substituted, the substituent group can be, for example, cycloalkyl, aryl, heteroaryl, heteroalicyclic, hydroxy, alkoxy, aryloxy, thiohydroxy, thioalkoxy, thioaryloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfonamido, trihalomethanesulfonamido, silyl, guanyl, guanidino, ureido, amino or $NR_aR_b$, wherein $R_a$ and $R_b$ are each independently hydrogen, alkyl, cycloalkyl, aryl, carbonyl, sulfonyl, trihalomethysulfonyl and, combined, a five- or six-member heteroalicyclic ring.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, aryl, heteroaryl, heteroalicyclic, hydroxy, alkoxy, aryloxy, thiohydroxy, thioalkoxy, thioaryloxy, cyano, halo, carbonyl, thiocarbonyl, C-carboxy, O-carboxy, O-carbamyl, N-carbamyl, C-amido, N-amido, nitro, amino and $NR_aR_b$ as defined above.

An "alkenyl" group refers to an alkyl group which consists of at least two carbon atoms and at least one carbon-carbon double bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, halo, trihalomethyl, alkyl, hydroxy, alkoxy, aryloxy, thiohydroxy, thiocarbonyl, C-carboxy, O-carboxy, O-carbamyl, N-carbamyl, O-thiocarbamyl, N-thiocarbamyl, C-amido, N-amido, sulfinyl, sulfonyl, amino and $NR_aR_b$ as defined above.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, cycloalkyl, halo, trihalomethyl, hydroxy, alkoxy, aryloxy, thiohydroxy, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino or $NR_aR_b$ as defined above.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, alkyl, cycloalkyl, aryl, heteroaryl, halo, trihalomethyl, hydroxy, alkoxy, aryloxy, thiohydroxy, thioalkoxy, thioaryloxy, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, C-amido, N-amido, amino and $NR_aR_b$ as defined above.

A "hydroxy" group refers to an —OH group.

An "azido" group refers to a —N=N group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

An "thioaryloxy" group refers to both an —S-aryl and an —S-heteroaryl group, as defined herein.

A "carbonyl" group refers to a —C(=O)—R' group, where R' is hydrogen, alkyl, cycloalkyl, aryl, heteroaryl (bonded through a ring carbon) or heteroalicyclic (bonded through a ring carbon) as defined herein.

An "aldehyde" group refers to a carbonyl group, where R' is hydrogen.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

A "carboxylic acid" group refers to a C-carboxyl group in which R' is hydrogen.

A "halo" group refers to fluorine, chlorine, bromine or iodine.

A "trihalomethyl" group refers to a —$CX_3$ group wherein X is a halo group as defined herein.

A "trihalomethanesulfonyl" group refers to an $X_3CS(=O)_2$— group wherein X is a halo group as defined herein.

A "sulfinyl" group refers to an —S(=O)—R' group, where R' is as defined herein.

A "sulfonyl" group refers to an —$S(=O)_2$—R' group, where R' is as defined herein.

An "S-sulfonamido" group refers to a —S(=O)2-NR'R" group, with R' is as defined herein and R" is as defined for R'.

An "N-sulfonamido" group refers to an R'$S(=O)_2$—NR" group, where R' and R" are as defined herein.

A "trihalomethanesulfonamido" group refers to an $X_3CS(=O)_2NR'$— group, where R' and X are as defined herein.

An "O-carbamyl" group refers to an —OC(=O)—NR'R" group, where R' and R" are as defined herein.

An "N-carbamyl" group refers to an R'OC(=O)—NR"— group, where R' and R" are as defined herein.

An "O-thiocarbamyl" group refers to an —OC(=S)—NR'R" group, where R' and R" are as defined herein.

An "N-thiocarbamyl" group refers to an R"OC(=S)NR'— group, where R' and R" are as defined herein.

An "amino" group refers to an —$NH_2$ group.

A "C-amido" group refers to a —C(=O)—NR'R" group, where R' and R" are as defined herein.

An "N-amido" group refers to an R'C(=O)—NR" group, where R' and R" are as defined herein.

A "quaternary ammonium" group refers to an —NHR'R"+ group, wherein R' and R" are independently alkyl, cycloalkyl, aryl or heteroaryl.

An "ureido" group refers to an —NR'C(=O)—NR"R'" group, where R' and R" are as defined herein and R'" is defined as either R' or R".

A "guanidino" group refers to an —R'NC(=N)—NR"R'" group, where R', R" and R'" are as defined herein.

A "guanyl" group refers to an R'R"NC(=N)— group, where R' and R" are as defined herein.

A "nitro" group refers to an —$NO_2$ group.

A "cyano" group refers to a —C≡N group.

A "silyl" group refers to a —SiR'R"R'", where R', R" and R'" are as defined herein.

According to a preferred embodiment, the compound of the present invention has the general Formula I. In one preferred embodiment Y is selected from the group consisting of hydroxyalkyl and a polyalkylene glycol residue. Preferably such a polyalkylene glycol residue has a general formula III:

[($CH_2$)$_m$-O]$_n$-$R^{17}$    Formula III wherein each of m and n is independently an integer of 1-10; and $R^{17}$ is hydrogen, alkyl, cycloalkyl or aryl. Preferably, G is carbon, K is oxygen, each of $R^2$, $R^3$, $R^4$, $R^5$ and $R^6$ is independently selected from the group consisting of hydrogen, alkyl, halo and trihaloalkyl; and each of $R^7$, $R^8$, $R^9$ and $R^{10}$ is hydrogen.

According to a different preferred embodiment, the compound of the present invention has the general Formula II. When a compound of the present invention has the general Formula II, then preferably Q and W are each substituted or unsubstituted nitrogen; and D is oxygen, and even more preferably Q is a substituted nitrogen.

The term "substituted nitrogen", as used herein, described a —NRb- group or a —NRc- group, where Rb and Rc are alkyl, cycloalkyl or aryl, as these terms are defined herein.

Preferred compounds of the present invention include the compounds:

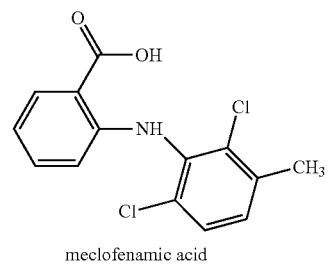

meclofenamic acid

1

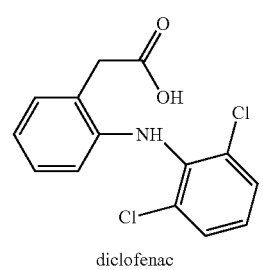

diclofenac

2

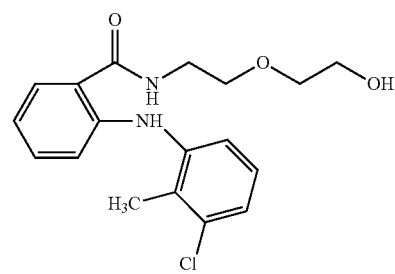

3

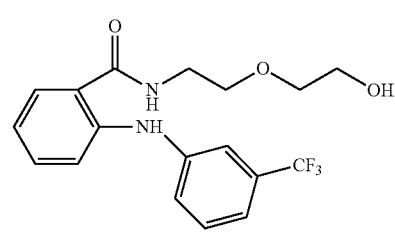

4

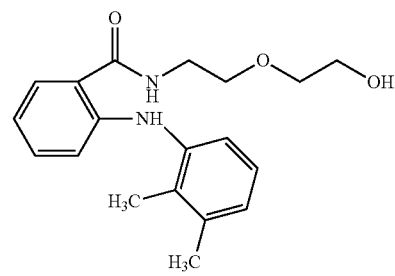

5

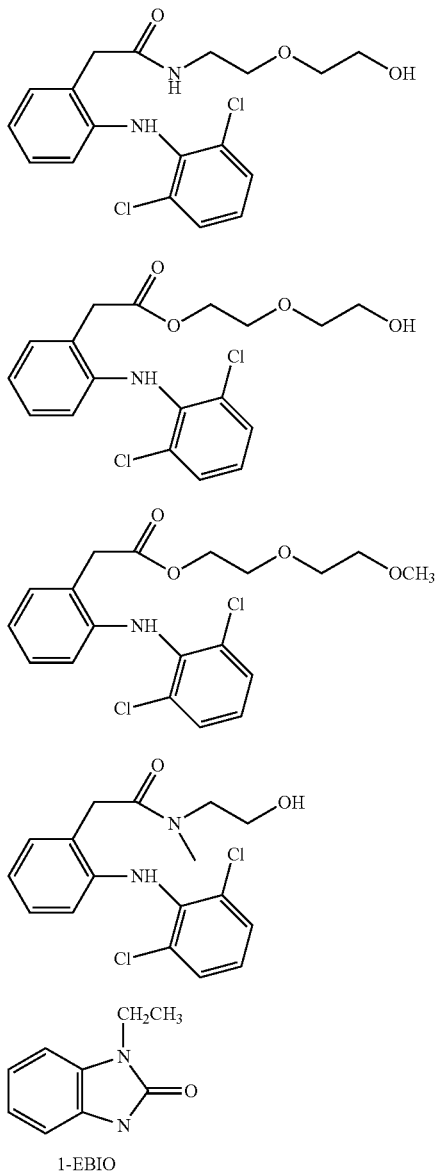

and pharmaceutically acceptable salts thereof.

As is detailed hereinafter, the exceptional modulating effect of meclofenamic acid (also referred to herein interchangeably as meclofenac or Compound 1) and of diclofenac (Compound 2) has been demonstrated. However, since these and other N-phenylanthranilic acids are typically characterized by relatively low blood brain permeability, the present inventors have designed and successfully practiced novel derivatives of N-phenylanthranilic acids with improved brain permeability.

Thus, according to another aspect of the present invention, there are provided novel compounds, which are useful in context of the present invention. These novel compounds are generally derivatives of N-phenylanthranilic acid which have a hydroxyalkyl and a polyalkylene glycol residue covalently attached thereto. The hydroxyalkyl and a polyalkylene glycol residue generally increase the ability of a novel compound of the present invention to cross the blood brain barrier.

A preferred novel compound of the present invention is of the general Formula IV:

Formula IV or a pharmaceutically acceptable salt thereof,
wherein:
Z is an A-G(=K)—X—Y group,
and wherein:
A is alkyl or absent;
G is selected from the group consisting of carbon (C), sulfur (S) and substituted or unsubstituted phosphor (PRa);
K is selected from the group consisting of oxygen and sulfur;
X is selected from the group consisting of substituted or unsubstituted nitrogen (NRb), sulfur or absent; and
Y is selected from the group consisting of hydroxyalkyl and a polyalkylene glycol residue;
$R^1$ is selected from the group consisting of hydrogen, alkyl, cycloalkyl or aryl;
Each of $R^2$, $R^3$, $R^4$, $R^5$, $R^6$, $R^7$, $R^8$, $R^9$ and $R^{10}$, is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$, or, alternatively, at least two of $R^2$, $R^3$, $R^4$, $R^5$ and/or $R^6$, of $R^7$, $R^8$, $R^9$ and $R^{10}$ form a five- or six-membered aromatic, heteroaromatic, alicyclic or heteroalicyclic ring;
$R^{15}$ and $R^{16}$ are each independently selected from the group consisting of hydrogen, alkyl, cycloalkyl, aryl, carbonyl and sulfonyl, or, alternatively $R^{15}$ and $R^{16}$ form a five- or six-member heteroalicyclic ring; and
Ra and Rb are each independently hydrogen, alkyl, cycloalkyl or aryl.

According to a feature of the present invention, the polyalkylene glycol residue of a novel compound of the present invention has a general formula V:

$$[(CH_2)m\text{-}O]n\text{-}R^{17} \qquad \text{Formula V}$$

wherein each of m and n is independently an integer of 1-10 and $R^{17}$ is hydrogen, alkyl, cycloalkyl or aryl.

While the art described some compounds that are comprised of a non-steroidal anti-inflammatory drug (NSAID) moiety, including certain derivatives of N-phenylanthranilic acids, to which a residue of an anti-oxidant moiety or an —$ONO_2$ group is attached, optionally via a polyalkylene glycol spacer that is linked to the NSAID moiety via an amide bond, such compounds are excluded from the scope of the present invention. Hence, the novel compounds of the present invention include a polyalkylene glycol residue having Formula V above, which does not include an anti-oxidant moiety or a —$ONO_2$ group.

According to an additional feature, for a novel compound of the present invention, G is carbon, K is oxygen, each of $R^2$, $R^3$, $R^4$, $R^5$ and $R^6$ is independently selected from the group consisting of hydrogen, alkyl, halo and trihaloalkyl; and each of $R^7$, $R^8$, $R^9$ and $R^{10}$ is hydrogen.

According to an additional feature, X in formula IV above is NRb, such that the novel compounds include a polyalkylene glycol residue that is attached to the N-phenylanthranilic acid via an amide bond. As is detailed and demonstrated hereinafter, such compounds were found to be superior to similar compounds in which the polyalkylene glycol residue that is attached to the N-phenylanthranilic acid via a carboxylic ester bond (where X is O).

According to a preferred embodiment a novel compound of the present invention is selected from the group consisting of:

3
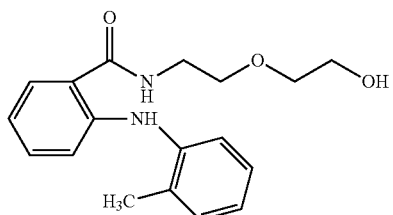

4
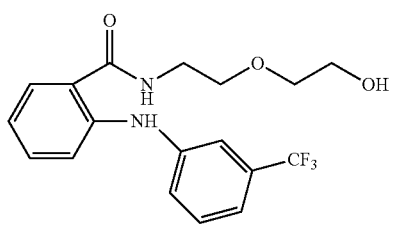

5
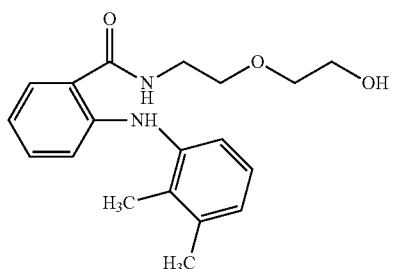

6
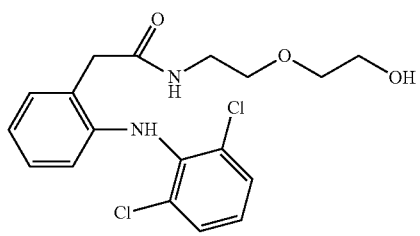

9
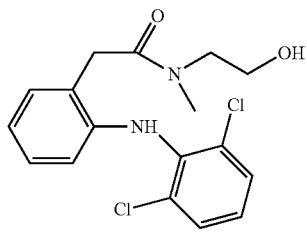

and pharmaceutically acceptable salts thereof.

According to an additional aspect of the present invention there is provided a pharmaceutical composition comprising, as an active ingredient, a compound of the present invention having a general formula IV and a pharmaceutically acceptable carrier.

According to a feature of the present invention there is provided a pharmaceutical composition, having as an active ingredient, any one of the compounds 3, 4, 5, 6 and/or 9.

According to yet another aspect of the present invention there is provided a method for the synthesis of the novel compounds described hereinabove. The method is effected by reacting a N-phenylanthranilic acid or a derivative thereof with a hydroxy alkyl or a polyalkylene glycol, which are terminated by a reactive group. The reactive group is selected such that it is capable of forming an ester bond with the N-phenylanthranilic acid or the derivative thereof.

As used herein, the phrase "an ester bond" describes a J(=L)-M bond, wherein J is carbon, sulfur or phosphor, preferably carbon, L is oxygen or sulfur and M is oxygen, sulfur or nitrogen (substituted or non-substituted, as is described hereinabove).

Preferred ester bonds, according to the present invention include a carboxylic ester bond [—C(=O)—O—], a carboxylic amide bond [—C(=O)—NR'—], a carboxylic thioester bond [—C(=O)—S—], a thiocarbonyl ester bond [—C(=S)—O—], a thiocarbonyl thioester bond [—C(=S)—S—] and a thiocarbonyl amide bond [—C(=S)—NR'—].

Accordingly, the reactive group is preferably hydroxy, amino or thiohydroxy, as defined hereinabove, and the polyalkylene glycol terminating with the reactive group has a general formula VII:

Formula VII wherein, V is hydroxy, amine or thiohydroxy, each of m and n is independently an integer of 1-10; and $R^{17}$ is hydrogen, alkyl, cycloalkyl or aryl.

The starting material, N-phenylanthranilic acid or the derivative thereof, preferably has a general formula VI:

Formula VI
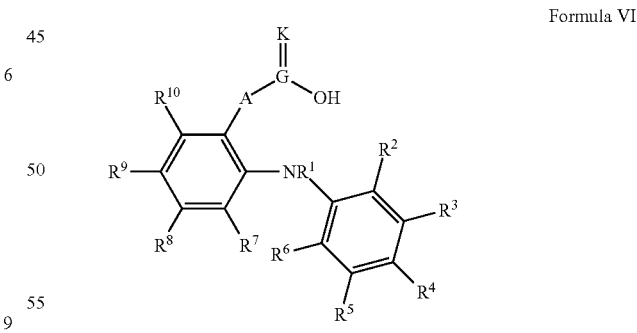

wherein,

A, G, K, $R^1$, $R^2$, $R^3$, $R^4$, $R^5$, $R^6$, $R^7$, $R^8$, $R^9$ and $R^{10}$, are as described hereinabove.

Preferably, in Formula VI, G is carbon, K is oxygen, each of $R^2$, $R^3$, $R^4$, $R^5$ and $R^6$ is independently hydrogen, alkyl, halo and trihaloalkyl; and each of $R^7$, $R^8$, $R^9$ and $R^{10}$ is hydrogen.

Since, as is described hereinabove, the ester bond is preferably an amide bond, the method according to this aspect of the present invention preferably further includes, prior to reacting with the hydroxyalkyl or the polyalkylene glycol, converting the N-phenylanthranilic acid or its derivative to a corresponding ester.

As is demonstrated in the Examples section that follows, the novel compounds of the present invention are easily and efficiently synthesized by the method of this aspect of the present invention.

Compounds of the present invention include known compounds such as meclofenamic acid (Compound 1), diclofenac (Compound 2) and 1-EBIO (Compound 10). 1-EBIO (Compound 10) has been found to increase the opening rate and hence the open probability Po of the channel in single-channel studies performed on intermediate (IK) and small conductance (SK) $Ca^{2+}$-activated K+ channel, see Syme et al. Am. J. Physiol. 278:C570-C581 (2000).

Compounds of the present invention also include compounds which are derivatives of N-phenylanthranilic acid, mainly derivatives of meclofenamic acid (Compound 1) and diclofenac (Compound 2). Exemplary compounds of the present invention are compounds 3, 4, 5, 6, 7, 8 and 9.

Herein it is demonstrated that these compounds are openers of KCNQ2/3 channel complex heterologously expressed in CHO cells. These compounds are also shown herein to reduce both evoked and spontaneous action potentials in cortical and peripheral neurons.

The compounds of the present invention have two main effects: shifting of the voltage dependence of KCNQ2/3 channel activation to more hyperpolarized potentials and slow channel deactivation. Similar to the effect on recombinant KCNQ2/3 channels, compounds 4, 5, 6 and 7 induce an approximately 20 mV negative shift in the threshold of M-current activation in cortical neurons, from −50 mV to −70 mV. As a result of this leftward shift of the KCNQ2/3 threshold of activation, there is a progressive hyperpolarization of the resting membrane potential. Without being bound to any theory in particular, the data presented herein in the Examples section that follows suggests that the compounds of the present invention either destabilize a closed channel conformation or stabilize the KCNQ2/3 channel in an open state. Further, exposure of channels to the compounds described herein also leads to a slowing of deactivation that contributes to the stabilization of the KCNQ2/3 channel in the open state. Without being bound to any theory in particular, it is possible that the compounds of the present invention modify the channel gating by shifting the voltage dependence of the voltage sensor S4 movement in the hyperpolarizing direction.

From a functional point of view, the leftward shift in the voltage dependence and the slowing of deactivation, caused by the compounds of the present invention, leads to substantial M-current activation at normal resting and subthreshold potentials. The especially large activation of KCNQ2/3 channels, e.g., in the case of meclofenamic acid (Compound 1) at potentials around −60/−50 mV (more than 10-fold increase in KCNQ2/3 current amplitude), shows that the compounds of the present invention cause membrane hyperpolarization. In addition, since the M-current (KCNQ2/3) is non-inactivating, its marked activation by compounds of the present invention contributes to a significant steady-state potassium conductance at subthreshold and threshold potentials, acting as brake for neuronal firing. Indeed, it is also demonstrated that compounds of the present invention depress the evoked and spontaneous cortical neurons activity.

It is important to note that the voltage range through which compounds of the present invention activate KCNQ2/3 channels makes theses compounds exceptionally useful for the treatment of ischemic stroke.

There are similarities between the properties exhibited by the compounds of the present invention and retigabine.

First, both the compounds of the present invention and retigabine all shift the voltage dependence of KCNQ2/3 channel activation leftwards, decelerating deactivation kinetics and hyperpolarizing the resting membrane potential [for retigabine discussed, for example, in Tatulian et al. J. Neurosci. 21: 5535-5545 (2001)].

Second, retigabine produces a secondary inhibitory action on KCNQ channels at positive potentials (e.g., above +20 mV) [Tatulian et al. J. Neurosci. 21: 5535-5545 (2000], as do the compounds of the present invention towards KCNQ2/3 channels.

An interesting difference between retigabine and the compounds of the present invention is related to the selectivity towards the KCNQ2 and KCNQ3 subunits. While retigabine exerts the strongest opener action on KCNQ3 homomeric channels [Tatulian et al. J. Neurosci. 21: 5535-5545 (2000], it is shown herein that the compounds of the present invention are more potent on KCNQ2 homomeric channels From a functional point of view, the leftward shift of the activation curve and the slowing of deactivation, effected by the compounds of the present invention, leads to substantial M-current activation at normal resting and subthreshold potentials. In addition, since the M-current (KCNQ2/3) is non-inactivating, activation by the compounds of the present invention is expected to contribute to a significant steady-state potassium conductance at subthreshold and threshold potentials, acting as a brake for neuronal firing. Indeed, compounds 4, 5, 6, 7 and 8 depress the evoked and spontaneous cortical neuron activity, as well as the peripheral neuron activity.

The voltage range through which the compounds of the present invention operate, indicates exceptional suitability for the treatment of epilepsy, ischemic stroke and neuropathic pain.

Neuropathic pain reflects neurological dysfunction and appears whenever nerves are damaged, by trauma, back pain, by diseases such as diabetes, herpes, or late-stage cancer, or by chemical injury. Neuropathic pain affects 1.5% of the population and is oftentimes chronic. Current treatments include strong analgesic interventions, like morphine or NSAIDs. While morphines are known as addictive drugs, NSAIDs treatment is known to involve adverse side effects, particularly gastrointestinal side effects. Interestingly, M-channels were recently found to be expressed in regions of the nervous system involved in neuropathic pain such as dorsal and ventral horn of the spinal cord, as well as sensory dorsal root and trigeminal ganglion neurons. In neuropathic pain, sensory neurons become hyperexcitable as compared to normal conditions and often fire spontaneously. There is strong evidence that hyperexcitability and ectopic discharge, which underlie allodynia, hyperalgesia and spontaneous (ongoing) pain, are mediated by abnormal activity of a variety of ion channels, including KCNQ2/3 potassium channels. Thus, by modulating the activity of KCNQ2/3 potassium channels and thereby dampening sensory neuron hyperexcitability, the compounds described herein can be used as selective and highly potent agents for treating neuropathic pain. By acting via such a selective mechanism the compounds of the present invention are devoid of the side effects associated with the presently known analgesics.

Hence, according to an additional aspect of the present invention, there is provided a method for treating neuropathic pain, which is effected by administering to a subject in need thereof a therapeutically effective amount of one or more of the compounds described herein.

The method, according to this aspect of the present invention, can further include co-treatment with one or more analgesic such as NSAID, morphine and the like.

As is described hereinabove, the compounds according to the present invention can be efficiently utilized in the treatment of various CNS disorders. Most of the presently known and used medications for treating such conditions, and particularly analgesics for treating neuropathic pain, are characterized as cyclooxygenase (COX) inhibitors.

The differential tissue distribution of COX-1 and COX-2 has provided a rationale for the design of selective COX-2 inhibitors as anti-inflammatory and analgesic agents with lower incidence of associated gastrointestinal side effects than NSAIDs acting as COX-1 inhibitors. This feature served as the basis for design of the highly selective tricyclic COX-2 inhibitors. However, despite the relatively safe pharmacological profile of selective COX-2 inhibitors, there is now increasing concern regarding their use in patients at risk for an adverse cardiovascular event such as myocardial infarction. This increased risk is thought to be triggered by a reduction in the level of the desirable platelet aggregation inhibitor and vasodilatory prostacyclin ($PGI_2$) in conjunction with an increased level of the undesirable potent platelet activator and aggregator thromboxane A2 (TxA2). Compounds which do not exert COX inhibitory activity are therefore highly advantageous for treating the above conditions.

As is demonstrated in the Examples section that follows, it has been surprisingly found that some of the compounds described herein are characterized as having no inhibition activity on both COX 1 and COX 2. Such compounds can therefore be advantageously used in any of the methods described herein. Exemplary compounds according to this feature of the present invention are those having the general Formula IV above, and particularly compounds in which the polyalkylene glycol residue is attached to the N-phenylanthranilic acid via an amide bond and which are also referred to herein as "amidated" compounds. As is further demonstrated in the Examples section that follows, the COX inhibition activity of the "amidated" compounds was found to be significantly lower than that of the "esterified" compounds (compounds in which the polyalkylene glycol residue is attached to the N-phenylanthranilic acid via a carboxylic ester bond).

Preferred compounds according to the present invention, which do not exhibit COX inhibition activity, include Compounds 5 and 6, described herein.

The compounds of the present invention can be utilized in any of the methods described herein, either per se or as a part of a pharmaceutical composition, which further comprises a pharmaceutically acceptable carrier.

According to a feature of the present invention, such a pharmaceutical composition is packaged in a packaging material and identified in print, in or on the packaging material, for use in the treatment or prevention of a condition or disorder, e.g., in the peripheral or central nervous system, associated with altered activity of a voltage-dependent potassium channel, as detailed hereinabove.

As used herein a "pharmaceutical composition" refers to a preparation of one or more of the compounds of the present invention (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound. Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As stated above, techniques for formulation and administration of compounds as medicaments may be found in "Remington's Pharmaceutical Sciences," Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile, pyrogen-free water, before use.

The preparation of the present invention may also be formulated in rectal compositions such as suppositories or retention enemas, using, e.g., conventional suppository bases such as cocoa butter or other glycerides.

In addition to the formulations described previously, a preparation of the present invention may also be formulated for local administration, such as a depot preparation. Such long acting formulations may be administered by implantation (for example subcutaneously or intramuscularly) or by intramuscular injection. Thus, for example, the preparation may be formulated with suitable polymeric or hydrophobic materials (for example, as an emulsion in an acceptable oil) or ion exchange resins, or as sparingly soluble derivatives such as sparingly soluble salts. Formulations for topical administration may include, but are not limited to, lotions, suspensions, ointments gels, creams, drops, liquids, sprays emulsions and powders.

Pharmaceutical compositions suitable for use in context of the present invention include compositions wherein the active ingredients are contained in an amount effective to achieve the intended purpose. More specifically, a therapeutically effective amount means an amount of active ingredient effective to prevent, alleviate or ameliorate a condition and/or symptoms thereof and/or effects thereof.

Determination of a therapeutically effective amount is within the capability of those skilled in the art, especially in light of the detailed disclosure provided herein.

For any preparation used in the methods of the invention, the therapeutically effective amount or dose can be estimated initially from cell culture assays. For example, a dose can be formulated in animal models to achieve a circulating concentration range that includes the $IC_{50}$ as determined in cell culture. Such information can be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active moiety which are sufficient to maintain the kinase modulating effects, termed the minimal effective concentration (MEC). The MEC will vary for each preparation, but can be estimated from in vitro data; e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

It is noted that, in the case of local administration or selective uptake, the effective local concentration of the drug may not be related to plasma concentration. In such cases, other procedures known in the art can be employed to determine the effective local concentration.

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is detailed herein.

The pharmaceutical composition of the present invention, by comprising, as an active ingredient, a compound of the present invention which serve for modulating, generally by opening, a respective potassium channel or depressing cortical and/or peripheral neuron activity, can be used for the treatment, prevention or amelioration of conditions or disorders associated with altered activity of a voltage-dependent potassium channel or of a cortical and/or peripheral neuron. Generally, the potassium channel modulated is a KCNQ2 channel and/or a KCNQ3 channel and/or a KCNQ2/3 channel. Peripheral or central nervous system conditions or disorders associated with altered activity of a voltage-dependent potassium channel that are preferably treated or prevented by the pharmaceutical compositions of the present invention include, but are not limited to epilepsy, ischemic stroke, migraine, ataxia, myokymia, neurogenic pain, neuropathic pain Alzheimer's disease, Parkinson's disease, age-related memory loss, learning deficiencies, bipolar disorder, trigeminal neuralgia, spasticity, mood disorder, psychotic disorder, brain tumor, hearing and vision loss, anxiety and a motor neuron disease. Preferably the composition is packaged in a packaging material and is identified in print, in or on the packaging material, for use in the treatment or prevention of a peripheral or central nervous system condition or disorder associated with altered activity of a voltage-dependent potassium channel.

The pharmaceutical composition may further comprise additional pharmaceutically active or inactive agents such as, but not limited to, an anti-bacterial agent, an antioxidant, a buffering agent, a bulking agent, an anti-inflammatory agent, an anti-viral agent, a chemotherapeutic agent and an antihistamine.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Materials and Experimental Methods

Chemical Syntheses:

Meclofenamic acid (Compound 1), diclofenac (Compound 2) and 1-ethyl benzimidazolone (1-EBIO, Compound 10) are commercially available and were purchased from Sigma-Aldrich (St. Louis, Mo., USA).

The chemical structures of Compounds 1-10 of the present invention are presented in FIG. 17.

Compound 3-9 were prepared as follows:

Synthesis of Compound 7:

Diclofenac (50 mg, 0.17 mmol) was dissolved in dry dichloromethane (DCM) and a catalytic amount of N-dimethylaminopyridine (DMAP) and diethylene glycol (0.08 ml, 0.85 mmol) were added. The mixture was cooled to 0° C. while stirring, and a solution of dicyclohexyl carbodiimide (DCC, 52.6 mg, 0.255 mmol) in DCM was added dropwise. The resulting suspension was then stirred at 0° C. for 30 minutes, while being monitored by TLC (using a mixture of 1:1 EtOAc:Hexane as eluent). The solid was thereafter removed by filtration and was washed with DCM. The filtrate was concentrated under reduced pressure and chromatographed on silica gel to afford the pure product (43 mg, 66% yield).

$^1$H-NMR (200 MHz, $CDCl_3$): δ=7.35 (2H, d, J=8); 7.19-7.06 (2H, m); 6.99 (1H, d, J=8); 6.96 (1H, d, J=8); 6.56 (1H, d, J=8); 4.35 (2H, m); 3.8 (2H, s); 3.65-3.75 (4H, m); 3.53-3.57 (2H, m) ppm.

Synthesis of Compound 8:

Compound 8 was prepared according to the procedure described above for Compound 7, using diethyleneglycol methyl ether instead of diethylene glycol. The product was obtained in 53% yield.

$^1$H-NMR (200 MHz, $CDCl_3$): δ=7.35 (2H, d, J=8); 7.19-7.06 (2H, m); 6.99 (1H, d, J=8); 6.96 (1H, d, J=8); 6.56 (1H, d, J=8); 4.34-4.29 (2H, m); 3.85 (2H, s); 3.75-3.70 (2H, m); 3.61-3.59 (2H, m); 3.58-3.50 (2H, m) ppm.

Synthesis of Compounds 3, 4, 5, 6 and 9—General Procedure:

To the corresponding acid (meclofenamic acid, diclofenac or a derivative thereof) (0.506 mmol), dissolved in dichloromethane, N-hydroxy succinimide (0.76 mmol) and DCC (0.76 mmol) were added. The mixture was stirred for 1 hour while being monitored by TLC (using a mixture of 1:1 EtOAc:Hexane as eluent). After completion of the reaction the mixture was filtered and the solvent was evaporated. The crude product was purified by column chromatography to give the pure N-hydroxy succinimide ester intermediate of Compounds 3, 4, 5, 6 and 9, as follows:

Intermediate of Compound 3:

Yield 90%. $^1$H-NMR (200 MHz, $CDCl_3$): δ=8.69 (1H, s); 8.09-8.14 (1H, dd, J=1.7, J=8.6); 7.32-7.37 (1H, dt, J=1.8, J=8.5); 7.14-7.28 (3H, m); 6.72-6.80 (2H, m); 2.9 (4H, s); 2.29 (3H, s) ppm.

Intermediate of Compound 4:

Yield 90%. $^1$H-NMR (200 MHz, $CDCl_3$): δ=8.91 (1H, s); 8.10-8.15 (1H, dd, J=1.6, J=8.18); 7.33-7.48 (5H, m); 7.24 (1H, d, J=7.8); 6.80-6.88 (1H, dt, J=1.06, J=7.1); 2.9 (4H, s) ppm.

Intermediate of Compound 5:

Yield 100%. $^1$H-NMR (200 MHz, $CDCl_3$): δ=8.6 (1H, s); 8.12 (1H, dd, J=1.53, J=7.4); 7.32 (1H, m); 7.06-7.13 (3H, m); 6.66-6.74 (2H, m); 2.9 (4H, s); 2.32 (3H, s); 2.14 (3H, s) ppm.

Intermediate of Compound 6 and 9:

Yield 89%. $^1$H-NMR (200 MHz, $CDCl_3$): δ=7.35 (3H, d, J=8); 7.18-7.26 (1H, m); 6.93-7.07 (2H, m); 6.6-6.63 (1H, d, J=7.9); 6.2 (1H, s); 4.13 (2H, s); 2.84 (4H, s) ppm.

The corresponding intermediate was dissolved in 1 ml of dimethylformamide (DMF), diethyleneglycolamine or (2-hydroxyethyl)methylamine for Compound 9 (1 equivalent), was added and the mixture was stirred for 30 minutes, while being monitored by TLC (using EtOAc as eluent). After completion of the reaction the solvent was removed under reduced pressure. The product was purified by column chromatography to give Compounds 3, 4, 5, 6 and 9, as follows:

Compound 3:

Yield 55%. $^1$H-NMR (200 MHz, CDCl$_3$): δ=9.31 (1H, s); 7.45-7.50 (1H, dd, J=0.6, J=8); 6.99-7.22 (5H, m); 6.67-6.94 (1H, dt, J=1.8, J=6.5); 3.54-3.74 (8H, m); 2.33 (3H, s) ppm.

Compound 4:

Yield 70%. $^1$H-NMR (200 MHz, CDCl$_3$): δ=9.44 (1H, s); 7.46-7.50 (1H, dd, J=0.6, J=8); 7.4 (2H, d, J=9); 7.16-7.32 (5H, m); 7.09 (1H, bs); 6.79-6.84 (1H, dt, J=1.8, J=6.5); 3.54-3.73 (8H, m) ppm.

Compound 5:

Yield 88%. $^1$H-NMR (200 MHz, CDCl$_3$): δ=9.19 (1H, s); 7.41-7.45 (1H, dd, J=1.53, J=7.4); 7.14-7.21 (2H, m); 7.06-7.13 (1H, t, J=); 6.93-6.96 (2H, m); 6.65-6.69 (2H, m); 3.6-3.8 (8H, m); 2.32 (3H, s); 2.20 (3H, s) ppm.

Compound 6:

Yield 72%. $^1$H-NMR (200 MHz, CDCl$_3$): δ=7.35 (2H, d, J=8); 7.19-7.06 (2H, m); 6.99 (1H, d, J=8); 6.96 (1H, d, J=8); 6.56 (1H, d, J=8); 3.69 (2H, s); 3.55-3.49 (4H, m) ppm.

Compound 9:

Yield 63%. $^1$H-NMR (200 MHz, CDCl$_3$): δ=7.35 (2H, d, J=8); 7.19-7.06 (2H, m); 6.99 (1H, d, J=8); 6.96 (1H, d, J=8); 6.56 (1H, d, J=8); 3.78-3.74 (2H, m); 3.64-3.57 (2H, m); 3.23 (2H, s); 2.95 (3H, s) ppm.

Activity Assays:

CHO Cell Culture and Transfection:

CHO (Chinese Hamster Ovary) cells were grown in Dulbecco's modified Eagle's medium supplemented with 2 mM glutamine, 10% fetal calf serum and antibiotics. Briefly, 40,000 cells seeded on poly-D-lysine-coated glass coverslips (13 mm diameter) in a 24-multiwell plate were transfected with pIRES-CD8 (0.5 µg) as a marker for transfection and with KCNQ2 (0.5 µg) and/or KCNQ3 (0.5 µg). For electrophysiology, transfected cells were visualized approximately 40 hours following transfection, using the anti-CD8 antibody-coated beads method (Jurman et al., Biotechniques. 17(5):876-81, 1994). Transfection was performed using 3.5 µl of lipofectamine (Gibco-BRL) according to the manufacturer's protocol.

Neuronal Cortical, F-11 and DRG Cells Culture:

Sprague Dawley rat embryos (E18) were removed by caesarian section and their cortices were dissected out. The tissue was digested with papain (100 U; Sigma, St. Louis, Mo.) for 20 minutes, triturated to a single-cell suspension, and plated at a density of 40,000 cells per ml on a substrate of bovine collagen type IV and 100 µg/ml poly-L-lysine in 13 mm diameter glass coverslip of a 24-multiwell plate. The culture medium consisted of Modified Eagle's Medium containing 5% horse serum (Biological Industries, Beit HaEmek, Israel), B-27 neuronal supplement (Invitrogen, Carlsbad, Calif.), 100 U/ml penicillin, 100 µg/ml streptomycin, and 2 mM glutamine. D-Glucose was supplemented to a final concentration of 6 g/l. Cytosine-1-D-arabinofuranoside (5 µM) was added after 5 days to arrest glial cell proliferation.

F-11 neuronal cells were similarly cultured in F-12 Ham media containing 2 mM 1-glutamine supplemented with 10% fetal bovine serum, HAT supplement and antibiotics.

Dorsal root ganglion (DRG) neurons were dissected from 2-4 days-old ICR mice that were decapitated. DRGs were placed in Hank's balanced saline solution (HBSS) and were prepared by enzymatic dissociation. Briefly, cells were incubated for 30 minutes in 5 mg/ml dispase (Sigma), 2 mg/ml collagenase type 1A (Sigma) and 0.1 mg/ml DNase (Invitrogen/Gibco) in calcium and magnesium-free HBSS, and the ganglia were thereafter mechanically triturated with a fire-polished glass Pasteur pipette. The ganglia were then centrifuged for 5 minutes at 80×g and resuspended in DMEM supplemented with 2 mM L-glutamine, 16.5 mM NaCO$_3$, 6 g/l glucose, 5 ml penicillin/streptomycin and 10% fetal calf serum. For electrophysiological recording, dissociated neurons were plated on 13 mm glass coverslips previously coated with poly-D-lysine (1 mg/ml) and laminin (10 µg/ml) and were used after 2-6 days in culture.

All cultures were maintained at 37° C. in humidified air containing 5% CO$_2$.

Electrophysiology:

For current measurements in CHO cells, recordings were performed 40 hours following transfection, using the whole-cell configuration of the patch-clamp technique [Hamill et al., Nature 294: 462-464 (1981)]. Signals were amplified using an Axopatch 200B patch-clamp amplifier (Axon Instruments, Foster City, Calif., USA), sampled at 2 kHz and filtered at 800 Hz via a 4-pole Bessel low pass filter. Data were acquired using pClamp 8.1 software (Axon Instruments, Foster City, Calif., USA) and an Elonex Pentium III computer in conjunction with a DigiData 1322A interface (Axon Instruments, Foster City, Calif., USA). The patch pipettes were pulled from borosilicate glass (Warner Instrument. Corp., Hamden, Conn., USA) with a resistance of 2-5 MΩ and were filled with (in mM): 130 KCl, 1 MgCl$_2$, 5 K$_2$ATP, 5 EGTA, 10 HEPES, adjusted with KOH at pH 7.4 (290 mOsm). The external solution contained (in [mM]): 140 NaCl, 4 KCl, 1.8 CaCl$_2$, 1.2 MgCl$_2$, 11 glucose, 5.5 HEPES, adjusted with NaOH at pH 7.4 (310 mOsm). Series resistances (3-13 MΩ) were compensated (75-90%) and periodically monitored. For current-clamp measurements of rat cortical neurons, recordings were performed 10-14 days after plating, while rat DRG neurons recordings were performed 3 days after plating. The patch pipettes were filled with (in [mM]): 135 KCl, 1 K$_2$ATP, 1 MgATP, 2 EGTA, 1.1 CaCl$_2$, 5 glucose, 10 HEPES, adjusted with KOH at pH 7.4 (315 mOsm). The external solution contained (in [mM]): 140 NaCl, 4 KCl, 2 CaCl$_2$, 2 MgCl$_2$, 5 glucose, 10 HEPES, adjusted with NaOH at pH 7.4 (325 mOsm). For evoking the neuronal action potentials, 50-300 pA currents were injected into the cells for 800 ms (square pulse). Recordings were sampled at 5 kHz and filtered at 2 KHz via a 4-pole Bessel low pass filter. For voltage-clamp measurements of rat cortical neurons, the patch pipettes were filled with (in mM): 90 K-acetate, 40 KCl, 3 MgCl$_2$, 2 K$_2$ATP, 20 HEPES, adjusted with KOH at pH 7.4 (310-315 mOsm). The external solution contained (in mM): 120 NaCl, 23 NaHCO$_3$, 3 KCl, 2.5 CaCl$_2$, 1.2 MgCl$_2$, 11 glucose, 0.0005 tetrodotoxin (TTX), 5 HEPES, adjusted with NaOH at pH 7.4 (325 mOsm).

Current measurements in *Xenopus* oocytes were performed as described in the art [Peretz et al. J. Physiol 545: 751-766 (2002)]. Briefly, two-electrode voltage-clamp measurements were performed 3-5 days following cRNA microinjection into oocytes. Oocytes were bathed in a modified ND96 solution containing (in mM): 96 NaCl, 2 KCl, 1 MgCl$_2$, 0.1 CaCl$_2$ and 5 HEPES titrated to pH=7.4 with NaOH. Whole-cell currents were recorded at room temperature (20° C.-22° C.) using a GeneClamp 500 amplifier (Axon Instruments, Foster City, Calif., USA). Glass microelectrodes (A-M Systems, Inc., Carlsborg, Wis., USA) were filled with 3M KCl and had tip resistances of 0.5-1.5 MΩ. Stimulation of the preparation, data acquisition and analyses were performed using the pCLAMP 6.02 software (Axon Instruments, Foster City, Calif., USA) and a 586 personal computer Pentium 4 interfaced with a Digidata 1200 interface (Axon Instruments, Foster City, Calif., USA). Current signals were filtered at 0.5 kHz and digitized at 2 kHz.

Maximal Electroshock Seizure Test:

The anti-convulsant effect of diclofenac and meclofenamic acid was measured by the maximal electroshock seizure model (MES) in ICR mice. All animals were treated in accordance with the Guide for the Care and Use of Laboratory Animals as adopted and promulgated by the U.S. National Institutes of Health. The procedures followed for experimentation and maintenance of the animals were approved by the animal research ethics committee of Tel Aviv University and in accordance with the Guide for the Care and Use of Laboratory Animals (1996. National Academy of Sciences, Washington D.C). Minimal electroshock were induced in adult mice by means of two transcorneal electrodes delivering an alternative current of 50 mA at 60 Hz for 0.2 sec using rodent shocker (Hugo Sachs Electronik, type 221). This was shown to cause tonic convulsions in 100% of the animals tested. The tested compounds were dissolved in 0.9% saline were administered intraperitoneally either 30 minutes or 2 hours before the electroshock was performed. Animals failing to show tonic hind limb extension were scored as protected and were expressed in percentage.

Immunocytochemistry:

Cortical neurons were grown in culture for 10-14 days on 13 mm diameter coated glass coverslips in 24-well plates. Cells were carefully rinsed for 10 minutes in phosphate buffered saline (PBS) and the neurons were subsequently fixed for 20 minutes in 4% paraformaldehyde in PBS. Following extensive washes in PBS, the cells were blocked and permeabilized by incubation with 10% normal goat serum (NGS) in PBS containing 0.2% Triton X-100. Cells were then washed for 10 minutes in PBS containing 1% NGS. Neurons were incubated at 4° C. overnight with anti-KCNQ2 and anti-KCNQ3 channel antibodies diluted in PBS containing 1% NGS. A rabbit polyclonal antibody to KCNQ2 (1:500; Alomone labs) was combined with a goat polyclonal antibody to KCNQ3 (N19: 1:50; Santa Cruz Biotechnology); alternatively a rabbit polyclonal antibody to KCNQ3 (1:100; Alomone labs) was combined with a goat polyclonal antibody to KCNQ2 (N19:1:50; Santa Cruz Biotechnology). After a wash in PBS, cells were incubated for an hour at room temperature with secondary antibodies, CY2-conjugated anti-rabbit IgG (1:200; Jackson Immunoresearch) and RRX-conjugated anti-goat IgG (1:100; Jackson Immunoresearch). Neurons were viewed and digital images taken using a Zeiss LSM 410 confocal microscope.

COX (Cyclooxygenase) Activity Assays:

C-26 cells were plated on 24-well plates using RPMI medium. Different concentrations of the tested compound were added thereto and the cells were incubated for 30 minutes at 37° C. 30 µM exogenic arachidonic acid was then added and incubation was continued for 20 minutes (37° C.), so as to allow the cells to synthesize $PGE_2$. Indomethacin was added thereafter (10 µM), to stop and completely block the activity. Then, the upper solution was removed into clean 24-wells. To the remained cells 100 µl NaOH (1M) were added to induce cytolysis, and the cells were left for later protein measurement. The solution removed to the new 24-well was used for a radioimmunoassay. The COX activity was estimated by calculating the ng PGE2/mg protein parameter.

Data Analyses:

Data analysis was performed using the Clampfit program (pClamp 8.1, Axon Instruments, Foster City, Calif., USA), Microsoft Excel 98 (Microsoft Corp., Redmond, Wash., USA), Axograph 4.6 (Axon Instruments, Foster City, Calif., USA) and Prism 2.0 (GraphPad, San Diego, Calif., USA). Leak subtraction was performed off-line, using the Clampfit program of the pClamp 8.1 software. To analyze the KCNQ2/3 channel deactivation, a single exponential fit was applied to the tail currents. Chord conductance (G) was calculated by using the equation:

$$G=I/(V-V_{rev})$$

where I corresponds to the current amplitude measured at the end of the pulse and $V_{rev}$, the calculated reversal potential assumed to be −90 mV in CHO cells and −98 mV in *Xenopus* oocytes. G was estimated at various test voltages V and then, normalized to a maximal conductance value, $G_{max}$, calculated at +40 mV. Activation curves were fitted by a Boltzmann distribution:

$$G/G_{max}=1/\{1+\exp[(V_{50}-V)/s]\}$$

where $V_{50}$ is the voltage at which the current is half-activated and s is the slope factor. All data were expressed as mean±SEM. Statistically significant differences were assessed by Student's t-test.

EXPERIMENTAL RESULTS

Assays Conducted with Meclofenamic Acid (Compound 1), Diclofenac (Compound 2) and 1-EBIO (Compound 10)

Example 1

The Effect of Meclofenamic Acid (Compound 1) and 1-EBIO (Compound 10) on the KCNQ2/3 Current The leftwards-shift of the voltage dependence of activation of the KCNQ2/3 current induced by Meclofenamic acid (1) and 1-EBIO (10) is discussed with reference to FIGS. 1A-1D.

When KCNQ2 and KCNQ3 subunits are expressed separately as homomeric channels in various expression systems, they give rise to relatively small potassium currents, especially for KCNQ3 (Wang et al. Science 282: 1890-1893 (1998) and Yang et al. J. Biol. Chem. 273: 19419-19423 (1998)). However, KCNQ2 co-expressed with KCNQ3 produces a current whose biophysical and pharmacological properties are very similar to those of the native M-current (Main et al. Mol. Pharmacol. 58: 253-262 (2000), Wang et al. Science 282: 1890-1893 (1998) and Yang et al. J. Biol. Chem. 273: 19419-19423 (1998)).

CHO cells were co-transfected with the two corresponding cDNAs of KCNQ2 and KCNQ3 at an equimolar ratio and exposed to meclofenamic acid (Compound 1) and 1-EBIO (Compound 10) so as to identify the effect of these compounds on M-current.

Figure 1:
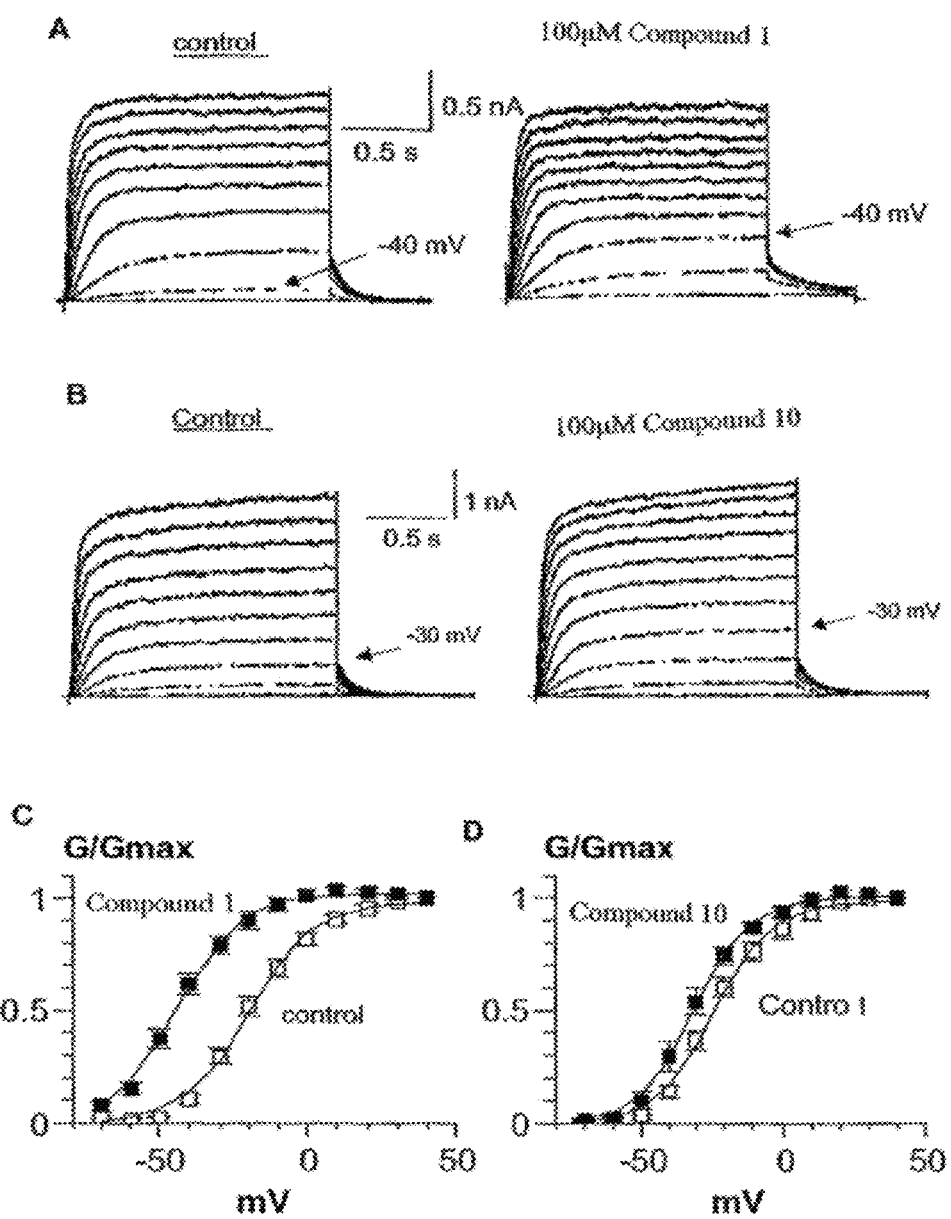

Turning to FIGS. 1A and 1B, representative traces were recorded from the same cell before (left panel) and after (right panel) external application of 100 µM meclofenamic acid (Compound 1, FIG. 1A) and 100 µM 1-EBIO (Compound 10, FIG. 1B). The membrane potential was stepped from −70 mV to +40 mV for 1.5 second pulse duration, in 10 mV increments, followed by 0.75 second pulse to −60 mV, producing the tail current. The holding potential of all experiments was −85 mV.

The normalized conductance ($G/G_{max}$) was plotted as a function of the voltage steps, for the control (open squares) and meclofenamic acid (Compound 1, FIG. 1C) or 1-EBIO (Compound 10, FIG. 1D) treated cells (solid square). The activation curves were fitted using the Boltzmann distribution.

FIG. 1A (left panel) shows representative traces of the KCNQ2/3 current activated by step depolarization above a voltage threshold of about −50 mV. Addition of 100 μM meclofenamic acid externally shown in FIG. 1A (right panel) produced a pronounced leftward shift of 22.7 mV in the voltage-dependence of KCNQ2/3 current activation (FIG. 1C), from $V_{50}=-19.65\pm1.85$ mV (n=24) to $V_{50}=-42.34\pm2.08$ mV (n=14). The slope parameter of the Boltzmann fitting curve did not change significantly with s=−9.46±0.41 mV/e fold and s=−10.50±0.93 mV/e fold, for control and meclofenamic acid (Compound 1), respectively.

In FIG. 1B (right panel) the leftward shift caused by 100 μM 1-EBIO (Compound 10) of 7.9 mV (p<0.005) in the voltage-dependence of KCNQ2/3 current activation, from $V_{50}=-22.9\pm1.8$ mV to $V_{50}=-30.8\pm2.8$ mV (n=4). The slope parameters of the Boltzmann fitting curve did not change significantly and were s=−10.2±1.1 mV/e-fold and s=−9.5±0.7 mV/e-fold, for control and 1-EBIO (Compound 10), respectively.

Consequently, upon exposure to meclofenamic acid (Compound 1) or 1-EBIO (Compound 10) the KCNQ2/3 current activated at more hyperpolarized potentials above a voltage threshold of about −60 mV versus −50 mV for control (FIGS. 1C and 1D).

To make sure that the effects of meclofenamic acid (Compound 1) on KCNQ2/Q3 K' currents were not dependent on a particular cell type, its action on the *Xenopus* oocyte expression system was also studied. As is shown in FIG. 19A, external application of 25 μM meclofenamic acid produced a 53±8% (n=7, p<0.01) increase in KCNQ2/Q3 current amplitude when the oocyte membrane was stepped from −80 mV to −40 mV, as in the case of CHO cells. As is shown in FIG. 19B, similarly, meclofen (25 μM) produced a leftward shift of −15.9 mV in the voltage-dependence of KCNQ2/Q3 current activation, from $V_{50}=-28.6\pm2.9$ mV (n=10) to $V_{50}=-44.5\pm3.1$ mV (n=10) in control and meclofen-treated cells, respectively.

As a result of this leftward shift of the KCNQ2/Q3 activation curve, incubation of the oocytes with increasing concentrations of meclofenamic acid (Compound 1) led to a progressive hyperpolarization of the oocyte resting membrane potential from −56±2 mV to −72±3 mV, with an $EC_{50}=11.7\pm5.2$ μM (n=6), as is shown in FIG. 19C.

Example 2

Augmentation of the KCNQ2/3 Current Amplitude by Meclofenamic Acid (Compound 1) and 1-EBIO (Compound 10)

The augmentation of the KCNQ2/3 current amplitude by meclofenamic acid (Compound 1) and 1-EBIO (Compound 10) is discussed with reference to FIGS. 1A-1D and FIGS. 2A-2C.

As is shown in FIG. 2A, the KCNQ2/3 current increases in the presence of meclofenamic acid (Compound 1) and 1-EBIO (Compound 10). Traces were recorded in the absence (control) and presence of meclofenamic acid (Compound 1, left panel) or 1-EBIO (Compound 10, right panel). The cells were stepped to −20 mV for 1.5 second pulse duration. In this train protocol, the interval between the pulses was 30 seconds.

FIG. 2B shows the percentages of the current measured in the presence (+) or absence (−) of meclofenamic acid (Compound 1, left panel) or 1-EBIO (Compound 10, right panel), where the control is 100%.

In FIG. 2C, the current amplitude (nA) was plotted against the step voltage, in the hyperpolarized potential range (−70 mV to −20 mV) to emphasize the negative shift of the threshold for channel activation, in response to meclofenamic acid (Compound 1, left panel) or 1-EBIO (Compound 10, right panel) application, Within about one minute of external application of meclofenamic acid (Compound 1) a large increase in KCNQ2/3 current amplitude across a range of test potentials between −50 to 0 mV was observed (FIG. 1C and FIG. 2A, left panel). The effect of meclofenamic acid (Compound 1) was fully reversible (data not shown). In the train protocol, when the cells were stepped to −20 mV the application of meclofenamic acid (Compound 1) induced an increase of the current amplitude by up to 72%, from 844±130 pA to 1451±164 pA (n=15), for control and meclofenamic acid (Compound 1), respectively (FIG. 2B, left panel). From the normalized conductance-voltage relation ($G/G_{max}$) and the normalized current-voltage relation ($I/I_{max}$) presented in FIGS. 1C and 2C, respectively, one can see that meclofenamic acid (Compound 1) increased KCNQ2/3 potassium current primarily via a leftward shift in the voltage-dependence of channel activation. As the test potentials became more positive and approached saturation values of the activation curve (i.e., +20 mV), the effects of meclofenamic acid (Compound 1) on KCNQ2/3 current amplitude became very small. Clearly, the most pronounced action of meclofenamic acid (Compound 1) was exerted at negative physiologically relevant potentials. At −50 mV, −40 mV and −30 mV, meclofenamic acid (Compound 1) increased KCNQ2/3 current amplitude by more than 10-fold, 5-fold and 2.5-fold, respectively (FIGS. 1A, 1C and 2C, left panels).

Similarly, addition of 100 μM 1-EBIO (Compound 10) quickly led to an increase in KCNQ2/3 current amplitude across a range of test potentials between −50 to −10 mV (FIG. 1B, FIG. 2A and FIG. 2B, right panels), although the effect was less pronounced than the effect of meclofenamic acid (Compound 1). The effect of 1-EBIO (Compound 10) was fully reversible (data not shown). In the train protocol, when the cells were stepped to −30 mV the application of 1-EBIO (Compound 10) induced an increase of the current amplitude by up to 57%, from 945±135 pA (n=14) to 1483±194 (n=14), for control and 1-EBIO (Compound 10), respectively. From the normalized conductance-voltage relation ($G/G_{max}$) and the normalized current-voltage relation ($I/I_{max}$) presented in FIGS. 1D and 2C, right panel, respectively, one can see that 1-EBIO (Compound 10) increased KCNQ2/3 potassium current primarily via a leftward shift in the voltage-dependence of channel activation. As the test potentials became more positive and approached the saturation values of the activation curve, the effects of 1-EBIO (Compound 10) on KCNQ2/3 current amplitude became weaker. FIG. 1D shows the leftward shift of the threshold for channel activation of about 10 mV. In addition, FIG. 2C, right panel shows that the most pronounced action of 1-EBIO (Compound 10) was exerted at negative physiologically relevant potentials. At −50 mV and −40 mV, 1-EBIO (Compound 10) increases the KCNQ2/3 current amplitude by more than 10-fold and 3-fold, respectively.

Example 3

The Effect of Meclofenamic Acid (Compound 1) and 1-EBIO (Compound 10) on KCNQ2/3 Deactivation Kinetics The slowing down of KCNQ2/3 deactivation kinetics caused by meclofenamic acid (Compound 1) and 1-EBIO (Compound 10) is discussed with reference to FIGS. 3A-3E.

Figure 3:
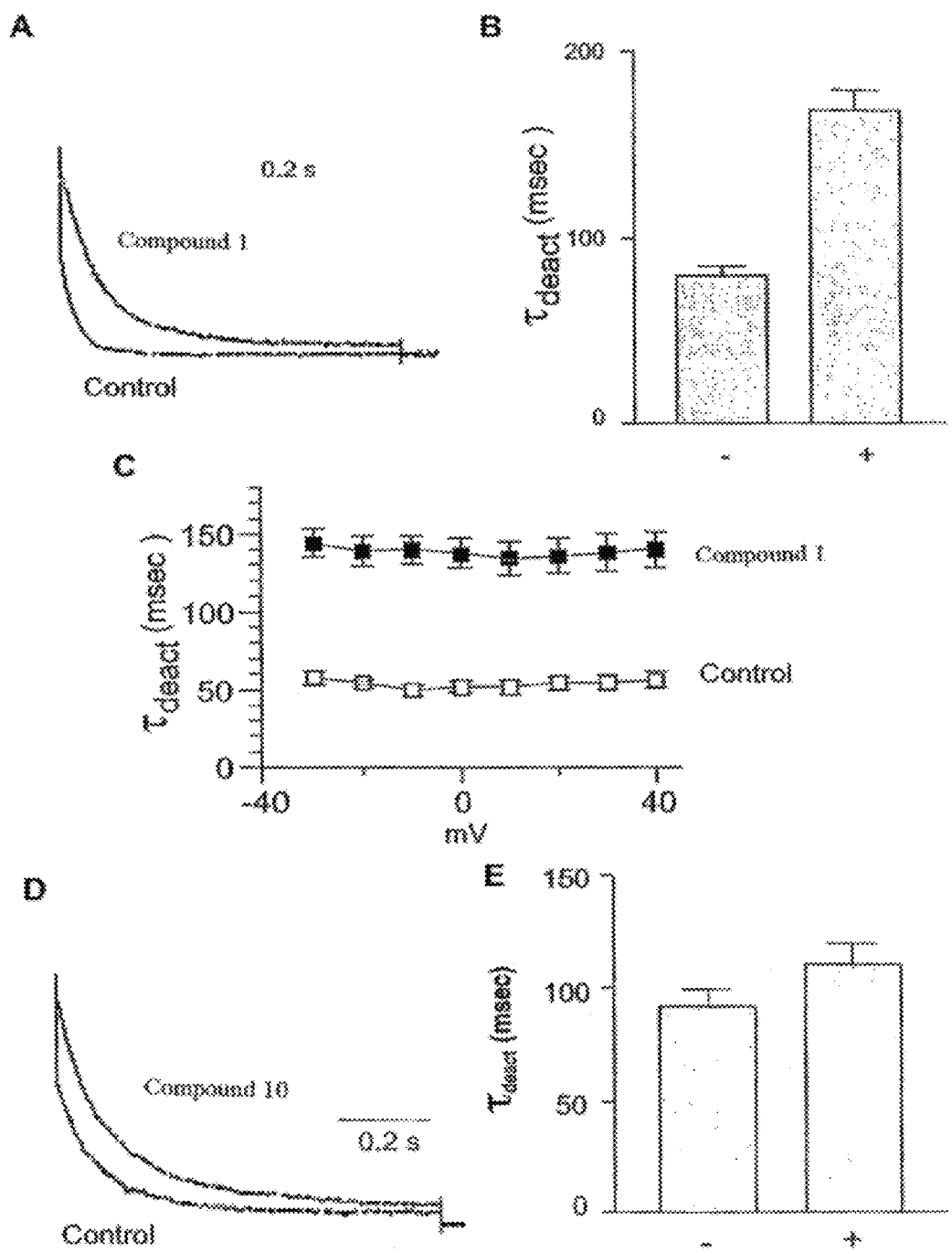

In FIG. 3A the tail current (reflecting the channel deactivation process) of a cell before (control) and following application of meclofenamic acid (Compound 1) is shown. The prepulse was −20 mV while the tail potential was −60 mV.

In FIG. 3B the time constant resulting from the exponential fit of the tail current decay ($\tau_{deact}$), in the absence (−) and the presence of meclofenamic acid (Compound 1) (+) is depicted.

Although meclofenamic acid (Compound 1) and 1-EBIO (Compound 10) did not affect the KCNQ2/3 activation kinetics, they markedly slowed down the deactivation process. The decay of the tail current or deactivation reflects the transition of the channel from the open state to the close state. As seen in FIG. 3A, the cells were depolarized to −20 mV and then repolarized to −60 mV. The decay of the tail current was fitted using one exponential function. In response to the addition of 100 µM meclofenamic acid (Compound 1), the time constant for deactivation increased by about 2-fold, from $\tau_{deact}$=79.6±4.5 msec to $\tau_{deact}$=167.5±11.6 msec (n=10). The results are highly significant, as shown in FIG. 3B and FIG. 3C.

As noted above, 1-EBIO (Compound 10) did affect significantly ($p<0.001$) the KCNQ2/3 deactivation kinetics. The decay of the tail current was fitted using one exponential function. In response to the addition of 100 µM 1-EBIO (Compound 10), the time constant for deactivation increased from $\tau_{deact}$=91.2±8.4 msec to $\tau_{deact}$=110.1±9.5 msec (n=14, FIG. 3E). FIG. 3D shows that 1-EBIO (Compound 10) slows down the deactivation kinetics of KCNQ2/3 channels.

Example 4

Inhibition of Evoked and Spontaneous Neuronal Activity by Meclofenamic Acid (Compound 1) and Diclofenac (Compound 2)

The inhibition of evoked and spontaneous neuronal activity by meclofenamic acid (Compound 1) and diclofenac (Compound 2) is discussed with reference to FIGS. 4A-4B, FIGS. 21A-21B and FIGS. 22A-22B.

In FIGS. 4A-4B neuronal activity depression by meclofenamic acid (Compound 1) is shown. In FIG. 4A, evoked rat cortical neuronal activity before (first row) during (second and third rows) and after (fourth and fifth rows) application of different meclofenamic acid (Compound 1) concentrations is presented. Each column corresponds to a different neuron.

In FIG. 4B, spontaneous activity recorded before, during and after 10 µM meclofenamic acid (Compound 1) application is depicted.

In FIG. 21A, representative experiments demonstrating the drastic effect of 10 µM meclofenamic acid on the number of evoked action potentials in cortical neurons that exhibited regular spiking patterns with no significant spike adaptation are shown.

In FIGS. 21B and 21C spontaneous activity before, during and after 10 µM linopirdine (a known blocker of M-currents, FIG. 21B) application and 10 µM meclofenamic acid (Compound 1, FIG. 21C) application are depicted.

In FIG. 22A representative experiments demonstrating the drastic effect of 25 µM diclofenac (Compound 2) on the number of evoked action potentials in cortical neurons that exhibited regular spiking patterns with no significant spike adaptation are shown.

In FIG. 22B spontaneous activity recorded before, during and after 25 µM diclofenac (Compound 2) application is depicted.

As discussed hereinabove, one of the main functions of the M-current is monitoring the excitability of neurons in the brain. Thus, the effect of meclofenamic acid (Compound 1) and diclofenac (Compound 2) on the evoked and spontaneous action potential activity of cultured rat cortical neurons was tested. Using the current-clamp configuration of the patch clamp technique, the effects of meclofenamic acid and diclofenac on evoked action potentials was first tested. The resting membrane potential was close to −60 mV and, when needed, was maintained at this level by injecting DC current. The obtained data clearly indicated that meclofenamic acid (Compound 1) and diclofenac (Compound 2) enhance the heterologously expressed M-current. The question remains how meclofenamic acid (Compound 1) and diclofenac (Compound 2) modulate the excitability of neurons expressing the M-current. To answer this question, a primary culture of rat cortical neurons and the current clamp configuration of the patch clamp technique were used.

First, how meclofenamic acid (Compound 1) and diclofenac (Compound 2) affect the evoked action potential activity of the rat cortical neurons was studied. In FIG. 4A it is seen that the evoked potentials are reversibly inhibited by meclofenamic acid (Compound 1), in the range of 5-20 µM. Each lane of FIG. 4A is recorded from a different neuron, using the current-clamp configuration of the patch-clamp technique. In FIG. 21A, representative experiments demonstrating how 10 µM meclofen drastically reduced the number of evoked action potentials in cortical neurons that exhibited regular spiking patterns with no significant spike adaptation are presented. As shown in FIG. 21A, within less than one minute, external exposure of 10 µM meclofen produced a widening of inter-spike intervals in the action potentials fired by the cortical neurons (FIG. 21A, second row). Following 2 minutes of opener exposure, only one spike could be evoked by the same depolarizing current (FIG. 21A, third row). Following 100 pA depolarizing current injection for 800 mseconds, 10 µM meclofen reduced the number of action potentials from 20±1 to 1±1 (n=10, $p<0.001$). Similar results were obtained with even lower concentrations of meclofen (5 µM) that consistently reduced the number of evoked action potentials (at 50 pA current injection, data not shown). Upon washout of meclofenamic acid for 1 minute, neurons recovered their initial spiking activity (25 Hz, FIG. 21A, fifth row).

Similar results were obtained with diclofenac (Compound 2). As shown in FIG. 22A, a cortical neuron exhibited a firing pattern with spike adaptation upon current injection (100 pA, 800 ms). Within 30 seconds superfusion with 25 µM diclofenac, there was a marked reduction in the number of evoked action potentials and a delay in first spike generation (FIG. 22A, second row). Following 1 minute exposure to diclofenac, no spike could be evoked upon identical current injection (FIG. 22A, third row). The depressing action of diclofenac could be quickly reversed by washout of the compound (FIG. 22A, forth-sixth rows).

Second, using higher density cultures of rat cortical neurons, spontaneous spiking activity was recorded.

As is clearly seen in FIG. 4B, t the spontaneous activity of the rat cortical neurons is completely but reversibly inhibited by 10 µM meclofenamic acid (Compound 1), FIG. 4B. As is further seen in FIGS. 21B and 21C, while 10 µM linopirdine, a known blocker of M-currents, significantly enhanced the frequency of spontaneous spiking (FIG. 21B), the perfusion of 10 µM meclofenamic acid produced within less than 2 minutes a profound depression of spontaneous action potentials (FIG. 21C). The depressing action of meclofenamic could be quickly reversed by washout of the compound (FIG. 21C).

As seen in FIG. 22B, similar to meclofenamic acid, the perfusion of 25 µM diclofenac (Compound 2) quickly and reversibly depressed the spontaneous spiking activity.

Example 5

The Effect of Meclofenamic Acid on M-Currents in Rat Cortical Neurons

Figure 23:
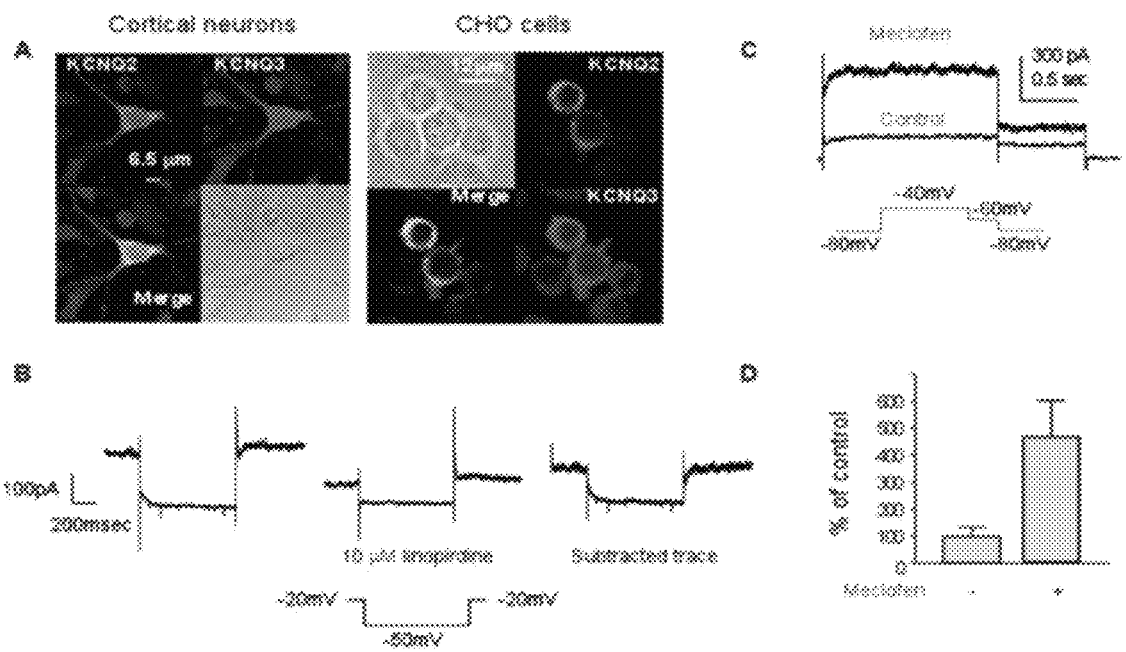

Considering the action of meclofenamic acid (Compound 1) and diclofenac (Compound 2) on recombinant KCNQ2/Q3 channels, the potential impact of these compounds on native M-currents that were recently found to be encoded in rat sympathetic and hippocampal neurons by the heteromeric assembly of KCNQ2 and KCNQ3 gene products [Shah et al. (2002) *J Physiol* 544:29-37; Tatulian et al. (2001) *A J Neurosci* 21:5535-5545; Wang et al. (1998) *Science* 282:2890-2893] was tested. Thus, the effects of meclofenamic acid on native M-currents of cultured rat cortical neurons were tested. First, it was evaluated, by means of double staining immunofluorescence, whether KCNQ2 and KCNQ3 alpha subunits were co-expressed in rat primary cortical neurons grown in culture for 10-14 days. As is shown in FIG. 23A, right panel, the polyclonal antibodies used were specific and recognized selectively KCNQ2 and KCNQ3 channel proteins when expressed in CHO cells. As is further demonstrated in FIG. 23A, left panel, confocal immunofluorescence microscopy showed co-localization of KCNQ2 and KCNQ3 immunoreactive proteins in cortical neurons with various morphologies, including pyramidal-like cells. The staining for both KCNQ2 and KCNQ3 was most prominent in the somata but was also present along the neuronal processes.

Then, the native M-current from pyramidal-like neurons was recorded. Since the M-current was very tiny and subjected to run-down, an external solution containing 0.5 µM TTX was used, to block voltage-gated $Na^+$ channels, in addition to 1 mM 4-AP plus 0.2 mM TEA that was used to block the fast transient A-type $K^+$ currents ($I_A$) and the TEA-/4-AP-sensitive delayed-rectifier $K^+$ currents such as those of the Kv3 family [Baranauskas et al. (2003) *Nat Neurosci* 6:258-266; Du et al. (1996) *J Neurosci* 16:506-518]. Then, a reasonable estimate of the contribution of the M-current was provided by the additional perfusion of 10 µM linopirdine, a blocker of M-channels (Wang et al., supra) and was revealed by subtracting the current traces, as is shown in FIG. 23B. In general, two different voltage protocols were used to reveal the M-current: (i) by holding the cell at −20 mV and stepping back to −50 mV to activate and deactivate the M-channels, respectively (as presented in FIG. 23B); and (ii) by holding the cell at −80 mV, stepping to −40 mV and then back to −60 mV to activate and deactivate the M-currents (as presented in FIG. 23C). Thus, representative recording of M-currents from a pyramidal-like neuron held at −20 mV and where the membrane potential was stepped to −50 mV are presented in FIG. 23B. Recording was done in 1 mM 4-AP and 0.2 mM TEA in the absence (left) or presence of 10 µM linopirdine (middle). The subtracted traces are shown in the right panel. The second protocol was used to evaluate the effect of meclofenamic acid. In this protocol, the membrane potential was stepped from −80 mV to −40 mV and the recording was done in 1 mM 4-AP and 0.2 mM TEA with and without 10 µM meclofen, in the absence or presence of 10 µM linopirdine. Representative trace showing the increase of the linopirdine-sensitive current by 10 µM meclofen is presented in FIG. 23C. As is shown in FIG. 23C, the subtracted traces (with and without 10 µM linopirdine) show that 10 µM meclofenamic acid produced a potent increase of the outward current generated by the non saturating step depolarization to −40 mV. As is shown in FIG. 23D, meclofenamic acid (10 µM) enhanced the outward current by 465±134 percents of control at −40 mV (n=5, p<0.01). These enhanced currents were blocked by 10 µM linopirdine (data not shown).

Example 6

The Effect of Diclofenac (Compound 2) on the Voltage Dependence Activation of the KCNQ2/3 Current and the Deactivation of KCNQ2/3 Current The leftwards-shift of the voltage dependence of activation of the KCNQ2/3 current induced by diclofenac (Compound 2) is discussed with reference to FIGS. 6A-6C.

In FIGS. 6A-6C the enhancement of the KCNQ2/3 current caused by diclofenac (Compound 2) is shown. In FIG. 6A whole cell currents of KCNQ2/3 heterogously expressed in CHO cells recorded before and after perfusion of 50 µM diclofenac are shown. In FIG. 6A the cell membrane was stepped from −90 mV to −50 mV (1 second) followed by tail step to −60 mV (0.75 second). Recordings were taken every 30 seconds. In FIG. 6B the percentage of the current presented in the presence (+) or absence (−) of diclofenac, where the control is 100%, taken from the experiment presented in FIG. 6A is shown. In FIG. 6C the normalized conductance ($G/G_{max}$) is plotted as a function of the voltage steps, for the control (open squares) and diclofenac (closed squares), for KCNQ2/3 current.

In FIG. 6C, the addition of 50 µM diclofenac (Compound 2) induced a leftward shift of −14.5 mV in the voltage-dependence of KCNQ2/3 activation, from $V_{50}$=−30.9±4.1 mV to $V_{50}$=−45.4±2.7 mV (n=7, p<0.01).

In FIG. 6C, it is seen that as with meclofenamic acid (Compound 1), treatment of CHO cells with diclofenac (Compound 2) slowed down the deactivation kinetics of KCNQ2/3 channels In FIGS. 6A and 6B it is seen that the KCNQ2/3 current amplitude is increased by diclofenac (2) at physiologically relevant potentials. In a train protocol, when the cells were stepped from −85 mV to −50 mV the application of diclofenac (Compound 2) induced an increase of the current amplitude by up to 262±26% (n=6).

The effects of diclofenac (Compound 2) were fully reversible (data not shown).

In general, these effects of both meclofenamic acid (Compound 1) and diclofenac (Compound 2) appear to result from a stronger impact of the openers on KCNQ2 than on KCNQ3 channel subunits, as is demonstrated in Example 7 below.

Example 7

Selectivity of Meclofenamic Acid (Compound 1) and Diclofenac (Compound 2) Action The opener properties of meclofenamic acid (Compound 1) and diclofenac on heteromeric KCNQ2/Q3 channels raise the question of whether these compounds act equally well or more selectively on either subunit. To address this problem, the effect of 50 µM meclofenamic acid on homomeric KCNQ2 channels and homomeric KCNQ3 expressed separately in CHO cells was tested. The results are presented in FIGS. 16A-D.

Figure 16A:
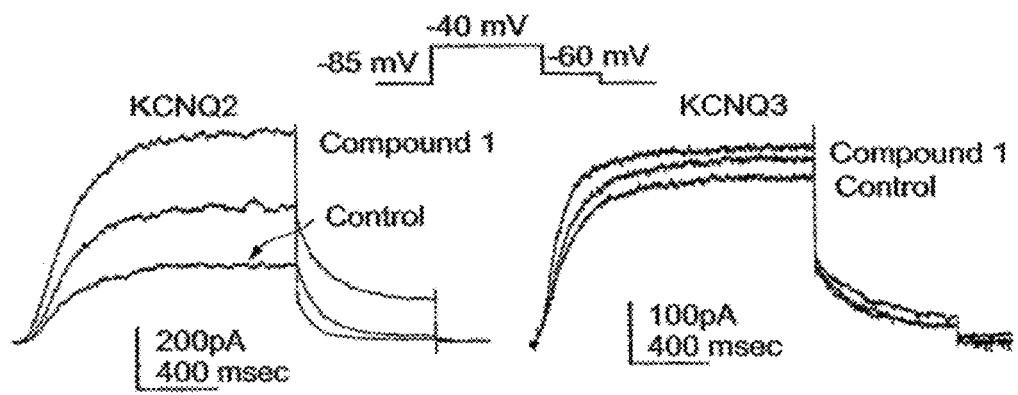
Figure 16B:
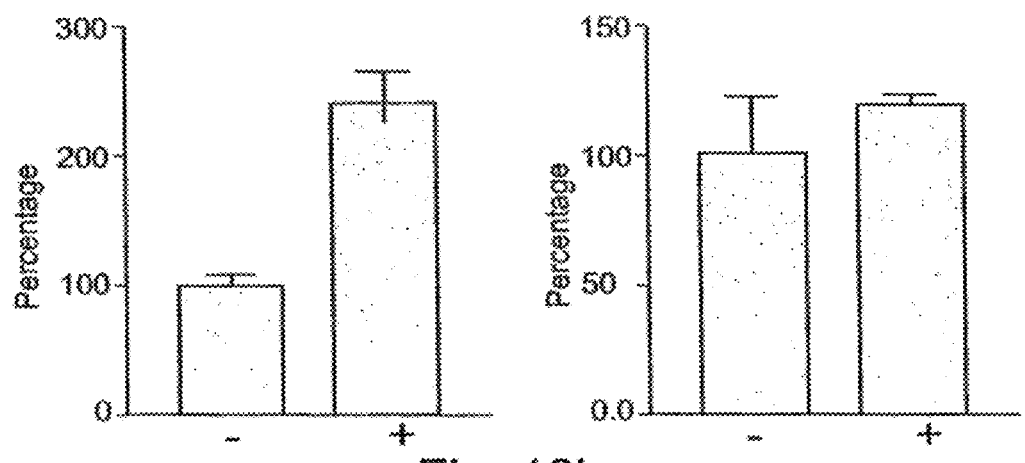
Figure 16C:
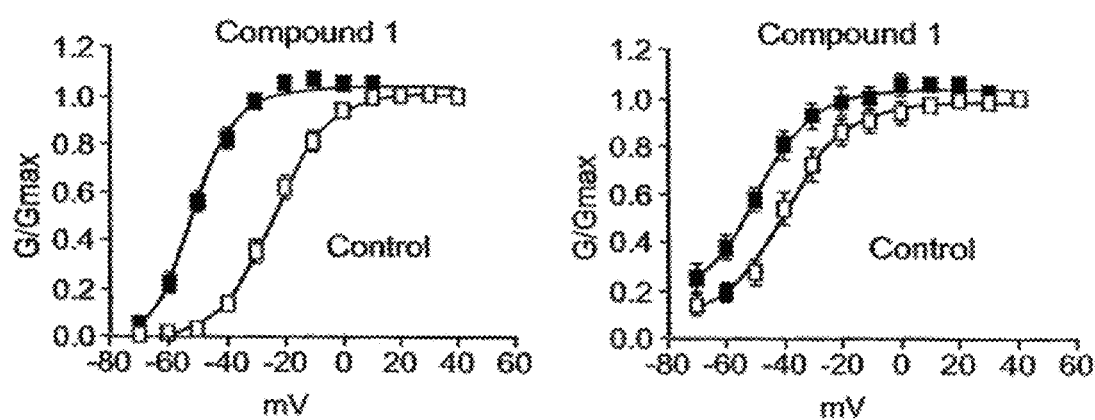

As is shown in FIG. 16C, it was found that meclofenamic acid generally exerted a stronger action on KCNQ2 than on KCNQ3 channels as it produced a substantial leftward shift of −26.9 mV in the activation curve of KCNQ2 channels, from $V_{50}=-23.6\pm2.2$ mV (n=8) to $V_{50}=-50.5\pm1.4$ mV (n=5) in control and meclofenamic acid-treated cells, respectively (FIG. 16C left panel, p<0.01). The leftward shift produced by meclofenamic acid on the activation curve of KCNQ3 channels was weaker (−15 mV) from $V_{50}=-39.0\pm3.5$ mV (n=11) to $V_{50}=-54.0\pm2.0$ mV (n=6) in control and meclofenamic acid-treated cells, respectively (FIG. 16C right panel, p<0.01).

Figure 16D:
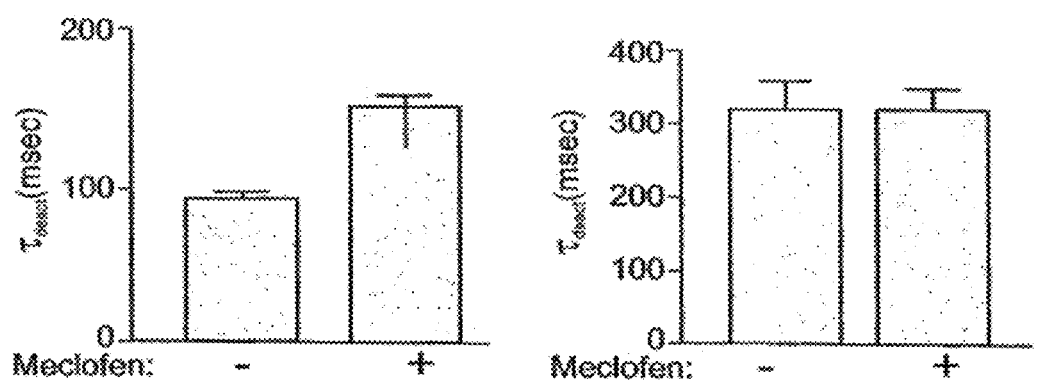

Meclofenamic acid (Compound 1) significantly reduced the speed of KCNQ2 channel closure with the time constant of deactivation increasing from $\tau_{deact}=92.6\pm3.9$ msec to $\tau_{deact}=152.7\pm4.9$ msec (FIGS. 16A and 16D; n=8, p<0.001). In contrast, it did not affect the deactivation kinetics of KCNQ3 channels ($\tau_{deact}=319.6\pm40.8$ msec and $\tau_{deact}=317.2\pm30.2$ msec for control and meclofenamic acid-treated cells, respectively, n=8).

Reflecting the stronger effect of the opener on KCNQ2 versus KCNQ3 channels, the application of 50 μM meclofenamic acid produced an increase of 240±26% and 120±4% of the KCNQ2 and KCNQ3 current amplitudes, respectively, when the cells were stepped from −85 mV to −40 mV (FIGS. 16A and B; n=8, p<0.001).

Interestingly, homomeric KCNQ1 and heteromeric KCNQ1/KCNE1 currents were not enhanced by 50 μM diclofenac or 50 μM meclofenamic acid across a range of test potentials between −50 to 0 mV (data not shown). Instead, both openers reduced the current amplitude at positive potentials (from 0 mV to 40 mV).

Similar results were obtained with diclofenac (data not shown).

To further address the selectivity of the compounds, the effects of meclofenamic acid (Compound 1) and diclofenac (Compound 2) towards other Kv channels were tested in *Xenopus* oocytes by measuring at non-saturating depolarizing potentials, the current amplitude of various Kv channels including Kv1.2, Kv1.5, Kv2.1, KCNQ1 and KCNQ2/Q3. The results are presented in Table 1 below. The effects of meclofen and diclofenac are expressed as percentage of the control amplitude, measured at the same potential in the absence of the tested compound. Data are expressed as mean±SEM of 5-8 separate experiments.

The obtained data clearly indicate that while meclofenamic acid (25 μM) and diclofenac (25 μM) increased KCNQ2/Q3 currents (at −40 mV) by 1.75 fold and 2.25 fold, respectively, they did not affect the current amplitude of other delayed-rectifier channels like, Kv1.2, Kv1.5 and Kv2.1. Interestingly, homomeric KCNQ1 and heteromeric KCNQ1/KCNE1 currents were not enhanced by diclofenac and meclofen across a range of test potentials between −50 to 0 mV (see, Table 1; additional data not shown).

TABLE 1

| | Channel (% of control current amplitude) | | | | |
|---|---|---|---|---|---|
| | Kv1.2 (−20 mV) | Kv1.5 (0 mV) | Kv2.1 (0 mV) | KCNQ (−40 mV) | KCNQ2/Q3 (−40 mV) |
| Meclofenamic acid (1) (25 μM) | 84 ± 6 | 98 ± 5 | 105 ± 6 | 95 ± 6 | 175 ± 15* |
| Diclofenac (2) (25 μM) | 90 ± 7 | 103 ± 7 | 100 ± 5 | 101 ± 6 | 225 ± 18* |

*significant change compared to control at p < 0.01 paired Student's t test

Example 8

Comparable Effects of Meclofenamic Acid (Compound 1) and/or Retigabine on the KCNQ2/3 Current The comparable opener properties exhibited by meclofenamic acid (Compound 1) or diclofenac (Compound 2) and those displayed by the anti-convulsant drug retigabine, including the leftward shift of the activation curve, the slowing of deactivation and the hyperpolarization of the membrane potential, are suggestive of a common site of action. To study this possibility, the potency of retigabine as measured by the leftward shift of the half-activation potential ($\Delta V_{50}$) as a function of the drug concentration in the absence or presence of a fixed $EC_{50}$ concentration (25 μM) of meclofenamic acid (Compound 1) have been tested.

The individual potency of retigabine and meclofenamic acid was measured by the leftward shift of the half-activation potential ($\Delta V_{50}$) as a function of the drug concentration. The data were fitted to a Hill equation, yielding $EC_{50}=2.0\pm1.3$ μM and $\eta_H=1.20\pm0.30$ (n=8) for retigabine and $EC_{50}=25.7\pm1.1$ μM and $\eta_H=2.1\pm0.5$ (n=8) for meclofenamic acid. For co-application experiments, the potency of retigabine as above in the presence of a fixed concentration of 25 μM meclofenamic acid ($EC_{50}$) was tested.

The results are presented in FIG. 20 and show that co-application of the two compounds produced additive effects. While dose-dependent applications of retigabine alone (upward triangles) and meclofenamic acid alone (squares) elicited maximal left-shifts of the half-activation potential ($\Delta V_{50}$) of −24±3 mV and −20±3 mV, respectively, co-exposure of 25 μM meclofenamic acid with increasing concentrations of retigabine produced a maximum $\Delta V_{50}$ of −32±4 mV (n=8; p<0.05; FIG. 20). Clearly, the effects of both drugs are not mutually occlusive but additive, which suggests that retigabine and meclofenamic acid act independently on KCNQ2/Q3 channels.

Example 9

Protection of Mice from Seizures Produced by Electroshock Using Meclofenamic Acid (Compound 1)

The effect of meclofenamic acid (Compound 1) in protecting mice from electroshock induced seizures is discussed with reference to FIG. 5.

In view of the strong depressing activity of meclofenamic acid (Compound 1) on cortical neurons, the anticonvulsant activity in mice subjected to seizures produced by electroshock was examined.

Five groups of 10 ICR mice each received intraperitoneally saline (control) or meclofenamic acid (Compound 1) at 25 mg/kg, 50 mg/kg, 100 mg/kg and 150 mg/kg and were subjected 30 minutes later to an electric shock (50 mA, 0.2 second duration, 60 Hz). The relative fraction of mice that did not produce seizures was plotted for each dose and the obtained data are presented in FIG. 5.

FIG. 5 shows that 50 mg/kg meclofenamic acid (Compound 1) significantly protected 50% of the mice from electroshock and at 100 mg/kg fully prevented seizures. At 150 mg/kg meclofenamic acid (Compound 1) led to sedation of the mice.

Example 10

Anti-Convulsant Effect of Diclofenac and Meclofenamic Acid in the Maximal Electroshock Seizure (MES) Test Considering the opener properties of meclofenamic acid (Compound 1) and diclofenac (Compound 2) on recombinant KCNQ2/Q3 channels and their dampening action on neuronal spiking discharges, the anti-convulsant effect of these compounds was further tested using the maximal electroshock seizure (MES) test in mice, which is generally thought to be a model of generalized tonic-clonic seizure in human [Macdonald and Kelly (1995) epilepsia 36 (suppl 2):S2-S12].

The results are presented in Table 2 below and clearly show that while MES produced hind limb extension in all mice that received intraperitoneal injection of vehicle solution, intraperitoneal injection of diclofenac 30 minutes or even 2 hours before the electroshock dose-dependently (25-200 mg/kg) suppressed the tonic extension induced by MES, with an $ED_{50}$ of 43 mg/kg, as is further shown in FIG. 24. For comparison, intraperitoneal injection of phenyloin and sodium valproate 30 minutes before the electroshock fully prevented hind limb extension at doses of 20 mg/kg and 500 mg/kg, respectively (n=10 each, data not shown).

The results further indicate that meclofenamic acid, Compound 1, had a weaker anti-convulsant action than diclofenac in the MES test. For example, intraperitoneal injection of meclofenamic acid at 50 mg/kg 30 minutes before the electroshock produced only 17% protection from hind limb extension, while diclofenac elicited 64% protection. In addition, at high doses (200 mg/kg) meclofenamic acid induced pro-convulsive toxic effects and hyperactivity.

TABLE 2

| | % Protection (number of animals) | | | |
|---|---|---|---|---|
| Dose | Diclofenac | | meclofenamic acid | |
| (mg/kg) | 30 minutes | 2 hours | 30 minutes | 2 hours |
| 0 | 0 (10) | 0 (9) | 0 (10) | 0 (10) |
| 25 | 10 (10) | ND | ND | ND |
| 50 | 64 (11) | 50 (4) | 17 (6) | ND |
| 100 | 92 (12) | 83 (6) | 75 (5) | 25 (4) |
| 200 | 100 (15) | 100 (6) | toxic | toxic |

Assays Conducted with Compounds 3-9

The N-phenylanthranilic acid derivatives, Compounds 3, 4, 5, 6, 7, 8 and 9, were tested for KCNQ2/3 opening activity as is described below. It is important to note that compounds 3-9 were also tested and found to have no effect on KCNQ1/KCNE1 cardiac channels and displayed a selective brain specificity. These results are not shown.

Example 11

The Effect of Compound 6 on KCNQ2/3 Channels

The effect of Compound 6 on recombinant KCNQ2/3 potassium channels heterogously expressed in CHO cells is discussed with reference to FIGS. 7A-7C and FIG. 25.

In FIGS. 7A-7C the effects of Compound 6 on KCNQ2/3 currents are shown. In FIG. 7A whole-cell currents recorded before and after perfusion of 25 μM Compound 6 are shown. In FIG. 7B the percentage of the current presented in the presence (+) or absence (−) of Compound 6, where the control is 100%, taken from the experiment presented in FIG. 7A. In FIG. 7C the normalized conductance ($G/G_{max}$) was plotted as a function of the voltage steps, for the control (open squares) and Compound 6 (closed squares), for KCNQ2/3 current are shown.

FIG. 7 shows the effects of 25 μM Compound 6 on recombinant KCNQ2/3 channels expressed in CHO cells. As with meclofenamic acid (Compound 1) and diclofenac (Compound 2), when externally applied, Compound 6 produces a significant leftward shift of about 13 mV in the voltage-dependence of KCNQ2/3 activation, from $V_{50}=-30.9\pm4.1$ mV to $V_{50}=-43.45\pm2.3$ mV (FIG. 7C, n=7, p<0.01).

In FIG. 7A it is seen that Compound 6 also slowed down the deactivation kinetics of KCNQ2/3 channels.

In FIGS. 7A and 7B it is seen that the KCNQ2/3 current amplitude was increased by Compound 6 at physiologically relevant potentials. In a train protocol, when the cells were stepped from −90 mV to −50 mV the application of 25 μM Compound 6 induced an increase of the current amplitude by up to 220% (n=10). The effect of Compound 6 was reversible (data not shown).

In FIG. 25 a dose-response curve presenting the percentages of current enhancement plotted as a function of Compound 6 concentration (expressed in log units) is presented. As can be seen in FIG. 25, the concentration-dependent current increase produced by Compound 6 at −50 mV yields an $EC_{50}=7\pm1$ μM (n=7).

The effect of Compound 6 was reversible (data not shown).

Example 12

The Effect of Compound 6 on Rat Cortical Neuron Cells

The effect of Compound 6 on recombinant KCNQ2/3 potassium channels heterogously expressed in rat cortical neuron cells is discussed with reference to FIGS. 8A-8B and FIGS. 9A-9C.

In FIGS. 8A-8B inhibition of the evoked neuronal activity by the Compound 6 is shown. In FIG. 8A neuronal activity, as evoked by square depolarizing current, inhibited by 10 μM Compound 6 and recovered after wash is shown. In FIG. 8A the depolarizing current was 50 pA for 800 msec. In FIG. 8B the evoked neuronal activity, using the ramp protocol, recorded before, after external perfusion of Compound 6 and recovered after wash is shown. In the ramp protocol depicted in FIG. 8B, the depolarizing current was ramped from 0 pA to 300 pA within 800 msec.

In FIGS. 9A-9C inhibition of the spontaneous neuronal activity by different concentration of Compound 6 is shown. Shown is spontaneous activity recorded before, after addition and after wash of Compound 6, for 20 μM in FIG. 9A, for 10 μM in FIG. 9B and 5 μM in FIG. 9C.

As one of the main functions of the M-current is to dampen the neuronal spiking discharges, what the effect of Compound 6 on the evoked and spontaneous action potential activity of cultured rat cortical neurons was examined. Using the current-clamp configuration of the patch clamp technique, the effects of Compound 6 on neuronal action potentials evoked either by a squared pulse (FIG. 8A; 50-300 pA, 800 msec) or a ramp (FIG. 8B; 0-300 pA in 800 msec) of depolarizing current were examined. The resting membrane potential was close to −60 mV and, when needed, was maintained at this level by injecting DC current. Superfusion of 10 μM Compound 6 reduced drastically and reversibly the number of evoked action potentials in cortical neurons. Within less than one minute following external superfusion of 10 µM Compound 6, the cortical neurons fired action potentials with a widening of interspike interval (FIG. 8A, 2nd row). After 2 minutes of opener exposure, only one spike could be evoked by the same depolarizing current (FIG. 8A, 3rd row). Thus, Compound 6 consistently reduced the number of evoked action potentials. Upon washout of the Compound for less than 2 minutes, neurons recovered their initial spiking activity (FIG. 8A, 5th row).

Similar results were obtained with ramp currents depicted in FIG. 8B.

Using higher density cultures of rat cortical neurons, spontaneous spiking activity was recorded (FIG. 9). Compound 6 dose-dependently (5 µM-20 µM) produced within less than 2 minutes a profound depression of spontaneous action potentials. The depressing action of Compound 6 could be reversed by washout of the Compound 6 Compound for all three concentrations.

Example 13

The Effect of Compound 6 on F-11 Neuron Cells

Recently, it was found that KCNQ2 and KCNQ3 α subunits are expressed in sensory dorsal root ganglion (DRG) neurons which are involved in nociceptive signaling pathways (Passmore et al., 23(18): 7227-36, 2003). There is strong evidence that hyperexcitability and ectopic discharge, which underlie allodynia, hyperalgesia and ongoing pain, are mediated by abnormal activity of a variety of ion channels. Thus, the ability of Compound 6 to modulate the spiking activity of F-11 neuronal cells and of cultured mouse DRG neurons (see Example 14 below) was tested.

F-11 neuronal cells represent a dorsal root ganglion x neuroblastoma hybrid cell line which displays several of the features of authentic DRG neurons (Platika et al. Trans Assoc Am Physicians. 98: 301-4, 1985) including the release of substance P, the presence of bradykinin, µ and δ-opioid receptors, the vanilloid receptor cation channel TRPV2, $Ca^{2+}$-activated $K^+$ channels as well as voltage-dependent $Na^+$, $Ca^{2+}$ and $K^+$ channels (Jahnel et al. Eur J. Biochem. 270(21): 4264-71, 2003).

Using the voltage-clamp protocol, linopirdine-sensitive voltage-dependent M-current was found to be expressed in F-11 neuronal cells (data not shown). In the current-clamp configuration, action potentials could be evoked by a squared pulse of depolarizing current.

As is shown in FIG. 26, external application of 10 µM Compound 6 completely and reversibly blocks the spikes generated in F-11 cells. In parallel, Compound 6 significantly hyperpolarizes the membrane potential (by 9±3 mV; n=8, p<0.01). As is further shown in FIG. 26, the membrane potential of the F-11 neuronal cell reversibly decreases from −59 mV to −67 mV. Similar results were obtained with mouse primary dorsal root ganglion neurons (data not shown).

Example 14

The Effect of Compound 6 on DRG Neuronal Activity

Thus, the ability of Compound 6 to modulate the spiking activity of rat DRG (dorsal rood ganglion) neurons was tested.

Using the voltage-clamp protocol described above a linopirdine-sensitive voltage-dependent M-current was found to be expressed in mouse small DRG neurons (data not shown). In the current-clamp configuration, trains of action potentials could be evoked by a squared pulse of depolarizing current (75 pA, 400 ms). As is shown in FIG. 27A, these small DRG neurons were featured by spikes associated with very strong after hyperpolarization. External application of 15 µM Compound 6 potently and reversibly blocked the spikes generated. Very similar results were obtained with 15 µM retigabine (data not shown). As is shown in FIG. 27B, when a solitary spike was evoked by a brief squared current pulse (300 pA, 1 ms), Compound 6 was able to reversibly prevent the generation of the single action potential.

Example 15

The Effect of Compound 5 on Kcnq2/3 Channels and on Rat Cortical Neurons

The effect of Compound 5 on recombinant KCNQ2/3 potassium channels heterogously expressed in CHO cells and on rat cortical neurons is discussed with reference to FIGS. 10A-10C.

In FIGS. 10A-10C the effects of Compound 5 on the neuronal activity and KCNQ2/3 current is shown. In FIG. 10A, evoked rat cortical neuronal activity recorded before, after application of 25 µM Compound 5, and after washing is shown. In FIG. 10B KCNQ2/3 currents recorded before (upper panel) and after (lower panel) application of 25 µM Compound 5. In FIG. 10B, the cell membrane was stepped from −80 mV to −40 mV in 10 mV increments (holding potential=−90 mV). In FIG. 10C the normalized conductance ($G/G_{max}$) was plotted as a function of the voltage steps, for the control (open squares) and Compound 5 (closed squares).

From FIGS. 10A-10C it is seen that Compound 5 has KCNQ2/3 potassium channels opening properties similar to those of Compound 6.

In FIG. 10C it is seen that 25 µM Compound 5 produced a significant leftward shift of ~8 mV in the voltage-dependence of KCNQ2/3 activation, from $V_{50}=-30.9\pm4.1$ mV to $V_{50}=-38.3\pm1.9$ mV (n=5, p<0.05).

In FIG. 10B it is seen that Compound 5 slowed down the deactivation kinetics of KCNQ2/3 channels. It is also seen that 15 µM Compound 5 enhances the current amplitude at the physiologically relevant potentials of −40 and −50 mV.

In FIG. 10A it is also seen that superfusion of 25 µM Compound 5 reversibly inhibited the number of evoked action potentials in cortical neurons.

Example 16

The Effect of Compound 3 on KCNQ2/3 Channels

The effect of Compound 3 on recombinant KCNQ2/3 potassium channels heterogously expressed in CHO cells is discussed with reference to FIGS. 11A-11B.

In FIGS. 11A-11B the KCNQ2/3 current increase in the presence of Compound 3 is shown. In FIG. 11A are shown currents in the absence (control) and presence of 25 µM Compound 3. In FIG. 11A, the cells were stepped to −50 mV for 1.5 second pulse duration and the interval between the pulses was 30 second. In FIG. 11B the percentage of the current presented in the presence (+) or absence (−) of Compound 3, where the control is 100%, is shown.

In FIGS. 11A-11B it is seen that Compound 3 has potent KCNQ2/3 potassium channel opening properties at 25 µM. In a train protocol, when the cells were stepped from −85 mV to −50 mV the application of 25 µM Compound 3 induced an increase of the current amplitude by up to 299±47% (n=6; p<0.002).

The effect of Compound 3 was fully reversible (data not shown).

Example 17

The Effect of Compound 4 on KCNQ2/3 Channels and on Rat Cortical Neurons

The effect of Compound 4 on recombinant KCNQ2/3 potassium channels heterologously expressed in CHO cells and on rat cortical neurons is discussed with reference to FIGS. 12A-12C.

In FIGS. 12A-12C, the effects of Compound 4 on neuronal activity and KCNQ2/3 current are shown. In FIG. 12A KCNQ2/3 currents recorded before (left panel) and after (right panel) application of 50 µM Compound 4 are shown. The cell membrane was stepped from −80 mV to −40 mV in 10 mV increments (holding potential=−90 mV). In FIG. 12B spontaneous cortical neuron activity recorded before, after addition of 20 µM Compound 4 and after a wash is shown. In FIG. 12D the normalized conductance ($G/G_{max}$) was plotted as a function of the voltage steps, for the control (open squares) and Compound 4 (closed squares).

In FIGS. 12A-12C it is evident that Compound 4 is a potent KCNQ2/3 channel opener. As seen in FIG. 12A when CHO cells were stepped from −85 mV to −50 mV and −40 mV, the application of 50 µM Compound 4 induced an increase of the current amplitude by more than 4-fold and 1.5-fold, respectively, as discussed hereinabove for Compound 3. This increase in KCNQ2/3 current amplitude results from the leftward shift produced by Compound 4 on the voltage-dependent curve of activation, FIG. 12C.

In FIG. 12B it is seen that when applied to rat cortical neurons, 20 µM Compound 4 markedly depressed the spontaneous spiking activity. As seen in FIG. 12B, the effect of Compound 4 was fully reversible.

Example 18

The Effect of Compound 9 on KCNQ2/3 Channels and on Rat Cortical Neurons

The effect of Compound 9 on rat cortical neurons is discussed with reference to FIG. 13. In FIG. 13 is shown spontaneous neuronal activity (action potentials) as modulated by 20 µM Compound 9.

As seen in FIG. 13, and in contrast to other molecules of the present invention, 20 µM of Compound 9 exhibit an inhibitory activity on evoked and spontaneous spiking activity of cortical neurons. However, in contrast to other molecules of the present invention, Compound 9 displayed only a weak opener action on recombinant KCNQ2/3 channels heterologously expressed in CHO cells. This result suggests that Compound 9 exerts neuronal depressant activity via mechanisms that do not involve KCNQ2/3 channels.

Example 19

The Effect of Compound 7 on KCNQ2/3 Channels and on Rat Cortical Neurons

The effect of Compound 7 on recombinant KCNQ2/3 potassium channels heterologously expressed in CHO cells and on rat cortical neurons is discussed with reference to FIGS. 14A-14D.

Figure 14A:
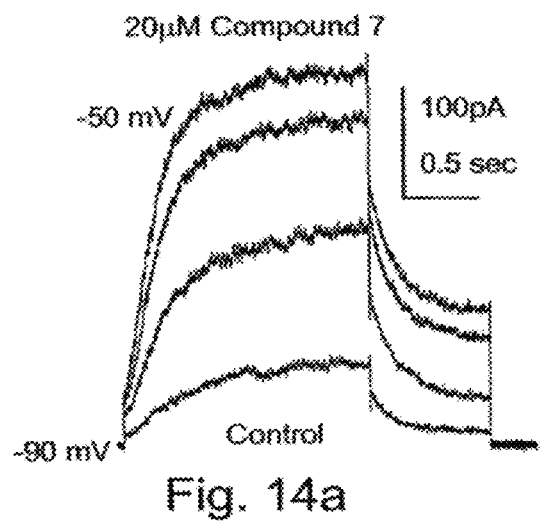
Figure 14B:
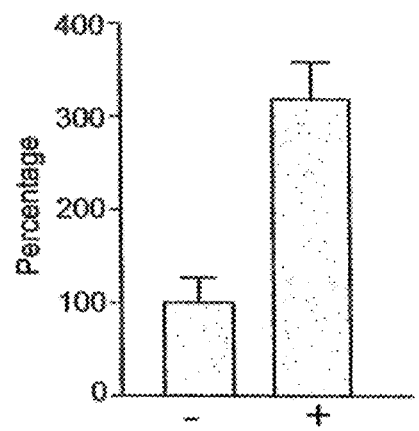
Figure 14C:
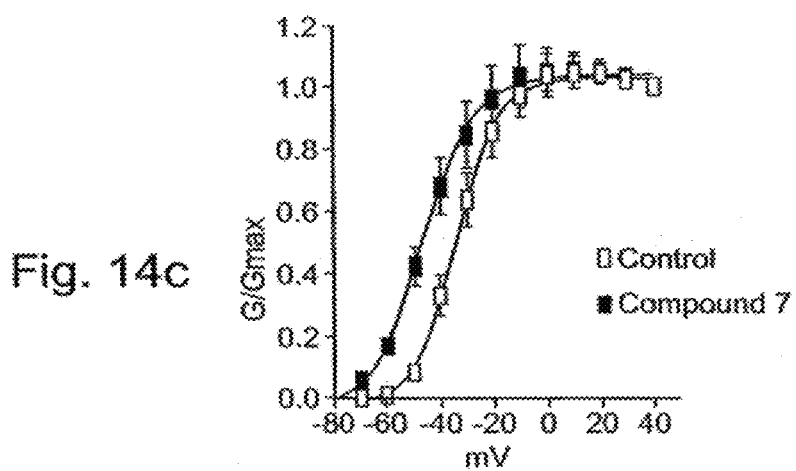
Figure 14D:
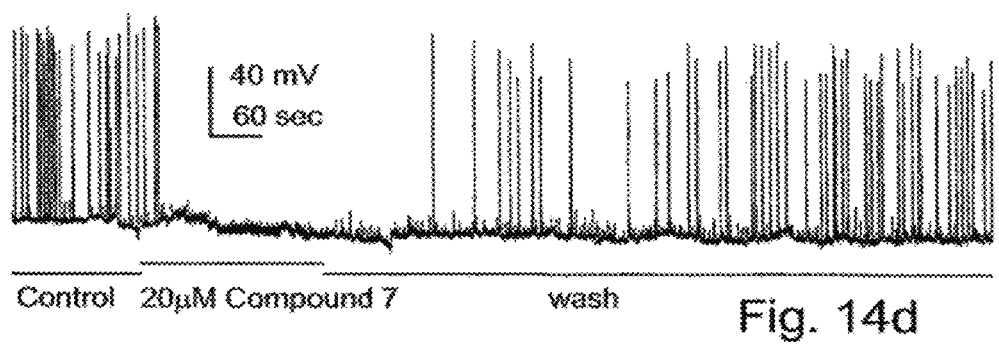

In FIGS. 14A-14D the effects of 20 µM Compound 7 on KCNQ2/3 channels and neuronal activity are shown. In FIG. 14A the KCNQ2/3 whole cell currents recorded before and after perfusion of 20 µM Compound 7 are shown. In FIG. 14B the percentage of the current presented in the presence (+) or absence (−) of Compound 7, where the control is 100%, taken from the experiment presented in FIG. 14A. In FIG. 14C, the normalized conductance of the KCNQ2/3 current ($G/G_{max}$) is plotted as a function of the voltage steps, for the control (open squares) and Compound 7 (closed squares). In FIG. 14D is shown the modulation of spontaneous neuronal activity (action potentials) by 20 µM Compound 7.

FIG. 14 shows the effects of Compound 7 on KCNQ2/3 channels. As with compounds 6 and 5 (discussed hereinabove), Compound 7 is a potent KCNQ2/3 channel opener with a marked leftward shift in the voltage dependent activation curve (FIG. 14C). This effect led to a potent increase of the channel amplitude as determined by a train protocol (FIGS. 14A and 14B). Likewise, 20 µM Compound 7 exhibited a very potent inhibitory activity on evoked and spontaneous spiking activity of cortical neurons (FIG. 14D). This effect was fully reversible.

Example 20

The Effect of Compound 8 on KCNQ2/3 Channels and on Rat Cortical Neurons

The effect of Compound 8 on recombinant KCNQ2/3 potassium channels heterologously expressed in CHO cells and on rat cortical neurons is discussed with reference to FIGS. 15A-15B.

In FIGS. 15A-15B, the evoked and spontaneous neuronal activity as modulated by Compound 8 is shown. In FIG. 15A, is shown evoked rat cortical neuronal activity recorded before, during and after application of 10 µM Compound 8. In FIG. 15B the spontaneous neuronal activity (action potentials) as modulated by 5 µM Compound 8 is shown.

FIGS. 15A-B show that low concentrations of Compound 8 produced a potent inhibitory activity on evoked and spontaneous spiking activity of cortical neurons. However, like Compound 9 discussed hereinabove, Compound 8 displayed only a weak opener action of recombinant KCNQ2/3 channels heterologously expressed in CHO cells. This result suggests that Compound 8 exerts neuronal depressant activity via mechanisms that do not involve KCNQ2/3 channels.

Example 21

Selectivity of Compound 6 Towards Various Ion Channels

The selectivity of Compound 6 towards other voltage-gated K+ channels (Kv) was evaluated by testing its action in *Xenopus* oocytes and, particularly, by measuring, at non-saturating depolarized potentials, the current amplitude of various Kv channels including Kv1.2, Kv1.5, Kv2.1, KCNQ1, KCNQ1/KCNE1 ($I_{KS}$) and KCNQ2/Q3. The current amplitude of the various channels was measured from a −80 mV holding potential. The results are presented in Table 3 below and clearly indicate that while Compound 6 (25 µM) increases KCNQ2/3 currents by 1.95 fold (at −40 mV), it does not affect the current amplitude of other delayed-rectifier channels like, Kv1.2, Kv1.5 and Kv2.1 as well as that of homomeric KCNQ1 and heteromeric KCNQ1/KCNE1 currents across a range of test potentials between −50 to 0 mV (see, Table 1; additional data not shown).

The effect of Compound 6 on recombinant NR1/NR2B NMDA receptor channels in transfected CHO cells at −60 mV holding potential was also tested. Compound 6 (5-25 μM) was superfused in an external solution containing 0.2 mM $CaCl_2$ and 10 μM glutamate with and without 1 mM L-alanine. The obtained data, also presented in Table 3 below, show that Compound 6 neither inhibits nor activates the NR1/NR2B currents. The effects of Compound 6 are expressed as percentage of the control amplitude, measured under the same conditions in the absence of the compound. Data are expressed as mean±SEM of 5-8 separate experiments (*p<0.01)

Further tested was the impact of 25 μM Compound 6 on native post-synaptic AMPA and $GABA_A$ currents, by measuring the amplitude of mEPSCs and mIPSCs, respectively, in cultured hippocampal neurons. The results are presented in Table 3 and in FIGS. 28A-28C and FIGS. 29A-29C. In FIG. 28A, representative traces of mEPSCs recorded before (3 upper traces) and after (3 lower traces) application of Compound 6 are shown. In FIG. 28B the normalized effect of Compound 6 on amplitude, rise time and decay time constants is shown. In FIG. 28C, a zoom on single mEPSC before (left) and after (right) application of 10 μM Compound 6 is shown. In FIG. 29A, representative traces of mIPSCs recorded before (3 upper traces) and after (3 lower traces) application of Compound 6 are shown. In FIG. 28B the normalized effect of Compound 6 on amplitude, rise time and decay time constants is shown. In FIG. 28C, a zoom on single mIPSCs before (left) and after (right) application of 10 μM Compound 6 is shown. The results clearly indicate that Compound 6 does not affect the amplitude of native post-synaptic AMPA and $GABA_A$ currents.

Additional data (not shown) indicate that mEPSCs and mIPSCs are sensitive to block by AMPA ionotropic receptor antagonists (10 μM NBQX) and $GABA_A$ channel antagonists (10 μM picrotoxin+10 μM bicuculline), respectively.

TABLE 3

| Ion channel type | % of control current amplitude |
| --- | --- |
| Kv1.2 (−20 mV) | 98 ± 9 |
| Kv1.5 (0 mV) | 95 ± 8 |
| Kv2.1 (0 mV) | 105 ± 9 |
| KCNQ1 (−40 mV) | 96 ± 6 |
| KCNQ1/KCNE1 [$I_{KS}$] (0 mV) | 102 ± 15 |
| KCNQ2/Q3 (−40 mV) | 195 ± 16 * |
| NR1/NR2B | 110 ± 5 |
| Hippocampal AMPA currents | 95 ± 6 |
| Hippocampal $GABA_A$ currents | 93 ± 4 |

Example 22

The Effect of Compound 6 on Native M-Currents and on Spontaneous EPSCS of Pyramidal Hippocampal Neurons To further determine the synaptic site of M-channel activation by Compound 6, its effects on spontaneous excitatory postsynaptic currents (EPSCs) that could be recorded from dense networks of hippocampal pyramidal neuron cultures was tested. The results are presented in FIGS. 30A-30E.

Figure 30:
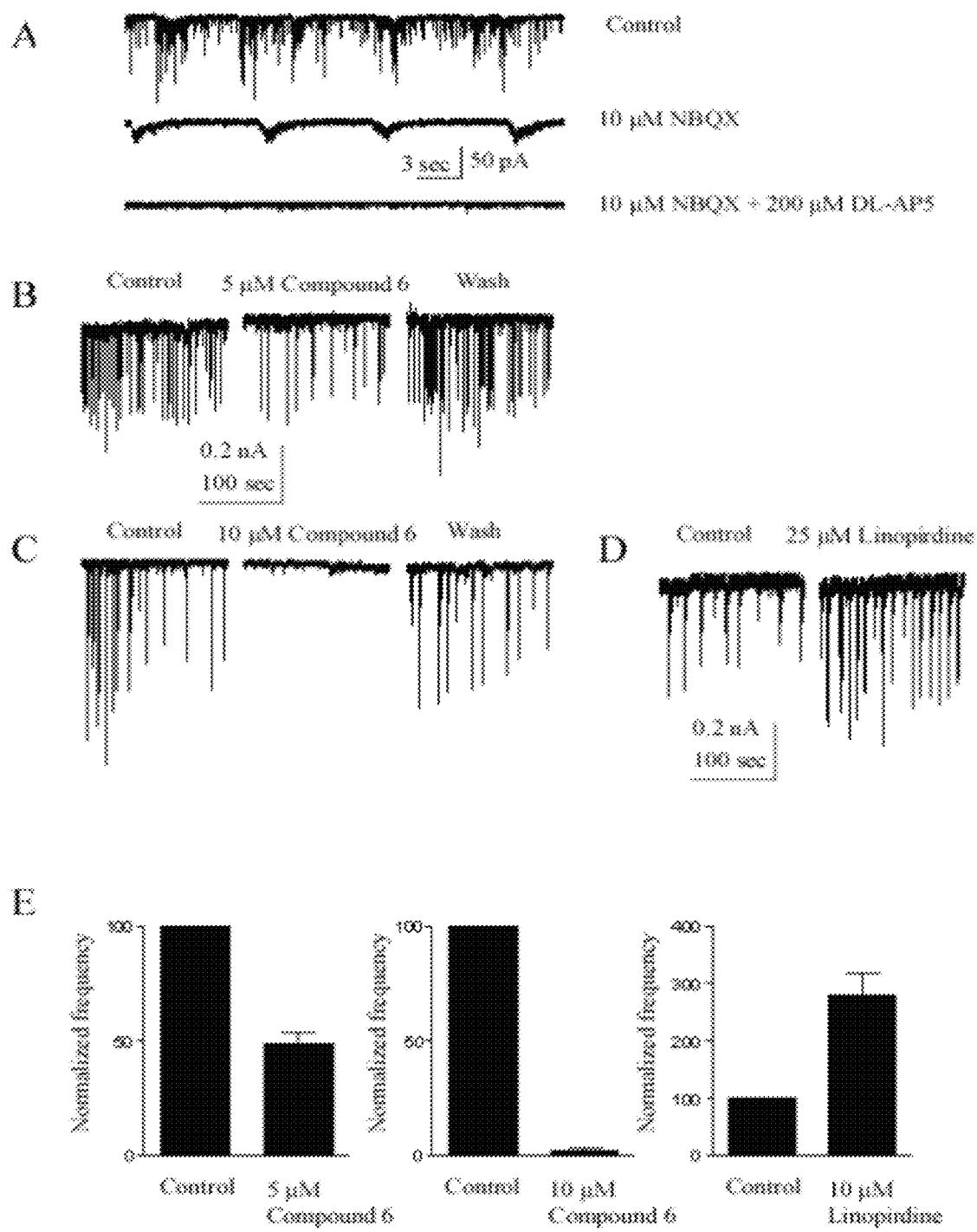

In FIGS. 30B and 30C, burst activity before (control), in the presence (Compound 6) and after (Wash) application of 5 μM (FIG. 30B) and 10 μM (FIG. 30C) Compound 6, as recorded at the voltage clamp mode is shown. In FIG. 30D, burst activity before (control) and in the presence of 25 μM Linopirdine is shown. In FIG. 30E, the normalized number of bursts appeared in 180 seconds time period for 5 μM (left panel), 10 μM (mid panel) of Compound 6 and 25 μM linopirdine (right panel) are shown. The holding potential was −70 mV. n=5-6.

Thus, using the voltage-clamp configuration of the patch-clamp technique, spontaneous EPSCs were isolated at −70 mV (holding potential) in the presence of 10 μM bicuculline and 10 μM picrotoxin to block $GABA_A$ receptor-mediated inhibitory postsynaptic currents. As is shown in FIG. 30A, under control conditions, the frequency of EPSCs is variable depending of the density of the hippocampal culture, ranging from 0.4 Hz to 2 Hz. The recorded EPSCs are totally blocked by bath application of 10 μM NBQX plus 200 μM DL-AP5, indicating that they are glutamate receptor-mediated postsynaptic events (FIG. 30A, third row). However, the majority of the EPSCs measured at −70 mV under the experimental recording conditions are mediated by AMPA receptors as most of the currents are blocked by 10 μM NBQX, leaving only a small fraction EPSC sensitive to the NMDA receptor blocker DL-AP5 (FIG. 30A).

As shown in FIG. 30B, external application of 5 μM Compound 6 causes a marked reduction in the frequency of spontaneous EPSCs, without any significant effects on the amplitude and the kinetics of the currents. While at 5 μM Compound 6 depresses the frequency of EPSCs up to 49±5% of control, at higher concentration (≥10 μM) it totally suppresses the occurrence of spontaneous EPSCs, as is shown IN FIGS. 30c and 30E. Noteworthy, the inhibitory effect of Compound 6 on EPSCs frequency is completely reversible, as shown in FIGS. 30B and 30C. Reflecting the existence of a substantial tonic M-current activity, the addition of the M-channel blocker linopirdine (10 μM) robustly increases the frequency of EPSCs by up to 278±41% of control, as shown in FIG. 30D.

Example 23

The Effect of Compound 6 on Native M-Currents and on Spike after Depolarization and Bursting Behavior of Hippocampal CA1 Pyramidal Neurons Using selective blockers and openers, it was recently shown that M-channels critically modulate the firing pattern of pyramidal hippocampal neurons by controlling the strength, duration and escalation into bursts of spike after depolarization (Yue and Yaari J. Neurosci., 24(19):4614-24, 2004). As previously shown with the M-channel opener retigabine, it is expected that activation of M-channels would reduce the spike ADP (after depolarization) (Yue and Yaari J. Neurosci., 24(19):4614-24, 2004). Thus, the ability of Compound 6 to elicit similar effects as those produced by retigabine in CA1 pyramidal neurons of rat hippocampal slices was tested, using sharp microelectrodes and the current-clamp recording configuration.

The results are presented in FIGS. 31A-31B. As is shown in FIG. 31A, left panel, injection into the somata of long suprathreshold depolarizing current pulses produce burst spiking behavior in control neurons. As is shown in FIG. 31A, right panel, extracellular application of Compound 6 (25 μM) produces a suppression of the burst and a trend to spike-frequency adaptation. Similar results were obtained with retigabine (data not shown).

To evaluate the effect of Compound 6 on the spike ADP, a brief depolarizing current pulse was injected to the neurons to elicit a solitary spike. FIG. 31B shows that Compound 6 markedly reduced the ADP size by about 60%, from 193.8±49.7 mV msec to 117.1±40.6 mV msec (n=10, p<0.05). Very similar results are obtained with retigabine (data not shown). These results clearly indicate that the inhibition of bursting produced by Compound 6 (or retigabine) is related to the marked depression of the spike ADP.

Example 24

Protection of Mice from Seizures Produced by Electroshock Using Compound 6

In view of the strong depressing activity of Compound 6 on cortical neurons, the anticonvulsant activity in mice subjected to seizures produced by electroshock was examined, using the MES test described above. Compound 6 dissolved in saline was injected intraperitoneally (in a volume of 10 ml/kg) at doses ranging from 6 mg/kg to 20 mg/kg to ICR adult mice and its anticonvulsant activity was compared with saline. Twenty minutes after drug administration, seizures were produced by electroshock (50 mA, 0.2 second duration, 60 Hz). The obtained data is presented in FIG. 32 and clearly shows a dose-dependent protective effect of Compound 6 against seizures, with $ED_{50}$=8.7 mg/kg.

Example 25

The Effect of Compound 6 on Cox Activity

In order to check whether compound 6 has specific COX-1 and COX-2 inhibition activity the C-26 cells assay described above was used. The obtained data is presented in FIG. 33 and includes 2-4 different experiments for each specific concentration of compound 6.

As can be seen in FIG. 33 and in Table 4 below, compound 6 did not block the COX activity in a concentration of up to 10 μM.

Example 26

Differential Effects of Compounds 2-7 on Cyclooxygenase Activity

SAR studies indicate three possible structural features of the channel opener binding site: (i) the presence of a hydrophobic pocket which could bind with the aromatic moiety of our molecules; (ii) the existence of a nucleophilic residue, which interacts with the carbonyl functionality and which must be an ester or a secondary amide and not a tertiary amide; and (iii) the presence of an electrophilic residue, which interacts with the terminal hydroxy group. These features are schematically illustrated in FIG. 34.

Importantly, it was found that the presence of a secondary amide is necessary to prevent a high affinity anti-COX1-2 activity. Using the C-26 cells assay described above, the inhibitory activity of Compounds 2-7 was tested and compared. The results are presented in Table 4 below.

As is shown in Table 4, it was found that while Compound 7, which has an ester functionality, exhibited a potent anti-COX activity with $IC_{50}$=11 nM, Compounds 4 and 6, both having a secondary amide functionality, displayed a very weak anti-COX activity with $IC_{50}$ values greater than 30 M.

Interestingly, it was further found that the nature and position of the substituents on the aromatic aniline moiety further affected the M-channel opener properties as well as the anti-COX activity of the compounds. Thus, for example, comparing the COX-inhibition activity of Compounds 3 and 6, both having a secondary amide functionality, reveals that the different substituents on the aniline moiety in Compound 3 as compared with Compound 6 conferred a relatively good anti-COX activity of the first with an $IC_{50}$=113 nM. This feature is further shown while comparing the results obtained with Compounds 3 and 5, which differ only by the substituent at the meta position of the aniline ring. The results obtained with these compounds show that replacing the Cl substituent by methyl dramatically affected the inhibition of the COX enzyme activity, such that an $IC_{50}$>10 M was demonstrated with Compound 5. Compound 2 (diclofenac), the parent compound from which Compound 6 is derived, potently and non-selectively inhibited both COX1 and COX2 activities with $IC_{50}$ values of about 0.3 nM.

TABLE 4

| Drug | $IC_{50}$ (nM) | Hillslope |
| --- | --- | --- |
| Compound 2 | 0.275 | −0.8 |
| Compound 3 | 113.5 | −0.6206 |
| Compound 4 | >30000 | |
| Compound 5 | 10300 | −0.4281 |
| Compound 6 | >30000 | |
| Compound 7 | 11.7 | −2.873 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific examples thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A pharmaceutical composition comprising, as an active ingredient, a compound having the general Formula I:

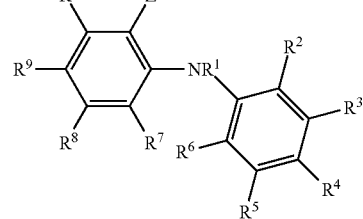

Formula I or a pharmaceutically acceptable salt thereof, wherein:
Z is an A-G(=K)—X—Y group, and wherein:
  A is alkyl or absent;
  G is C;
  K is selected from the group consisting of O and S;
  X is NRb; and
  Y is selected from the group consisting of an unsubstituted hydroxyalkyl, and a substituted or unsubstituted polyalkylene glycol residue,
  $R^1$ is selected from the group consisting of hydrogen, alkyl, cycloalkyl or aryl;
  each of $R^2$, $R^3$, $R^4$, $R^5$, $R^6$, $R^7$, $R^8$, $R^9$ and $R^{10}$ is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$, or, alternatively, at least two of $R^2$, $R^3$, $R^4$, $R^5$ and $R^6$, of $R^7$, $R^8$, $R^9$ and $R^{10}$ and/or of $R^{11}$, $R^{12}$, $R^{13}$, and $R^{14}$ form a five- or six-membered aromatic, heteroaromatic, alicyclic or heteroalicyclic ring;
  $R^{15}$ and $R^{16}$ are each independently selected from the group consisting of hydrogen, alkyl, cycloalkyl, aryl, carbonyl and sulfonyl, or, alternatively $R^{15}$ and $R^{16}$ form a five- or six-member heteroalicyclic ring; and
  each of Ra, Rb and Rc is independently selected from the group consisting of hydrogen, alkyl, cycloalkyl and aryl,
  wherein when Y is a polyalkylene glycol residue, said polyalkylene glycol residue does not include a —$ONO_2$ group or an antioxidant residue, and a pharmaceutically acceptable carrier,
  the composition being packaged in a packaging material and identified in print, in or on said packaging material, for use in increasing a current amplitude of a voltage-dependent potassium channel which comprises a KCNQ2 channel and/or a KCNQ3 channel and/or a KCNQ2/3 channel, said increasing said current amplitude comprising administering the pharmaceutical composition to a subject in need thereof.

2. The pharmaceutical composition of claim 1, wherein said polyalkylene glycol residue has a general formula III:

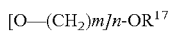   Formula III wherein:
  each of m and n is independently an integer of 1-10; and
  $R^{17}$ is hydrogen, alkyl, cycloalkyl or aryl.

3. The pharmaceutical composition of claim 1, wherein:
  K is O;
  each of $R^2$, $R^3$, $R^4$, $R^5$ and $R^6$ is independently selected from the group consisting of hydrogen, alkyl, halo and trihaloalkyl; and
  each of $R^7$, $R^8$, $R^9$ and $R^{10}$ is hydrogen.

4. The pharmaceutical composition of claim 1, wherein said compound is selected from the group consisting of:

3
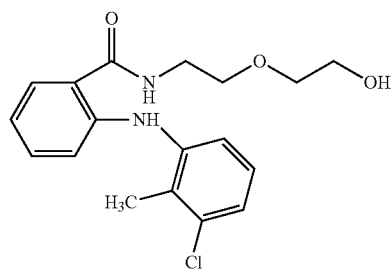

4
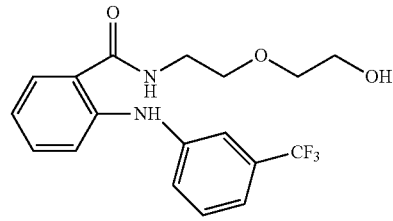

5
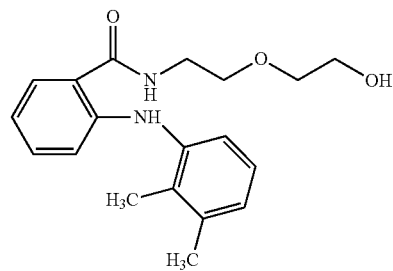

6
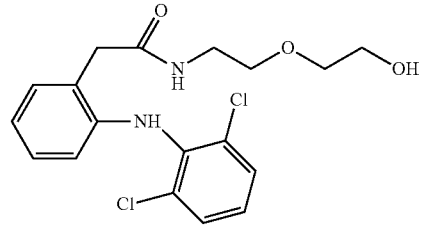

9
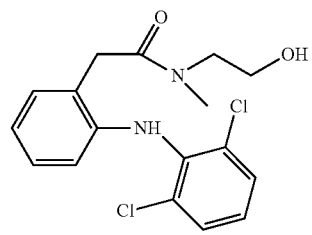

or a pharmaceutically acceptable salt thereof.

5. The pharmaceutical composition of claim 1, wherein increasing said current amplitude is for treating a condition or disorder is selected from the group consisting of epilepsy, ischemic stroke, migraine, ataxia, myokymia, neurogenic pain, neuropathic pain, Alzheimer's disease, Parkinson's disease, bipolar disorder, trigeminal neuralgia, spasticity, mood disorder, psychotic disorder, brain tumor, hearing and vision loss, anxiety and a motor neuron disease.

6. A pharmaceutical composition comprising, as an active ingredient, a compound having the general Formula I:

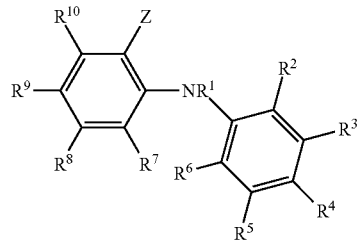   Formula I or a pharmaceutically acceptable salt thereof, wherein:
   Z is an A-G(=K)—X—Y group,
and wherein:
   A is alkyl or absent;
   G is C;
   K is selected from the group consisting of O and S;
   X is NRb; and
   Y is selected from the group consisting of an unsubstituted hydroxyalkyl, and a substituted or unsubstituted polyalkylene glycol residue,
   $R^1$ is selected from the group consisting of hydrogen, alkyl, cycloalkyl or aryl;
   each of $R^2$, $R^3$, $R^4$, $R^5$, $R^6$, $R^7$, $R^8$, $R^9$ and $R^{10}$ is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$, or, alternatively, at least two of $R^2$, $R^3$, $R^4$, $R^5$ and $R^6$, of $R^7$, $R^8$, $R^9$ and $R^{10}$ and/or of $R^{11}$, $R^{12}$, $R^{13}$ and $R^{14}$ form a five- or six-membered aromatic, heteroaromatic, alicyclic or heteroalicyclic ring;
   $R^{15}$ and $R^{16}$ are each independently selected from the group consisting of hydrogen, alkyl, cycloalkyl, aryl, carbonyl and sulfonyl, or, alternatively $R^{15}$ and $R^{16}$ form a five- or six-member heteroalicyclic ring; and
   each of Ra, Rb and Rc is independently selected from the group consisting of hydrogen, alkyl, cycloalkyl and aryl,
   wherein when Y is a polyalkylene glycol residue, said polyalkylene glycol residue does not include a —$ONO_2$ group or an antioxidant residue, and a pharmaceutically acceptable carrier,
   the composition being packaged in a packaging material and identified in print, in or on said packaging material, for use in treating schizophrenia.

7. The pharmaceutical composition of claim 1, wherein increasing said current amplitude is for treating a condition or disorder is selected from the group consisting of epilepsy, neuropathic pain and schizophrenia.

* * * * *